US011903921B2

(12) United States Patent
Mong et al.

(10) Patent No.: US 11,903,921 B2
(45) Date of Patent: Feb. 20, 2024

(54) SYSTEMS AND METHODS FOR TREATING CORONAVIRUS

(71) Applicants: Michael Mong, Grapevine, TX (US); Bao Tran, Saratoga, CA (US)

(72) Inventors: Michael Mong, Grapevine, TX (US); Bao Tran, Saratoga, CA (US)

( * ) Notice: Subject to any disclaimer, the term of this patent is extended or adjusted under 35 U.S.C. 154(b) by 95 days.

(21) Appl. No.: 17/222,718

(22) Filed: Apr. 5, 2021

(65) Prior Publication Data
US 2021/0338631 A1 Nov. 4, 2021

Related U.S. Application Data

(60) Provisional application No. 63/005,439, filed on Apr. 5, 2020.

(51) Int. Cl.
| | | |
|---|---|---|
| *A61M 16/00* | (2006.01) | |
| *A61K 31/353* | (2006.01) | |
| *A61K 31/164* | (2006.01) | |
| *A61K 31/05* | (2006.01) | |
| *A61K 9/00* | (2006.01) | |
| *A61K 38/47* | (2006.01) | |
| *A61H 3/00* | (2006.01) | |

(52) U.S. Cl.
CPC ............. *A61K 31/353* (2013.01); *A61H 3/00* (2013.01); *A61K 9/0078* (2013.01); *A61K 31/05* (2013.01); *A61K 31/164* (2013.01); *A61K 38/47* (2013.01); *A61M 16/0003* (2014.02); *C12Y 302/01035* (2013.01)

(58) Field of Classification Search
CPC .. A61H 31/00; A61H 31/02; A61H 2031/003; A61G 2200/325; A61G 13/12; A61G 12/1265; A61M 16/10; A61M 16/06; A61M 2016/0661
See application file for complete search history.

(56) References Cited

U.S. PATENT DOCUMENTS

| | | | |
|---|---|---|---|
| 3,751,727 | A | 8/1973 | Shepard et al. |
| 3,837,337 | A | 9/1974 | La Violette |
| 4,770,165 | A | 9/1988 | Hayek |
| 4,982,735 | A | 1/1991 | Yagata |
| 5,044,029 | A | 9/1991 | Vrzalik |

(Continued)

OTHER PUBLICATIONS

Jake Wenzel, A New Type of Ventilator with Potential to Disrupt the Respiratory Care Market, Mar. 9, 2020, https://medium.com/@jake.rethinker/a-new-type-of-ventilator-with-potential-to-disrupt-the-respiratory-care-market-804c8b7f22c8.

(Continued)

*Primary Examiner* — Margaret M Luarca
(74) *Attorney, Agent, or Firm* — DLA Piper LLP (US)

(57) ABSTRACT

Provided herein are methods of treatment, including methods of treating subjects having or at risk of having or having a viral infection, and specifically a SARS-CoV-2 viral infection. The methods provided include the administration of 4-methylumbelliferone (4-MU), palmitoylethanolamide (PEA), resveratrol, fisetin, $H_2$, nebulized hyaluronidase or combinations thereof. Also provided herein are a respiratory assistance device, methods of generating a customized respiratory assistance device, methods of treating a coronavirus infection, and methods of inhibiting a coronavirus infectivity, virulence and/or spread.

15 Claims, 16 Drawing Sheets

(56) References Cited

U.S. PATENT DOCUMENTS

| | | | |
|---|---|---|---|
| 5,573,498 | A | 11/1996 | Hayek |
| 5,938,626 | A | 8/1999 | Sugerman |
| 5,988,166 | A | 11/1999 | Hayek |
| 6,070,140 | A | 5/2000 | Tran |
| 6,345,618 | B1 | 2/2002 | Hayek |
| 6,398,992 | B1 | 6/2002 | Hayek |
| 7,502,498 | B2 | 3/2009 | Tran |
| 7,539,532 | B2 | 5/2009 | Tran |
| 8,431,617 | B2 | 4/2013 | Garaci et al. |
| 8,929,841 | B2 | 1/2015 | Rofougaran |
| 9,549,691 | B2 | 1/2017 | Tran |
| 10,293,565 | B1 | 5/2019 | Tran |
| 10,370,400 | B2 | 8/2019 | Nagy |
| 10,478,375 | B2 | 11/2019 | Antros |
| 11,278,518 | B2 | 3/2022 | Bollyky et al. |
| 2005/0011518 | A1* | 1/2005 | Biondo ............ A61G 7/0513 601/DIG. 7 |
| 2005/0035477 | A1 | 2/2005 | Jacobson |
| 2007/0187855 | A1 | 8/2007 | Jacobson |
| 2016/0206237 | A1 | 7/2016 | Friedlander |

OTHER PUBLICATIONS

Klum, Wearable Cardiorespiratory Monitoring Employing a Multimodal Digital Patch Stethoscope: Estimation of ECG, PEP, LVET and Respiration Using a 55 mm Single-Lead ECG and Phonocardiogram.
Zhu, Digital Clay, at http://www.imdl.gatech.edu/haihong/DigiClay/Clay_MultiCell.html.
Esquinas et al. "Noninvasive mechanical ventilation in high-risk pulmonary infections: a clinical review", European Respiratory Review, May 2014, 23:427-438.
Henderson et al., "Does prone positioning improve oxygenation and reduce mortality in patients with acute respiratory distress syndrome?. " Canadian respiratory journal vol. 21,4 (2014): 213-5.
Hesselink et al., "Palmitoylethanolamide: A Natural Body-Own Anti-Inflammatory Agent, Effective and Safe against Influenza and Common Cold", International journal of inflammation, Jun. 2013, 2013(151028):1-8.
Lin et al., "Effective inhibition of MERS-CoV infection by resveratrol." BMC Infect Dis., 2017, 17(114):1-10.
Louten, "Virus Replication." Essential Human Virology (2016): 49-70.
PCT International Search Report and Written Opinion International Application No. PCT/US2021/025811, dated Sep. 16, 2021, 12 pages.
Petrosillo et al., "COVID-19, SARS and MERS: are they closely related?" Clinical Microbiology and Infection, vol. 26, Issue 6, Mar. 28, 2020 (Mar. 28, 2020), pp. 729-734.
Lall et al., "Dietary flavonoid fisetin increases abundance of high-molecular-mass hyaluronan conferring resistance to prostate oncogenesis", Oxford University Press, Carcinogenesis, Jun. 2016, 37(9): 918-928.
Albtoush & Petrey, "The role of hyaluronan synthesis and degradation in the critical respiratory illness COVID-19", American Journal of Physiology, Apr. 2022, 13 pages.
Yang et al., "Human Identical Sequences, hyaluronan, and hymecromone—the new mechanism and management of COVID-19", Molecular Biomedicine, May 2022, 3:15, 22 pages.
Rosser et al., "Oral hymecromone decreases hyaluronan in human study participants", The Journal of Clinical Investigation, May 2022, 132(9): e157983, 9 pages.
Kratochvil et al., "Biochemical, biophysical, and immunological characterization of respiratory secretions in severe SARS-COV-2 infections", JCI Insight, Jun. 2022, 7(12): e152629, 17 pages.
Yang et al., "Hymecromone: a clinical prescription hyaluronan inhibitor for efficiently blocking COVID-19 progression", Signal Transduction and Targeted Therapy, Mar. 2022, 7: 91, 10 pages.
Li et al., "SARS-CoV-2 RNA elements share human sequence identity and upregulate hyaluronan via NamiRNA-enhancer network", eBioMedicine, Feb. 2022, 76: 103861, 18 pages.
Matsuyama et al., "Comorbidity-associated glutamine deficiency is a predisposition to severe COVID-19", Cell Death & Differentiation, Oct. 2021, 28: 3199-3213.
Matsuyama et al., "An aberrant STAT pathway is central to COVID-19", Cell Death & Differentiation, Oct. 2020, 27: 3209-3225.

* cited by examiner

SYSTEMS AND METHODS FOR TREATING CORONAVIRUS

CROSS-REFERENCE TO RELATED APPLICATIONS

This application claims benefit of priority under 35 U.S.C. § 119(e) of U.S. Provisional Patent Application Ser. No. 63/005,439, filed Apr. 5, 2020, the contents of which are incorporated herein by reference in its entirety.

BACKGROUND OF THE INVENTION

Field of the Invention

The present invention relates generally to methods and devices for treating subjects having or at risk of having or having a viral infection, and more specifically to methods and devices for treating coronavirus and SARS-CoV-2 infections.

Background Information

Coronavirus disease 2019 (COVID-19) is a respiratory illness that can spread from person to person. The virus that causes COVID-19 is a coronavirus, SARS-CoV-2, that was first identified during an investigation into an outbreak in Wuhan, China. The virus probably emerged from an animal source but is now spreading from person to person. The virus spreads mainly between people who are in close contact with one another (within about 6 feet) through respiratory droplets produced when an infected person coughs or sneezes. It is also possible that a person can get infected by touching a surface or object that has the virus on it and then touching their own mouth, nose, or possibly their eyes. Patients with COVID-19 have had mild to severe respiratory illness with symptoms of fever, cough, shortness of breath. Severe complications from this virus can include pneumonia in both lungs, multi-organ failure and in some cases death. Very few to no universally accepted therapies seem efficient to treat the disease.

COVID-19 appears to be related to cytokine release syndrome (CRS) or cytokine storm syndrome (CS S) which is a form of systemic inflammatory response syndrome (SIRS) that can be triggered by a variety of factors such as infections and certain drugs. It occurs when large numbers of white blood cells are activated and release inflammatory cytokines, which in turn activate yet more white blood cells. Severe cases have been called cytokine storms. When occurring as a result of drug administration, it is also known as an infusion reaction. CRS occurs when large numbers of white blood cells, including B cells, T cells, natural killer cells, macrophages, dendritic cells, and monocytes are activated and release inflammatory cytokines, which activates more white blood cells in a positive feedback loop of pathogenic inflammation. Immune cells are activated by stressed or infected cells through receptor-ligand interactions. This can occur when the immune system is fighting pathogens, as cytokines produced by immune cells recruit more effector immune cells such as T-cells and inflammatory monocytes (which differentiate into macrophages) to the site of inflammation or infection. In addition, pro-inflammatory cytokines binding their cognate receptor on immune cells results in activation and stimulation of further cytokine production. The production of other signaling and structural molecules such as hyaluronan can also be stimulated. This process, when dysregulated, can be life-threatening due to systemic hyper-inflammation, hypotensive shock, and multi-organ failure.

The first published autopsy record of the gross anatomy of a COVID-19 victim was of an 85-year-old male who died of SARS-CoV-2 after 28 days in the hospital. The key features of the report included (i) a description of the lung weights of the victim, which totaled 1940 g, revealing abnormally heavy lungs suggestive of an accumulation of greater than a liter of water, (ii) a cut surface of the lung showing a large amount of viscous secretions overflowing from the alveoli suggestive of hyaluronan, (iii) the presence of a white foamy mucus in the tracheal lumen suggestive of possible hyaluronan, and (iv) the presence of jelly-like mucus seen in the bronchus lumen of the right lung.

More recent autopsies have confirmed that the lungs of deceased patient are filled with clear liquid jelly, much resembling the lungs of wet drowning "suggesting a connection between hyaluronan and acute respiratory distress syndrome (ARDS) as a reflection of the increased levels of hyaluronan observed in mice infected with H1N1 Influenza A virus." Further, histologic lung sections obtained at autopsy from multiple COVID-19 victims stained specifically for hyaluronan, revealed hyaluronan abundantly obstructing alveoli, as well as being present in thickened alveolar interstitium.

Based on this analysis, and in the absence of a treatment of SARS-CoV-2 infection that can be administered to patients upon becoming symptomatic, and prior to developing a severe disease, the present invention describes the use of palmitoylethanolamide (PEA), resveratrol, fisetin, $H_2$, hyaluronidase, Hymecromone (4-Methylumbelliferone, 4-MU), positive, negative and biphasic pressure ventilation or a combination thereof in COVID-19 patients.

SUMMARY OF THE INVENTION

The present invention is based on the seminal discovery that SARS-CoV-2 induces a sudden rise in hyaluronan levels leading to significant impairment of normal lung function that can be treated by the modulation of hyaluronan levels.

In one embodiment, the present invention provides a method of treating a subject having or at risk of having or having a viral infection including administering one or more of 4-MU (4-methylumbelliferone), PEA (palmitoylethanolamide), resveratrol, fisetin, $H_2$, nebulized hyaluronidase or any combination thereof to the subject upon exposure or upon becoming symptomatic.

In one embodiment, the present invention provides a method of treating a subject having or a risk of having a viral infection including administration one or more of a hyaluronan inhibitor, a leukocyte modulating compound, an antioxidant, a hyaluronidase, or any combination thereof to the subject upon exposure, or becoming symptomatic.

In one aspect, the viral infection is caused by a coronavirus infection. In one aspect, the coronavirus is SARS-CoV-2.

In one aspect, administration is by an oral, intravenous, intraperitoneal, intraarterial, sublingual, or nasal route or by infusion, inhalation, or nebulization. In some aspects, PEA is co-administered with fisetin and/or resveratrol. In another aspect, the subject is administered from about 400 mg to 4800 mg per day of PEA, fisetin, and/or resveratrol. In some aspects, the subject is administered about 800 mg to 4000 mg per day of PEA, fisetin, and/or resveratrol. In other aspects, the subject is administered about 800 mg to 2400 mg per day of PEA, fisetin, and/or resveratrol. In another aspect, the subject is administered 800 mg three times per day of PEA, fisetin, and/or resveratrol.

In some aspects, PEA is co-administered with resveratrol.
In some aspects, PEA is co-administered with fisetin.
In some aspects, PEA is co-administered with 4-MU.
In some aspects, resveratrol is co-administered with 4-MU.
In some aspects, resveratrol is co-administered with fisetin.
In some aspects, fisetin is co-administered with 4-MU.
In some aspects, 4-MU is co-administered with resveratrol and PEA.

In one aspect, external non-invasive negative, positive or biphasic pressure breathing assistance is further provided to the subject. In some aspects, administering 4-MU, PEA, resveratrol, fisetin, $H_2$, nebulized hyaluronidase or a combination thereof treats, blocks and/or disrupts virus-associated membrane trafficking and/or filopodia, infectivity, virulence, and/or spread. In other aspects, the subject is further positioned in prone position on a respiratory assistance device.

In another embodiment, the invention provides a method of inhibiting a coronavirus infectivity, virulence and/or spread in a subject including inhibiting coronavirus-associated membrane trafficking and/or filopodia, wherein inhibiting coronavirus-associated membrane/trafficking and/or filopodia includes administering to the subject having or at risk of having a coronavirus infection 4-methylumbelliferone (4-MU), palmitoylethanolamide (PEA), resveratrol, fisetin, and/or nebulized hyaluronidase, upon exposure or upon becoming symptomatic, thereby inhibiting a coronavirus infectivity, virulence and/or spread.

In an additional embodiment, the invention provides a respiratory assistance device including: a) a support base having a top surface; b) a support layer coupled to the top surface of the support base, the support layer including: a first opening sized to accommodate a user's face in prone position; and a second opening sized to accommodate the user's chest and abdomen in prone position, the second opening having a sealing surface disposed about the perimeter of the second opening configured to contact the user's chest and abdomen and fluidly seal the second opening when the user's chest and abdomen contact the sealing surface in the prone position; c) a reversibly inflatable cavity within the support base, wherein the cavity is disposed interior to the support base and sealed by the user's chest and abdomen in the prone position; d) a pump in fluid connection with the cavity and operable to control inflation and deflation of the cavity such that the user's chest and abdomen are moved to assist breathing of the user by applying positive and negative pressure to the chest and abdomen during inflation and deflation of the cavity; e) a breathing device in connection with the first opening configured to deliver a gaseous fluid to the mouth and/or nose of the user; and f) one or more sensors configured to detect position and/or a physiological parameter of the user.

In one aspect, the breathing device includes a face mask, an inhaler and/or a nebulizer. In other aspects, the gaseous fluid includes air, a treatment gas, a therapeutic agent, or a combination thereof. In some aspects, the therapeutic agent is selected from the group consisting of 4-methylumbelliferone (4-MU), palmitoylethanolamide (PEA), resveratrol, fisetin, $H_2$, nebulized hyaluronidase, and any combination thereof in other aspects, the device further includes an isolation barrier. In various aspects, the isolation barrier is configured to isolate a user's head, head and torso, or entire body from ambient environment. In one aspect, the one or more sensors are configured to detect pressure, body position, heart rate, gaseous fluid content and/or level, body temperature, moisture, or a combination thereof. In other aspects, the device further includes a computer module in operable connection with the one or more sensors, the computer module having a processor with functionality to receive and process data from the one or more sensors to control inflation and deflation of the cavity and/or delivery of gaseous fluid. In various aspects, the processor has functionality to maintain a static pressure within the cavity sufficient to expand the user's lungs and abdomen between inflation and deflation of the cavity. In some aspects, dimensions of the support layer are customized to the user by obtaining measurements of the user. In one aspect, the measurements are obtained by manual measurement of the user and/or imaging of the user. In some aspects, imaging includes 1-dimensional (1-D), 2-dimensional (2-D) and/or 3-dimensional (3D) scans of the user.

In one embodiment, the invention provides a method of generating the respiratory assistance device described herein customized for a user including: a) measuring the user's body, or portion thereof; b) manufacturing the support layer such that the first opening and/or the second opening conforms to the size and shape of the user; and c) securing the support layer to the support base, thereby generating a customized respiratory assistance device.

In one aspect, measuring includes manual measurement of the user and/or imaging of the user.

In another embodiment, the invention provides a method of treating a subject having a coronavirus infection including: a) positioning the subject in prone position on the respiratory assistance device described herein, or a customized respiratory assistance device generated by the method described herein; and b) administering treatment to the subject via the respiratory assistance device; and optionally c) administering 4-methylumbelliferone (4-MU), palmitoylethanolamide (PEA), fisetin, $H_2$, nebulized hyaluronidase, or a combination thereof, to the subject via the breathing device, thereby treating the coronavirus infection in the subject.

In one aspect, administering 4-MU, PEA, resveratrol, fisetin, $H_2$, nebulized hyaluronidase or any combination thereof treats, blocks and/or disrupts virus-associated membrane trafficking, filopodia, infectivity, virulence, and/or spread. In another aspect, positioning the subject on the respiratory assistance device releases pressure off the diaphragm, lungs and blood vessels and improves perfusion, lymphatic circulation, cardiovascular function and/or brain function.

BRIEF DESCRIPTION OF THE DRAWINGS

FIG. 1 is a schematic representation showing pathology and treatment of coronavirus related illnesses.

FIG. 2 is a diagram showing viral load over the course of viral infection.

FIG. 3 is a flow chart diagram illustrating an exemplary process for treating virus infections in one embodiment of the invention.

FIG. 4 is a schematic representation of a portable emergency negative pressure respiratory assistance device in one embodiment of the invention.

FIGS. 5A-D show various exemplary body support systems for automated handling of issues in an intubation system including endotracheal tubes or lines. FIG. 5A shows an exemplary smart bed/mattress that can be used standalone or with the processes for COVID-19 treatment. FIG.

5B shows an actuated pin grid array of actuators which consists of a glass tube with graphite pistons inside. FIG. 5C shows a schematic representation of a touch sensor array.

Figure 7A:
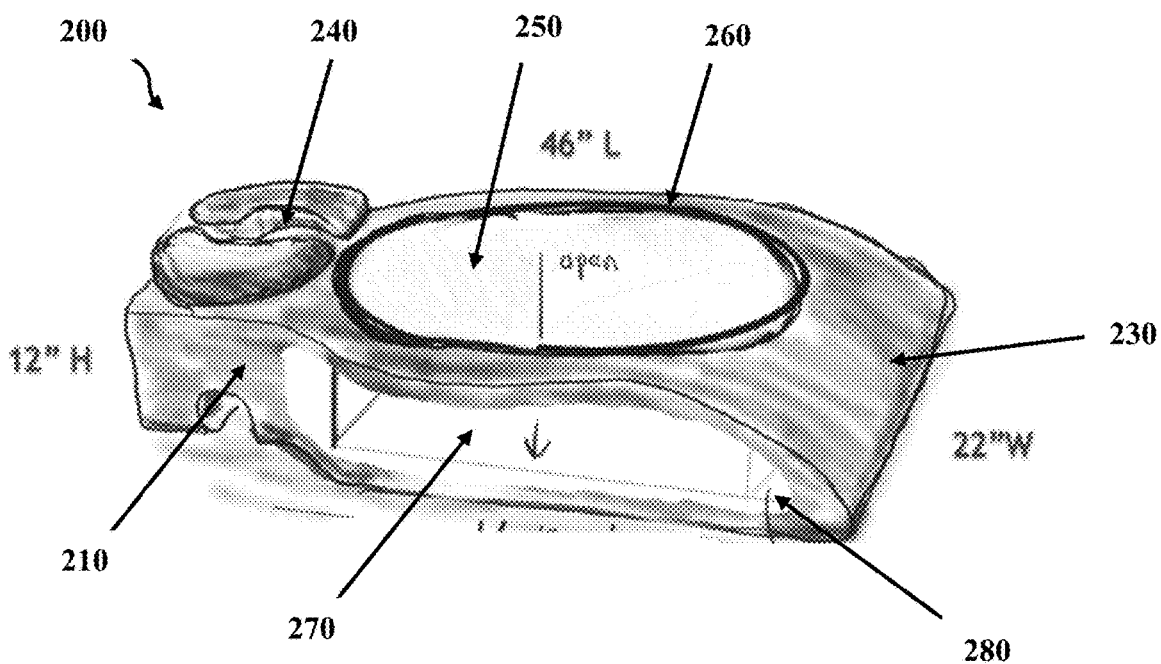
Figure 7B:
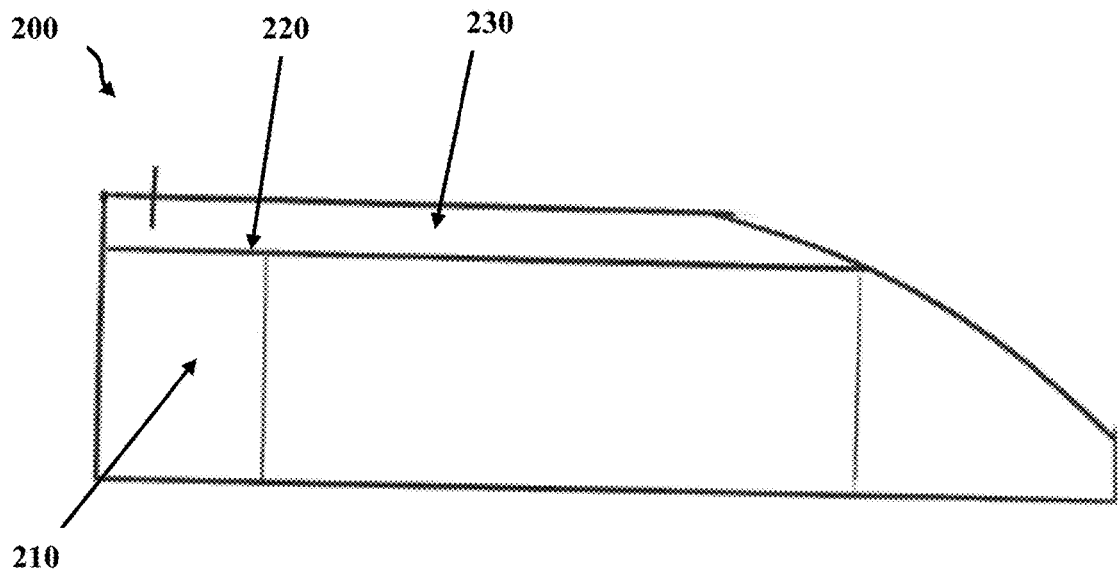

FIGS. 7A-B is a schematic representation of an exemplary respiratory assistance device in one embodiment of the invention. FIG. 7A is a perspective view of an exemplary respiratory assistance device sized to a user. FIG. 7B is a side view of the device of FIG. 7A.

Figure 8:
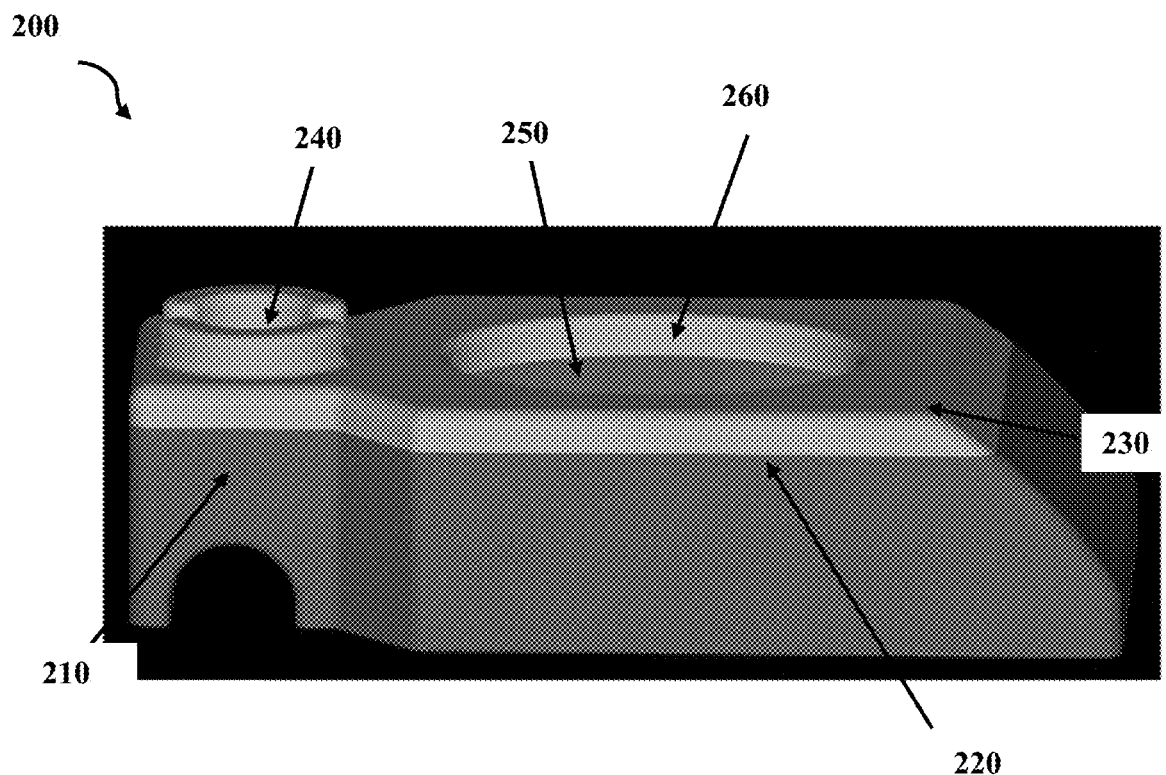

FIG. 8 is a perspective view of an exemplary respiratory assistance device in one embodiment of the invention.

Figure 9:
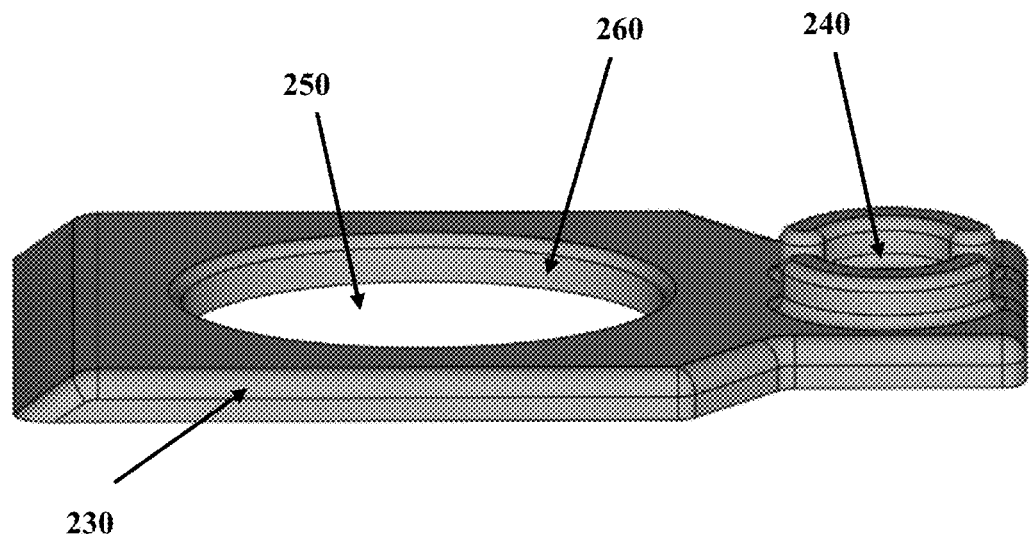

FIG. 9 is a perspective view of a support layer of a respiratory assistance device in one embodiment of the invention. The sizing of the support layer is customized to a user including the size, shape and contour of the first and second openings.

Figure 10A:
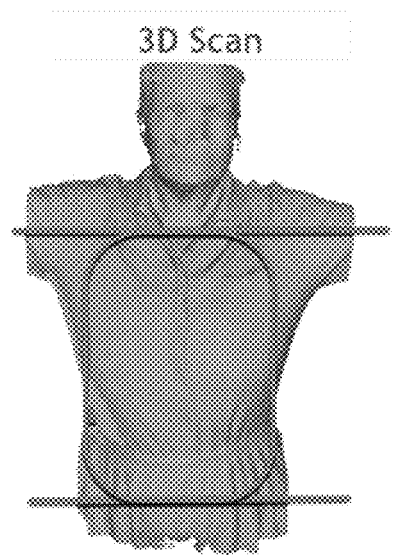
Figure 10B:
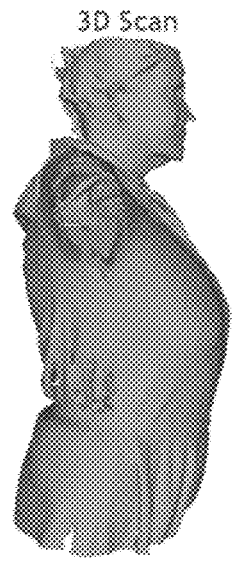
Figure 10C:
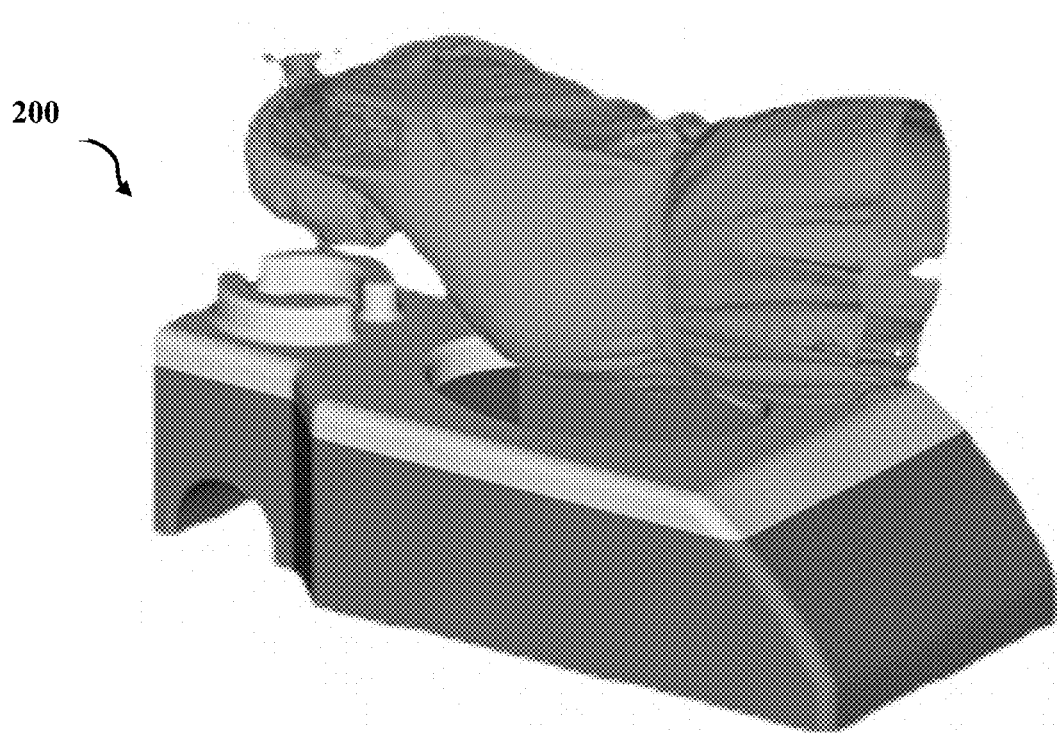

FIGS. 10A-C illustrate the use of 3D scanning to generate a customized respiratory assistance device in one embodiment of the invention. FIG. 10A illustrates the generation of the shape and size (length and width) of a user's abdomen using 3D scanning. FIG. 10B illustrates the generation of the shape and size (depth and contour) of a user's chest and abdomen using 3D scanning. FIG. 10C illustrates the matching of a user's chest and abdomen shape, size, and contour to a customized respiratory assistance device.

Figure 11:
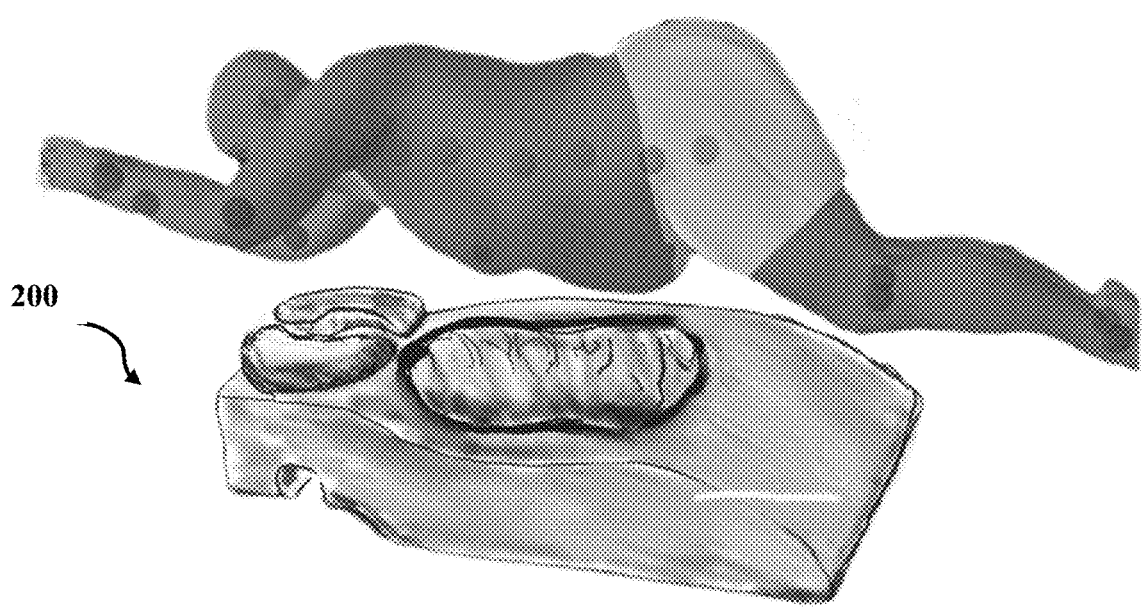

FIG. 11 is a schematic representation of a user being placed on a respiratory assistance device in prone position in one embodiment of the invention.

Figure 12:
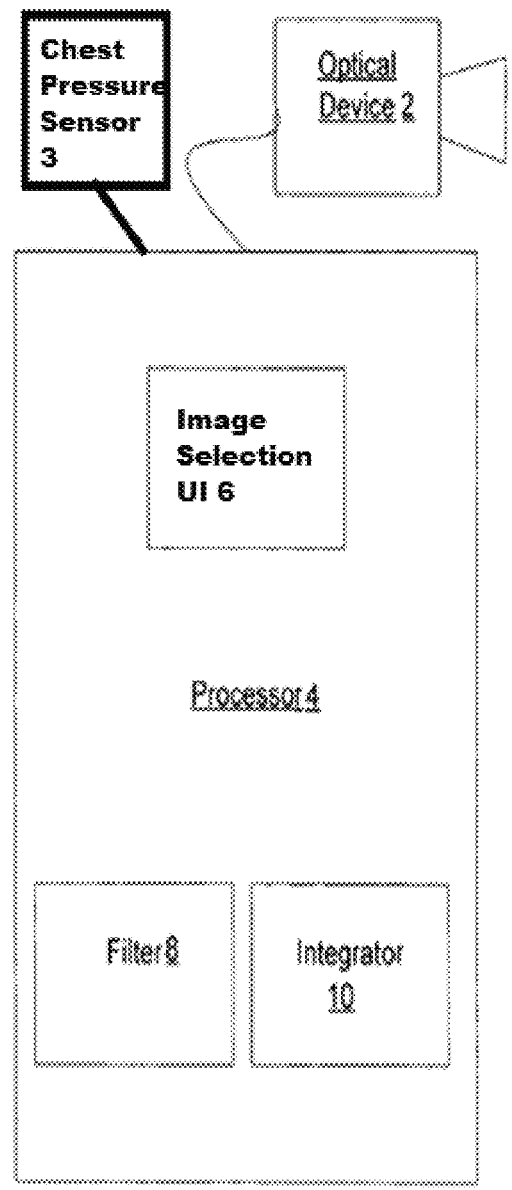

FIG. 12 is a schematic representation of a 3D imaging system in one embodiment of the invention.

Figure 13A:
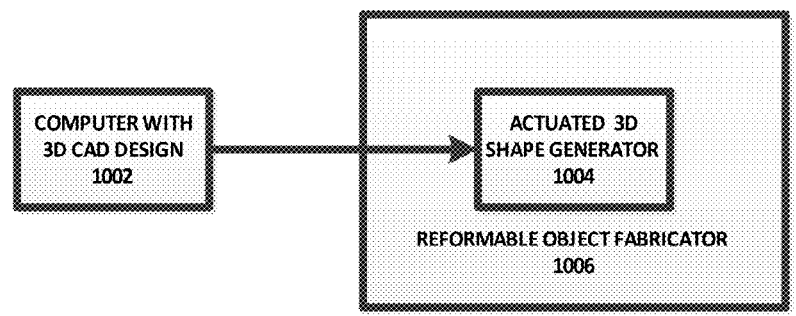
Figure 13B:
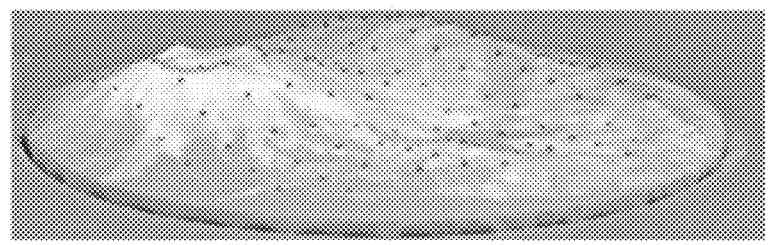
Figure 13C:
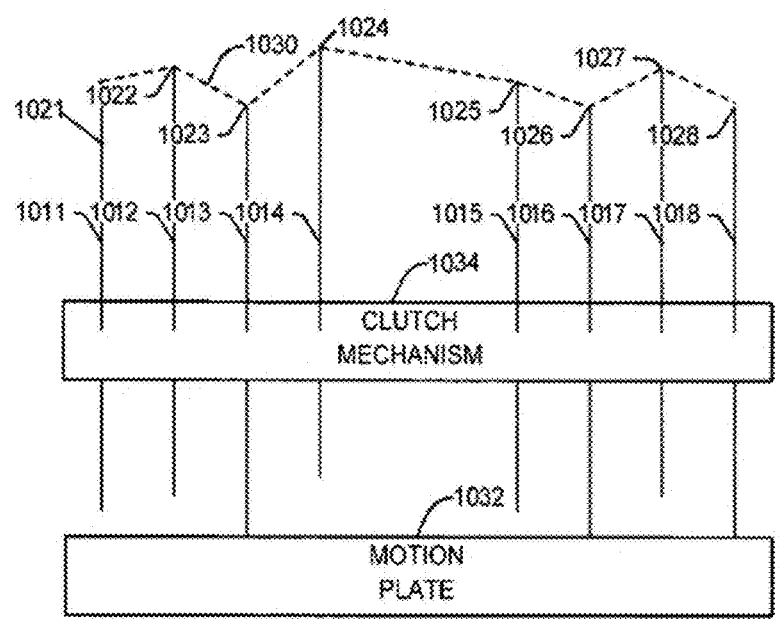
Figure 13D:
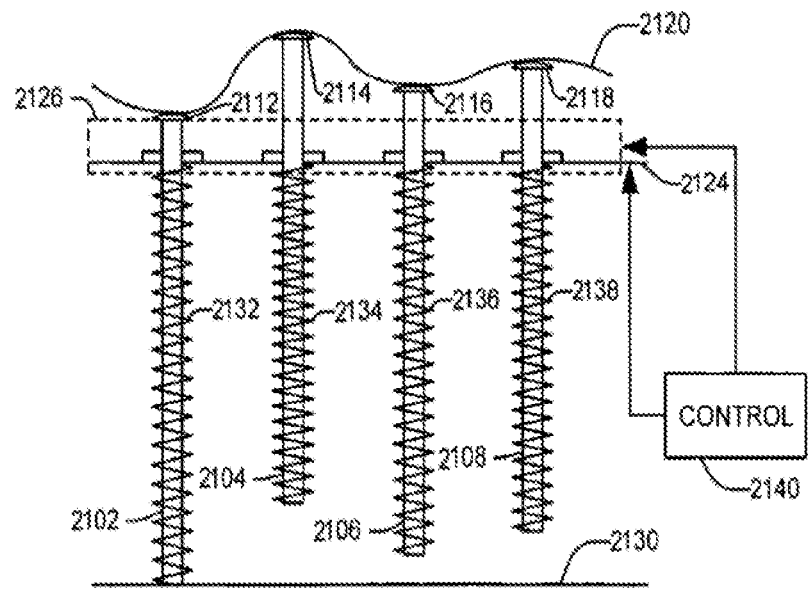

FIGS. 13A-13D illustrate the use of 3D scanning to generate a customized respiratory assistance device in one embodiment of the invention. FIG. 13A illustrates a computer controlled system for fabricating parts. FIG. 13B illustrates use of the system. FIG. 13C illustrates components of the system. FIG. 13D illustrates components of the system.

Figure 14A:
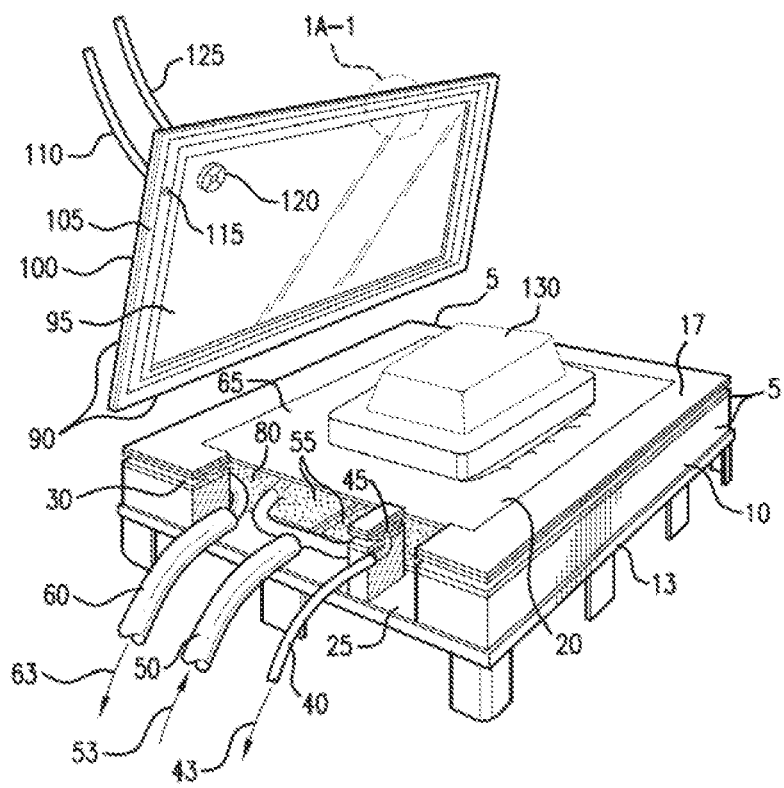
Figure 14B:
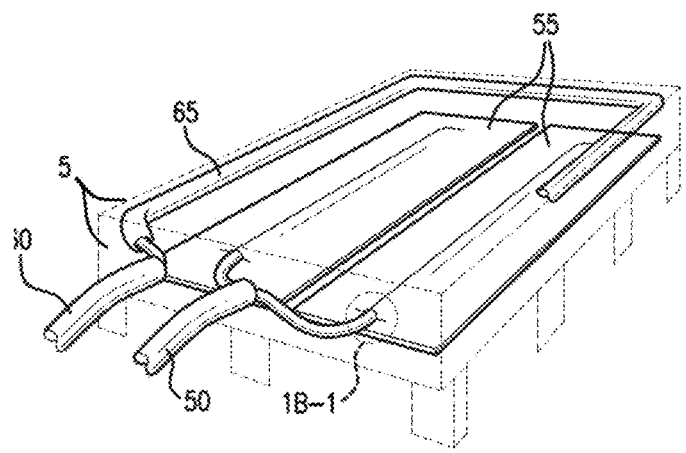
Figure 14C:
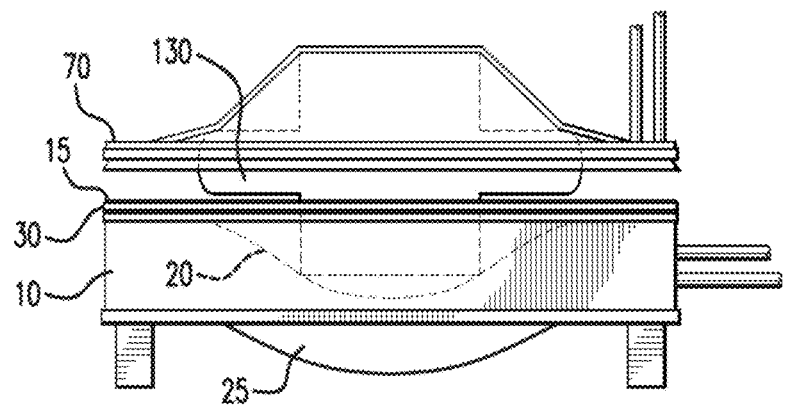
Figure 14D:
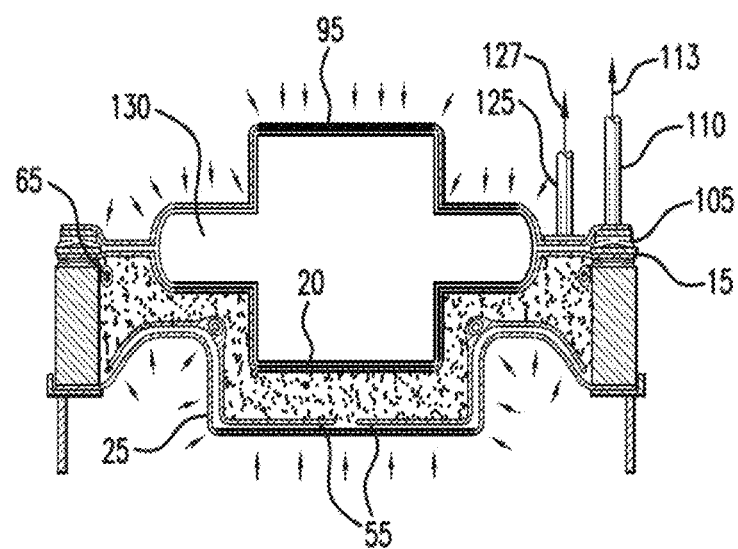

FIGS. 14A-14D illustrate the use of 3D scanning to generate a customized respiratory assistance device in one embodiment of the invention. FIG. 14A illustrates a system for fabricating parts. FIG. 14B illustrates use of the system. FIG. 14C illustrates components of the system. FIG. 14D illustrates components of the system.

DETAILED DESCRIPTION OF THE INVENTION

The present invention is based on the seminal discovery that SARS-CoV-2 induces a sudden rise in hyaluronan levels leading to significant impairment of normal lung function that can be treated by the modulation of hyaluronan levels.

Before the present compositions and methods are described, it is to be understood that this invention is not limited to particular compositions, methods, and experimental conditions described, as such compositions, methods, and conditions may vary. It is also to be understood that the terminology used herein is for purposes of describing particular embodiments only, and is not intended to be limiting, since the scope of the present invention will be limited only in the appended claims.

As used in this specification and the appended claims, the singular forms "a", "an", and "the" include plural references unless the context clearly dictates otherwise. Thus, for example, references to "the method" includes one or more methods, and/or steps of the type described herein which will become apparent to those persons skilled in the art upon reading this disclosure and so forth.

All publications, patents, and patent applications mentioned in this specification are herein incorporated by reference to the same extent as if each individual publication, patent, or patent application was specifically and individually indicated to be incorporated by reference.

Unless defined otherwise, all technical and scientific terms used herein have the same meaning as commonly understood by one of ordinary skill in the art to which this invention belongs. Although any methods and materials similar or equivalent to those described herein can be used in the practice or testing of the invention, it will be understood that modifications and variations are encompassed within the spirit and scope of the instant disclosure. The preferred methods and materials are now described.

COVID-19 induced a sudden rise in hyaluronan levels leading to significant impairment of normal lung function primarily because of rapid excess water accumulation; that hyaluronan is a primary driver of COVID-19 morbidity and mortality due to the rapid accumulation of hyaluronan and thus water into the lungs, resulting in respiratory failure; and that this process can be altered and potentially prevented by that administration of any medication capable of preventing an "Induced Hyaluronan Storm Syndrome". Such medication can include any agent capable of modulating hyaluronan levels directly, for example, a hyaluronic acid synthesis inhibitor or a hyaluronidase, and any agent of capable of modulating hyaluronan levels indirectly, for example by supporting/enhancing a medication that modulates hyaluronan levels directly.

In one embodiment, the present invention provides a method of treating a subject having or at risk of having or having a viral infection including: administering 4-MU (4-methylumbelliferone), PEA (palmitoyl ethanol amide), resveratrol, fisetin, H2, nebulized hyaluronidase or a combination thereof to the subject upon exposure or upon becoming symptomatic or significantly at risk.

The term "subject" as used herein refers to any individual or patient to which the subject methods are performed. Generally, the subject is human, although as will be appreciated by those in the art, the subject may be an animal. Thus, other animals, including vertebrate and primates are included within the definition of subject.

The term "treating" is used herein to refer to both the administration of therapeutic treatments or measures that 1) cure, slow down, lessen symptoms of, and/or halt progression of a diagnosed pathologic conditions or disorder, 2) are prophylactic/preventative measures, or 3) rehabilitation interventions designed to optimize functioning and reduce disability. Those in need of treatment may include individuals already having a particular medical disorder, as well as those who may ultimately acquire the disorder (e.g., those needing preventive measures).

In some aspects, the treatments described herein can be administered to the subject upon becoming symptomatic. By "symptomatic", it is meant that the subject shows, or has developed one or more symptoms of the viral infection. Symptoms of a viral infection may greatly vary depending on the virus responsible for the infection. Non-limiting examples of viral infection symptoms include: fever, chills, muscle or body aches, cough, sore throat, headache, stiff neck, nausea and/or vomiting, rash, sensitivity to light (photophobia), new confusion, shortness of breath or difficulty breathing, fatigue, new loss of taste or smell, congestion or runny nose, diarrhea, trouble breathing or increased respiratory rate, persistent pain or pressure in the chest, inability to wake or stay awake, and bluish lips or face.

The terms "administration of" and or "administering" should be understood to mean providing a pharmaceutical composition in a therapeutically effective amount to the subject in need of treatment. The terms "therapeutically effective amount", "effective dose," "therapeutically effective dose", "effective amount," or the like refer to that amount of the subject compound that will elicit the biological or medical response of a tissue, system, animal or human that is being sought by the researcher, veterinarian, medical doctor or other clinician. Generally, the response is either amelioration of one or more symptoms in a patient or a desired biological outcome (e.g., resolution of the viral infection). Such amount should be sufficient to treat the viral infection and provide relief of its symptoms. The effective amount can be determined as described herein.

4-methylumbelliferone (4-MU), palmitoyl ethanol amide (PEA), fisetin, $H_2$, nebulized hyaluronidase or a combination thereof can be administered to the subject.

4-MU, also known as hymecromone, 7-hydroxy-4-methylcoumarin, 7-Hydroxy-4-methyl-2H-chromen-2-one is a hyaluronan (HA) inhibitor. Hyaluronan content has been found increased approximately 20-fold in the respiratory secretions of COVID-19 patients compared to healthy controls, and hyaluronan found similarly abundant in histologic sections from cadaveric lung tissue from COVID-19 patients. Therefore, HA inhibitor such as 4-MU are useful for the treatment of COVID-19-induced increased levels of hyaluronan. 4-MU has a molecular formula of $C_{10}H_8O_3$, a molecular weight of 176.17 g/mol and a 2D structure of Formula I:

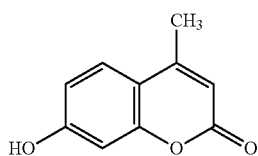

Formula I

4-MU is a hydroxycoumarin that is umbelliferone substituted by a methyl group at position 4. It has a role as an antineoplastic agent and a hyaluronic acid synthesis inhibitor. It derives from an umbelliferone. 4-MU is a substrate for: Liver carboxylesterase 1, Cocaine esterase, and S-formylglutathione hydrolase. Additional details of 4-MU are summarized in Table 1. A HA over production can be controlled with a 4-MU medication, which inhibits HA site of production on the cell membrane. 4-MU can affect various genes such as HYAL1-HYAL4, among others. HYAL1 gene encodes a lysosomal hyaluronidase. To suppress the production of HA, 4-MU can be administered to COVID-19 patient, to inhibit the three isoenzymes of hyaluronan synthase-HAS-1, HAS-2, and HAS-3 concurrently.

TABLE 1

4-MU Characteristics.

| Property Name | Property Value |
| --- | --- |
| Molecular Weight | 176.17 g/mol |
| XLogP3 | 1.9 |

TABLE 1-continued

4-MU Characteristics.

| Property Name | Property Value |
| --- | --- |
| Hydrogen Bond Donor Count | 1 |
| Hydrogen Bond Acceptor Count | 3 |
| Rotatable Bond Count | 0 |
| Exact Mass | 176.047344 g/mol |
| Monoisotopic Mass | 176.047344 g/mol |
| Topological Polar Surface Area | 46.5 Å$^2$ |
| Heavy Atom Count | 13 |
| Formal Charge | 0 |
| Complexity | 257 |
| Isotope Atom Count | 0 |
| Defined Atom Stereocenter Count | 0 |
| Undefined Atom Stereocenter Count | 0 |
| Defined Bond Stereocenter Count | 0 |
| Undefined Bond Stereocenter Count | 0 |
| Covalently Bonded Unit Count | 1 |
| Compound Is Canonicalized | Yes |

Palmitoyl Ethanol Amide, palmitoylethanolamide or PEA, is an endogenous anti-inflammatory compound and PPAR alpha and gamma agonist, available as food supplement. PEA reduces mortality induced by various microorganisms inoculation, modulates 'cytokine storm', and reduces the secretion of pro-inflammatory proteins such as NGF, CXCL1, IL-1β, IL-6 and TNF-alpha. PEA also inhibits iNOS expression and nuclear NF-κ B translocation, overactive mast cells, which play a role in the pathogenesis of the 'cytokine storm'. Furthermore, PEA was found effective and safe in the prophylaxis and treatment of influenza and respiratory tract infections.

In one aspect, PEA can be used, for example, in the context of a viral infection caused by a SARS-CoV-2. In such case, PEA can be used to: (i) prevent viral infection caused by COVID-19, for example, when taken prior to infection; (ii) address the induced hyaluronic acid storm (IHS) syndrome caused by COVID-19 by modulating macro-phage and lymphocyte activation and action shifting from proinflammatory M1 state to pro-resolving M2 state; (iii) reduce or shorten symptoms of COVID-19.

PEA can be administered in doses ranging from 200-800 mg taken three times a day when started at the first sign of infection. PEA can also be administered in doses ranging from 200-800 mg taken three times a day prophylactically. The bioavailability of PEA can be improved upon complexing of PEA with an additional compound that enhances or complements the action of PEA. For example, the bioavailability of PEA can be improved by complexing it with cyclodextrin, 4-MU, hyaluronidase or with lipids.

PEA can be used alone or combined with 4-MU, resveratrol, fisetin and/or hyaluronidase, for example, prior to any-exposure to a virus (such as SARS-CoV-2), at the time of diagnosis, or after infection. For example, PEA can be used to reduce the risk of infection with the virus; to reduce the symptoms if infection occurs and reduce the risk of IHS in normal and high-risk patients better than either drug alone; and to reduce the symptoms and reduce and shorten the duration of symptoms and the risk of IHS in normal and high risk patients better than either drug alone.

PEA can be administered in combination with a complimentary compound, for example to improve its bioavailability. For example, PEA can be administered in combination with a polyphenol such as fisetin.

Fisetin is a polyphenol with a number of anti-inflammatory, antiviral, senolytic, and anti-cancer properties. In addition, it is a potent inhibitor of hyaluronan and related hyaluronan pathways and is effective at doses 10 times lower than 4-MU. It has been shown to powerfully suppress the expression of T(H)2-type cytokines (IL-4, IL-13, and IL-5) by basophils and has been effective in models of ovalbumin-induced asthma through inhibition of NF-κB activity. IL-13 has been shown to have a central role in COVID-19 pathology and specifically drives hyaluronan production, a fundamental and broad based activator to the innate immune system.

In some aspects, PEA is co-administered with fisetin. In one aspect, the combination of PEA and fisetin provides a synergistic benefit to treating viral infection and/or viral infection related disorders (e.g., COVID-19 and/or related disorders).

In some aspects, PEA is co-administered with resveratrol.

In some aspects, PEA is co-administered with fisetin and/or resveratrol.

In some aspects, dosing of fisetin is 1-20 mg/kg/day. Typically 100 mg/day combined with PEA and/or 4-MU in early COVID-19. In acute respiratory distress it can be combined with nebulized inhaled hyaluronidase at a preferred initial dose of 500 mg to 1500 mg for two days and then 100 mg/day. In post-acute COVID-19 or "Long COVID-19" preferred dosing is 100 mg one to three times a day, or 500 mg daily. It is anticipated that following liver function will be helpful to assess the method.

In Long COVID-19 serial CT scan and lung diffusing capacity for nitric oxide ($DL_{NO}$) can be used to evaluate the benefit of the method as can more standard pulmonary function testing or measurement of exercise tolerance.

The bioavailability of fisetin can be improved by formulation with sulfobutylether-β-cyclodextrin (SBE-β-CD) into an inhalable powder for nebulization via spray drying of fisetin-SBE-β-CD complex solution in the presence of ethanol producing a dry powder with improved aerosolization properties. When delivered from a dry powder inhaler, a 2-fold increase in the fine particle fraction (FPF) can occur compared to the powder produced from a complex solution containing water alone.

Bioavailability can be additional improved in the method by combining fisetin with specific oils, surfactant, and co-surfactant making self-nano emulsifying drug delivery system (SNEDDS). An example would be a liquid SNEDDS formulation consisting of castor oil (0.1 mL), Lauroglycol FCC (0.1 mL), tween 80 (0.4 mL) and Transcutol P (0.6 mL). These components were added into a clean glass vial in required quantities and mixed uniformly. Then, Fisetin (5 mg) is dissolved in the above mixture in order to make SNEDDS of fisetin as known in the art.

In some aspects, PEA is administered with, or without 4-MU and/or fisetin, and 100 mg of trans resveratrol complex with sulfobutylether-β-cyclodextrin (SBE-β-CD) or other cyclodextrins or in a liquid SNEDDS formulation.

In some aspects, the treatment methodology of the present invention is beneficial in inhibition of the activation and trafficking of dendritic cells.

As discussed herein, dendritic cells are a subset of mononuclear cells that are a critical part of the innate immune system. The cells play a central role in the dysregulated response to the SARS-CoV-2. Their activation and function in the lung is specifically mediated by 4-MU and fisetin and in certain aspects such actives therapeutically block this activation by disruption of hyaluronan synthesis, turnover, and receptor interactions. Further, HA on the surface of dendritic cells and the CD44 molecule that anchors the HA mediates the active uptake and transport of dendritic cells into the lymphatic collecting vessels and thus into lymph nodes for processing. Thus 4-MU and fisetin specifically modulates and reduces the immune hyper reaction in the lungs and other organs in response to SAR-COV2 infection.

In some aspects, the treatment methodology of the present invention is beneficial in treatment and inhibition of lung inflammation and pulmonary fibrosis.

Tissue fibrosis is a common sequela of viral infection, commonly seen in such wide-ranging pathogens as H1N1 viral pneumonia, HIV, and Hepatitis C, and has been a feared potential complication of SARS-CoV2. Autopsy reports are emerging of extensive pulmonary fibrosis in COVID-19 victims months after initial infection, and multiple emergency "rescue" lung transplants in acute patients with marked ARDS have occurred with evidence of extensive fibrosis in the explanted lungs.

HA is a critical regulator of pulmonary fibrosis. Over expression of HAS2 increases HA production and promotes an invasive phenotype in fibroblasts. IL-13 has been shown to be increased in severe COVID-19 patients along with elevated levels of hyaluronan in the lungs and serum. Blockage of IL-13 leads to a reduction of HAS1 productions and hyaluronan levels in SARs-COV-2 infected mice models.

Transforming growth factor beta (TGF-β) directed transitional conversion of fibroblasts to the myofibroblastic phenotype is required for wound contraction, collagen deposition, fibrosis and scar formation. Endogenous synthesis of HA is required for myofibroblast conversion. Alveolar and tissue macrophages, alveolar epithelial cells, alveolar type II epithelial cells, and eosinophils are important sites of TGF-β1 production and TGF-β1 is found to be localized in in the lung of patients with asthma and idiopathic pulmonary fibrosis.

IL-13 powerfully stimulates the production of TGF-β1 and is implicate not only in COVID-19 but also in human asthma. Fisetin has been shown to reduce IL-4 and the related IL-13 in a number of models. Fisetin at a dose of 100 μmol/kg bodyweight in a mouse model of LPS-induced acute pulmonary inflammation significantly reduced numerous measures of inflammation and the anti-inflammatory effects of fisetin was more pronounced than dexamethasone.

As such, the invention includes administration of fisetin as an agent to prevent or treat pulmonary fibrosis, as well as to modulate HA to treat SARS-COV-2 viral transmission and virulence via disruption of filopodia and dendritic cell activation and trafficking and hyaluronan associated ARDS.

Molecular hydrogen or $H_2$, is an inert gas, that reacts with strong oxidants such as hydroxyl radical in cells, which suggests it has potential for preventive and therapeutic applications. $H_2$ rapidly diffuses into tissues and cells, and neither disturbs metabolic redox reactions nor affects signaling reactive oxygen species; therefore, having no to little adverse effects. $H_2$ can be ingested or consumed by inhaling $H_2$ gas, drinking $H_2$-dissolved water ($H_2$-water), injecting $H_2$-dissolved saline ($H_2$-saline), taking an $H_2$ bath, or dropping $H_2$-saline into the eyes. $H_2$ reduces oxidative stress not only by direct reactions with strong oxidants, but also indirectly by regulating various gene expressions, therefore regulating anti-inflammatory and anti-apoptotic pathways, and enhancing energy metabolism.

Molecular hydrogen has been shown to be effective in a number is disease states such an Alzheimer's disease and Parkinson's disease as well. Molecular hydrogen has been shown in both animal and human studies to be essentially harmless and can be administered orally in water, inhaled, and via intravenous. In one aspect, $H_2$ can be used, for example, in the context of a viral infection caused by a SARS-CoV-2. In such case, $H_2$ can be used to: (i) treat COVID-19 infection and IHS; and (ii) treat the inflammation and injury caused by COVID induced IHS.

COVID-19 is characterized by elevated ferritin levels. In hypoxic conditions, ferritin interacts with xanthine oxidase to release free iron. Via the Fenton reaction this free iron leads to the production of highly reactive hydroxyl radicals. These particularly reactive oxygen species (ROS) can cause significant tissue damage and can lead to the fragmentation of HA into more inflammatory small molecular weight particles. $H_2$ neutralizes the hydroxyl radical.

$H_2$ can be administered as fortified or enriched standard I.V solutions such as D5NS, Ringer Lactate or other such solutions as are commonly used to support critical ill patients.

Hyaluronidases are a family of enzymes that catalyze the degradation of hyaluronic acid (HA). The three main types of hyaluronidases are two classes of eukaryotic endoglycosidase hydrolases and a prokaryotic lyase-type of glycosidase. In humans, there are five functional hyaluronidases: HYAL1, HYAL2, HYAL3, HYAL4 and HYAL5 (also known as SPAM1 or PH-20); plus a pseudogene, HYAL6 (also known as HYALP1). HA fragments resulting from the enzymatic activity can be of variable size are then further hydrolyzed by HYAL1 after being internalized into endolysosomes to generates HA oligosaccharide.

Hyaluronidases intracellularly degrade hyaluronan, one of the major glycosaminoglycans of the extracellular matrix. Hyaluronan is thought to be involved in cell proliferation, migration and differentiation. HYAL1 is active at an acidic pH and is the major hyaluronidase in plasma. Mutations in this gene are associated with mucopolysaccharidosis type IX, or hyaluronidase deficiency. The gene is one of several related genes in a region of chromosome 3p21.3 associated with tumor suppression. Multiple transcript variants encoding different isoforms have been found for this gene. HYAL1 was first purified from human plasma and urine and the enzyme is 435 amino acids long with a molecular weight of 55-60 kDa. The enzyme is composed of two closely associated domains: a N-terminal catalytic domain (Phe22-Thr352) and a smaller C-terminal domain (Ser353-Trp435). The catalytic domain adopts a distorted $(\beta/\alpha)\beta$ barrel fold similar to that of bee venom hyaluronidase. Within the catalytic domain, residues such as Tyr247, Asp129, Glu131, Asn350, and Tyr202 play important roles in the cleavage of the $\beta1\rightarrow4$ linkage between N-acetylglucosamine and glucuronic acid units in hyaluronan. HYAL1 is responsible for the hydrolysis of intracellular hyaluronan of all sizes into fragments as small as tetrasaccharides. In the optimal pH state of 4.0, Asp129 and Glu131 share a proton. Intermolecular resonance in the amide bond in the N-acetylglucosamine unit of the bound hyaluronan polymer leads to a transition state with a positive charge on the nitrogen and an oxyanion nucleophile, which is stabilized by hydrogen bond interactions with Tyr247, that can perform an intramolecular attack on the electrophilic carbon. This attack forms a 5-membered ring that is stabilized by the negative charge of Asp129 that forms as the leaving hydroxyl group of the glucuronic acid unit takes the proton from Glu131. The now negatively charged Glu131 is primed to activate a water molecule for the hydrolysis of the intermolecular ring intermediate to restore N-acetylglucosamine. Tyr202 and Asn350, while not directly involved in the $f1\rightarrow4$ linkage cleavage, were identified to be important to HYAL1 function. HYAL1 uses Tyr202 as a substrate binding determinant and also requires proper glycosylation of Asn350 for full enzymatic function. The optimal pH range for HYAL1 function is 4.0 to 4.3, though HYAL1 is still 50-80% active at pH 4.5.

Hyaluronidase-2 is an enzyme that in humans is encoded by the HYAL2 gene, which gene encodes a protein which is similar in structure to hyaluronidases. Hyaluronidase-3 is an enzyme that in humans is encoded by the HYAL3 gene. This gene encodes a protein which is similar in structure to hyaluronidases. However, this protein has not yet been shown to have hyaluronidase activity. The gene is one of several related genes in a region of chromosome 3p21.3 associated with tumor suppression.

A HA over production can be controlled with a medication comprising one or more hyaluronidases, which degrade excessive HA. Hyaluronidases can be administered for example, in the form of nebulized hyaluronidase.

In some aspects, a combination of 4-MU, PEA, resveratrol, fisetin, $H_2$, and/or hyaluronidase can be administered to a subject. The phrases "combination therapy", "combined with" and the like refer to the use of more than one medication or treatment simultaneously to increase the response. The treatments of the present invention might for example be used alone or in combination with one another to treat the viral infection. Specifically, the administration of 4-MU to a subject can be in combination with PEA, resveratrol, fisetin, $H_2$, and/or hyaluronidase. Any additional therapies can be administered prior to, simultaneously with, or following administration of the initial therapy of the present invention.

For example, in one aspect, a method of treating a viral infection includes providing 4-MU to a subject. The 4-MU treatment should reduce Staphylococcal enterotoxin B (SEB)-induced lung permeability and reduced cytokine production. 4-MU treatment can be an over the-counter product such as Cantabilin® (hymecromone Tablets).

In another aspect, a method of treating a viral infection includes providing hyaluronidase to a subject. In an additional aspect, a method of treating a viral infection includes providing PEA to a subject. In yet another aspect, a method of treating a viral infection includes providing $H_2$ to a subject. In another aspect, a method of treating a viral infection includes providing PEA and fisetin to a subject In some aspects, a treatment with 4-MU can be combined with PEA, fisetin, and/or resveratrol. In other aspects, a treatment with 4-MU can be combined with hyaluronidase. In additional aspects, a treatment with 4-MU can be combined with $H_2$.

In other aspects, a method of treating a viral infection includes providing $H_2$, together with 4-MU or PEA or fisetin and/or resveratrol, to a subject.

The treatment described herein can be administered by several routes; and each individual treatment can be administered by its own most appropriate route. Administration routes can be enteral, topical, by inhalation or parenteral. As such, administration routes include but are not limited to intracutaneous, subcutaneous, intravenous, intraperitoneal, intraarterial, intrathecal, intracapsular, intraorbital, intracardiac, intradermal, transdermal, transtracheal, subcuticular, intraarticulare, subcapsular, subarachnoid, intraspinal and intrasternal, oral, sublingual buccal, rectal, vaginal, nasal ocular administrations, as well infusion, inhalation, and nebulization. The phrases "parenteral administration" and "administered parenterally" as used herein means modes of administration other than enteral and topical administration.

In one aspect, administration is by an oral, intravenous, intraperitoneal, intraarterial, sublingual, or nasal route or by infusion, inhalation, or nebulization.

The pharmaceutical compositions can be administered in a variety of unit dosage forms depending upon the method of administration, and the drug to be administered. Suitable unit dosage forms, include, but are not limited to powders, tablets, pills, capsules, lozenges, suppositories, patches, nasal sprays, injectables, implantable sustained-release formulations, lipid complexes, etc.

In some aspects, the 4-MU is administered by tablet, capsule or liquid dosage form.

The treatment described herein can be administered at various dose, including an effective amount an active agent, referring to an amount that is non-toxic to a subject or a majority or normal cells, but that is sufficient to provide a desired effect (e.g., treatment of a viral infection). This amount may vary from subject to subject, depending on the species, age, and physical condition of the subject, the severity of the disease that is being treated, the particular conjugate, or more specifically, the particular active agent used, its mode of administration, and the like. Therefore, it is difficult to generalize an exact "effective amount," yet, a suitable effective amount may be determined by one of ordinary skill in the art.

In one aspect, the subject is administered from about 400 mg to 4800 mg per day of 4-MU, PEA, fisetin, and/or resveratrol.

For example, the subject can be administered the drug at about 400 mg, 500 mg, 600 mg, 700 mg, 800 mg, 900 mg, 1000 mg, 1100 mg, 1200 mg, 1300 mg, 1400 mg, 1500 mg, 1600 mg, 1700 mg, 1800 mg, 1900 mg, 2000 mg, 2100 mg, 2200 mg, 2300 mg, 2400 mg, 2500 mg, 2600 mg, 2700 mg, 2800 mg, 2900 mg, 3000 mg, 3100 mg, 3200 mg, 3300 mg, 3400 mg, 3500 mg, 3600 mg, 3700 mg, 3800 mg, 3900 mg, 4000 mg, 4100 mg, 4200 mg, 4300 mg, 4400 mg, 4500 mg, 4600 mg, 4700 mg, 4800 mg per day.

In one aspect, the day dose is administered in one or more dose throughout the day. For example, a daily dose can be administered in 1, 2, 3, 4, or more doses, spread out in time during the day, but such that the total dose received does not exceed the daily dose. For example, a subject can be administered about 800 mg per day in one dose of about 800 mg, in two doses of about 400 mg, 3 doses of about 266 mg, 4 doses of about 200 mg, etc.

In some aspects, the subject is administered about 800 mg to 4000 mg per day of drug. In other aspects, the subject is administered about 800 mg to 2400 mg per day of drug, or 800 mg, three times per day.

In one aspect, external non-invasive negative, positive or biphasic pressure breathing assistance is further provided to the subject optionally using a breathing assistance device of the present invention.

As used herein, the term "breathing assistance device" is used interchangeably with the term "portable breathing assistance device."

In order to further assist a subject with breathing difficulties, external negative pressure ventilation can be used. Humans, like most mammals, breathe by negative pressure breathing: the rib cage expands and the diaphragm contracts, expanding the chest cavity. This causes the pressure in the chest cavity to decrease, and the lungs expand to fill the space. This, in turn, causes the pressure of the air inside the lungs to decrease (it becomes negative, relative to the atmosphere), and air flows into the lungs from the atmosphere: inhalation. When the diaphragm relaxes, the reverse happens and the person exhales. In subject affected by severe respiratory illness, such as those caused by viral infection, fluids cause the lungs to become stiffened and part or all of the ability to control the muscles involved can be lost, causing breathing to become difficult or impossible. In addition, viral infections such as COVID-19 have been shown to inflame and disrupt key brainstem arousal nuclei and respiratory drive and rhythm generation centers adding to the respiratory failure and the need for mechanical support. To assist the patient, an iron lung or the Drinker respirator can be used. It is powered by an electric motor with air pumps from two vacuum cleaners. The air pumps changed the pressure inside an airtight box, pulling air in and out of the lungs. Other mechanical means such as activation of a bellows like device applied to the chest and abdomen can also be used apply negative pressure to the lungs.

In some aspect, the breathing assistance is provided by a mechanical ventilation assistance device, such as a breathing assistance device of the present invention.

In various aspects, other ventilators or breathing assistance devices can be used to perform the treatment methodology of the invention. In one example, extracorporeal membrane oxygenation (ECMO), also known as extracorporeal life support, can be used to assist the patient in breathing. ECMO is an extracorporeal technique of providing prolonged cardiac and respiratory support to persons whose heart and lungs are unable to provide an adequate amount of gas exchange or perfusion to sustain life. In another example, the "Iron Lung" can be used where the patient is placed into a large steel chamber that forms a sealed, air-tight compartment around the patient's entire body with just their head outside the iron long as pumps periodically decrease and increase the air pressure within the chamber to cause the lungs to fill with or expel air to mimic the physiological action of breathing.

Other ventilators such as pulmonary expansion devices can be used that cover specific lung fields and abdominal cavity and may generate negative pressure fields locally. The device also may provide percussion therapy for air-way clearance. The device may generate a localized negative pressure field non-invasively to the exterior of the chest wall and abdomen, thereby increasing the total lung capacity (TLC), functional reserve capacity (FRC), and residual volume (RV) in underlying lung fields. For example, in obese individuals such as many COVID-19 patients, there is a loss of both chest and abdominal movement. The portable emergency respiratory assistance device can address this by design to allow for optimized chest and abdominal movement. As a result, increased ventilation and perfusion to the targeted internal lung field may be achieved by creating a decrease in the external barometric pressure relative to the more positive intrinsic airway pressures. Once a targeted functional residual capacity has been established, percussion may be applied with increased effectiveness due to greater oscillatory movement of chest wall.

In one aspect, the viral infection is a coronavirus infection.

Coronaviruses are a group of RNA viruses that cause diseases in mammals and birds. In humans and birds, they cause respiratory tract infections that can range from mild to lethal. Mild illnesses in humans include some cases of the common cold, while more lethal varieties can cause SARS, MERS, and COVID-19.

Coronaviruses constitute the subfamily Orthocoronavirinae, in the family Coronaviridae, order Nidovirales, and realm Riboviria. They are enveloped viruses with a positive-sense single-stranded RNA genome and a nucleocapsid of helical symmetry. The genome size of coronaviruses ranges from approximately 26 to 32 kilobases, one of the largest among RNA viruses. They have characteristic club-shaped spikes that project from their surface, which in electron micrographs create an image reminiscent of the solar corona, from which their name derives.

Coronaviruses vary significantly in risk factor. Some can kill more than 30% of those infected, such as MERS-CoV, and some are relatively harmless, such as the common cold. Coronaviruses can cause colds with major symptoms, such as fever, and a sore throat from swollen adenoids. Coronaviruses can cause pneumonia (either direct viral pneumonia or secondary bacterial pneumonia) and bronchitis (either direct viral bronchitis or secondary bacterial bronchitis). The human coronavirus discovered in 2003, SARS-CoV, which causes severe acute respiratory syndrome (SARS), has a unique pathogenesis because it causes both upper and lower respiratory tract infections.

Six species of human coronaviruses are known, with one species subdivided into two different strains, making seven strains of human coronaviruses altogether. The four human coronaviruses that produce symptoms that are generally mild include Human coronavirus OC43 (HCoV-OC43), β-CoV; Human coronavirus HKU1 (HCoV-HKU1), β-CoV; Human coronavirus 229E (HCoV-229E), α-CoV; and Human coronavirus NL63 (HCoV-NL63), α-CoV. The three human coronaviruses that produce symptoms that are potentially severe include Middle East respiratory syndrome-related coronavirus (MERS-CoV), β-CoV; Severe acute respiratory syndrome coronavirus (SARS-CoV), β-CoV; and Severe acute respiratory syndrome coronavirus 2 (SARS-CoV-2), β-CoV.

The viral infection described herein can be caused by any coronavirus. In some aspects, the coronavirus is SARS-CoV-2.

Severe acute respiratory syndrome coronavirus 2 (SARS-CoV-2) is the strain of coronavirus that causes coronavirus disease 2019 (COVID-19), the respiratory illness responsible for the COVID-19 pandemic, an outbreak declared by the World Health Organization a Public Health Emergency of International Concern on 30 Jan. 2020, and a pandemic on 11 Mar. 2020.

SARS-CoV-2 is a Baltimore class IV positive-sense single-stranded RNA virus that is contagious in humans. As described by the U.S. National Institutes of Health, it is the successor to SARS-CoV-1, the strain that caused the 2002-2004 SARS outbreak.

Taxonomically, SARS-CoV-2 is a strain of severe acute respiratory syndrome-related coronavirus (SARSr-CoV). It is believed to have zoonotic origins and has close genetic similarity to bat coronaviruses, suggesting it emerged from a bat-borne virus. The virus shows little genetic diversity, indicating that the spillover event introducing SARS-CoV-2 to humans is likely to have occurred in late 2019. The virus mainly enters human cells by binding to the receptor angiotensin converting enzyme 2 (ACE2).

In some aspects, administering 4-MU, PEA, resveratrol, fisetin, $H_2$, nebulized hyaluronidase or any combination thereof treats, blocks and/or disrupts virus-associated membrane trafficking and/or filopodia, infectivity, virulence, and/or spread.

By "virus infectivity, virulence and/or spread" it is meant that both the propagation of the coronavirus in a subject from one infected cell to a non-infected cell and the propagation of the coronavirus from an infected subject to a non-infected subject can be inhibited.

As used herein, the term "membrane trafficking" encompasses a wide variety of processes that go into the movement of cargo (typically proteins, pathogens and other macromolecules) using membrane bound transport vesicles. This transport can take place within different organelles in the same cell, or across the cell membrane to and from the extracellular environment.

Membrane trafficking can be divided into two basic pathways based on the direction of travel, exocytosis and endocytosis. Exocytosis refers to the movement of cargo to the plasma membrane or out of the cell. As part of the biosynthetic-secretory pathway, newly synthesized proteins, lipids or carbohydrates move from the endoplasmic reticulum (ER) via the Golgi to the cell membrane or extracellular space. Conversely, endocytosis is the movement of cargo into the cell from the plasma membrane. This can be often used for the uptake of nutrients which cannot be synthesized by the cell, such as vitamins, cholesterol and iron. Another important function of the endocytic pathway is to direct cargo for recycling or degradation via autophagy. The cell can also use large scale endocytic mechanisms such as phagocytosis and macropinocytosis to internalize pathogens and external particles in order to maintain an immune response.

During coronavirus infection, dendritic cells are subjected to activation and membrane trafficking. Dendritic cells are a subset of mononuclear cells that are a critical part of the innate immune system. For example, they play a central role in the dysregulated response to the SARs COV-2 virus. Their function in the lung is specifically mediated by hyaluronan.

Filopodia are thin, actin rich bundles protruding from cell plasma membranes, serving physiological purposes, such as probing the environment and facilitating cell-to-cell adhesion. Actively polymerized filopodial-protrusions are exploited during virus entry, trafficking, spread, and the development of clinical pathology of viral diseases. For example, filopodia can provide unique opportunities for many viruses to invade host cells vertically during primary infection, or horizontally during virus spread from cell-to-cell. These can explain the unprecedented ability of viruses to invade both nearby and long-distant host cells, a feature that may directly contribute to viral tropism.

In other aspects, the subject is further positioned in prone position on a respiratory assistance device as described herein, also referred to herein as PENPRAD.

In another embodiment, the invention provides a method of inhibiting a coronavirus infectivity, virulence and/or spread in a subject including inhibiting coronavirus-associated membrane trafficking and/or filopodia, wherein inhibiting coronavirus-associated membrane trafficking and/or filopodia includes administering to the subject having or at risk of having a coronavirus infection 4-methylumbelliferone (4-MU), resveratrol, palmitoylethanolamide (PEA), fisetin and/or nebulized hyaluronidase, upon exposure or upon becoming symptomatic, thereby inhibiting a coronavirus infectivity, virulence and/or spread.

As used herein "upon becoming symptomatic" refers to the ability of the methods described herein to protect infected and symptomatic patients. "Upon exposure" refers to the ability of the methods described herein to prevent infection and therefore the development of symptoms and/or of the disease of exposed subjects. As used herein, "exposed subject" can include both subjects that are at high risk of infection by virtue of known or suspected association or exposure with infected persons and subjects that are at high risk of infection by virtue of exposure to high-risk environments. In one aspect, the coronavirus is SARS-CoV-2.

In another embodiment, the invention provides a method of treating a subject having a coronavirus infection including: a) positioning the subject in prone position on the respiratory assistance device described herein, or a customized respiratory assistance device generated by the method described herein; and b) delivering 4-methylumbelliferone (4-MU), palmitoylethanolamide (PEA), resveratrol, fisetin, $H_2$, nebulized hyaluronidase, or any combination thereof, to the subject via the breathing device, thereby treating the coronavirus infection in the subject.

In one aspect, administering 4-MU, PEA, resveratrol, fisetin, H2, nebulized hyaluronidase or any combination thereof treats, blocks and/or disrupts virus-associated membrane trafficking, filopodia, infectivity, virulence, and/or spread.

In another aspect, positioning the subject on the respiratory assistance device releases pressure off the diaphragm, lungs and blood vessels and improves perfusion, lymphatic circulation, cardiovascular function and/or brain function.

In various aspects, PEA and fisetin are co-delivering to the subject.

In various aspects, PEA and fisetin are co-delivering to the subject.

In various aspects, PEA and 4-MU are co-delivering to the subject.

In various aspects, PEA and/or resveratrol and/or 4-MU and/or fisetin are co-delivering to the subject.

In another embodiment, the invention provides a respiratory assistance device. In various aspects, the device may be portable and configured to provide emergency negative pressure breathing assistance.

In some embodiments, device is designed to provide emergency respiration assistance to COVID-19 and related IHS victims, as well as others. In various embodiments, the device includes a surface with supporting structures or opening for the face, shoulders, arms, chest, and abdomen with appropriate padding. The surface can include an inclined or curved elevation, to allow for physiologic and accessible face down or prone positions. It can be 3D-printed using 3D scan of patient to provide custom fitting and located face, shoulder, arms, chest, and abdominal openings for perfect sizing. The device includes a suction devise which expands chest and abdominal cavity from below to assist breathing. The device avoids the need for positive pressure devises and allows for passive, more physiologic inspiration of air. The device allows for various prone positioning which has been shown to be helpful in COVID patients; and can deliver needed gases and biologic agents to support respiratory system by inhalation. A housing can be provided surrounding the device to isolate patient secretion and protect healthcare workers.

FIGS. 7-9 illustrate a respiratory assistance device 200 in one embodiment of the invention. The device includes a support base 210 having a top surface 220 and a support layer 230 coupled to the top surface 220 of the support base 210. The support layer 230 includes a first opening 240 sized to accommodate a user's face in prone position, and a second opening 250 sized to accommodate the user's chest and abdomen in prone position, the second opening 250 has a sealing surface 260 disposed about the perimeter of the second opening 250 configured to contact the user's chest and abdomen and fluidly seal the second opening when the user's chest and abdomen contact the sealing surface 260 in the prone position.

As shown in FIG. 7A, the device further includes a reversibly inflatable cavity 270 within the support base 210, wherein the cavity 270 is disposed interior to the support base 210 and sealed by the user's chest and abdomen in the prone position. The device also includes a pump 280 in fluid connection with the cavity 270 which is operable to control inflation and deflation of the cavity such that the user's chest and abdomen are moved to assist breathing of the user by applying positive and negative pressure to the chest and abdomen during inflation and deflation of the cavity 270. In embodiments, the device also includes a breathing device in connection with the first opening 240 configured to deliver a gaseous fluid to the mouth and/or nose of the user and one or more sensors configured to detect position and/or a physiological parameter of the user.

As described herein, the respiratory assistance device of the invention is designed to provide for safe, portable, economic, and controlled prone positioning and respiratory support of either awake or intubated individuals at all stages of disease, such as COVID-19 and related conditions, in home or outpatient settings, such as hospitals or post-hospital rehabilitation settings. It will be appreciated that the device may also be used in other setting, such as emergency, trauma, mass causality, and battlefield settings, as well as in zero gravity and extended space travel settings. The purpose of the device is to prevent, treat, or remediate/rehabilitate individuals with respiratory and circulatory (cardiovascular and lymph) threat or compromise.

In various aspect, the device of the invention is specifically designed to provide a rapidly customized accommodation of the patient's specific anatomy using imaging technology, such as 3D scanning and Computer Numerical Control (CNC) machining and 3D printing methods, as well as all other methods to achieve the same end.

In addition to providing direct respiratory support using external positive and negative pressure to the chest and abdomen, the device is specifically designed to promote optimal lung recruitment, perfusion, and ventilation, by reducing abdominal pressure, lowering intra thoracic pressure, and facilitating cardiovascular and lymphatic flow and drainage.

In certain aspects, safety features are incorporated to address known limitations and concerns related to the use of prone or bed bound positioning. Measures to provide for sensor and computerized control of pressure hazards related to prone positioning, as well as networked and artificial intelligence to support medical and nursing diagnostic and therapeutic functions may also be incorporated into the device.

In some aspects, the device allows for adjustment in the x/y/z plains to aid in lung function and care delivery, as well as providing modulated high frequency vibration measures to improve mucous management measures.

As discussed herein, respiration is supported using the application of both positive and negative pressures to the external chest and abdominal cavities in order to generate a pressure differential between the open respiratory tract and the plural surfaces. Various modes are provided to either assist the patient in normal respiration or completely control the respiratory cycles as needed. In some aspects, the device is designed to use its own self-contained pump and control mechanism and systems, or be driven by other conventional open source or ventilator systems.

Individuals with obesity, and specifically truncal obesity with increased abdominal volume and pressure, are at greater risk for respiratory compromise, hospital and ICU admission, and death. The device is designed to address this fundamental anatomic and metabolic risk factor. In addition, others suffer long term respiratory complications that can be treated by the device to improve the quality, depth and frequency of respiration, improve lymph drainage and enhance clearance of hyaluronan and other toxins from the lungs, reducing stimuli for lung fibrosis.

By placing the body on the device in a prone position and designing the edges of the second opening in such a way as the mass of the body is supported by the upper chest and shoulders, far lateral chest wall, and pelvis, pressure is taken off the abdomen primarily (but also the anterior chest wall). In some aspects, the device therapeutically supports and positions external body parts, but importantly, it supports internal body portions (or parts) such as the lungs, abdominal viscera, aorta, vena cava, heart, and lymphatic vascular system by means of lowering abdominal pressure and moving abdominal fat and viscera away from the lungs, diaphragm, and major cardiovascular and lymphatic vessels.

In certain aspects, the device of the present invention (e.g., PENPRAD) may be used in zero or microgravity environments, such as during space travel.

The possibility of long-term interplanetary space travel is becoming increasingly likely. Exposure to reduced gravity profoundly impacts the human body. Living in microgravity environments such as the International Space Stations causes profound shifts in all fluid compartments of the body. Cephalic movement of fluid occurs immediately due to the loss of hydrostatic pressure within the caudocranial fluid columns. Cerebral spinal fluid (CSF) builds up and is retained in the brain and there is an associated loss of brain white and grey matter. Profound macroscopic and microscopic changes have been documented in the cerebral grey matter, white mater, and ventricle, as well as changes in eye including optic edema, global flattening, and optic nerve sheath distention among others.

Breathing has been found to drive CSF movements, with forced inspiration moving fluid up the spinal column and forced expiration moving fluid out of the brain. The imbalance of these forces leads to a net retention of CSF in the brain. Forced breathing, in particular deep expiration, has been postulated as a possible measure to counteract the changes generated during spaceflight, yet no method has been provided to do so.

It has been shown previously that externally applied negative abdominal pressure alone leads to a reduction of increased CSF pressure in humans. Thus coupling negative external abdominal pressure with a forced inspiratory and expiratory cycle provides a method to counter the accumulations of CSF in the brain and associated disruption of normal brain fluid dynamics, retention of waste products, pathologic macroscopic and molecular changes, as well as loss of brain tissue.

Spaceflight-Associated Neuro-ocular Syndrome (SANS) likely results from a disruption of the recently discovered brain and ocular glymphatic systems which is a heretofore unknown perivascular lymphatic system in the brain. This system is most active during sleep at which time waste products from the brain tissue and eyes are flushed into the lymphatic system to be removed.

In some aspects, the method proposed herein is the application of continuous low negative pressures (e.g., −10 to −40) via the PENPRAD for prolonged periods of time (e.g., 3-8 hours) during sleep to essentially recapitulate more normal gravitational forces with associated fluid shifts away from the brain. Preferably as well, a modulated inspiratory and expiratory fluid pressure wave is applied over the continuous negative pressure to facilitate optimized arterial, venous, cerebral spinal fluid, and lymphatic fluid fluxes. The net result is improved system wide metabolic function.

Also, this method claims a specific multi modal treatment for Spaceflight-Associated Neuro-ocular Syndrome (SANS). The benefit of the system is that it is incorporated into normally scheduled sleep periods and thus does not interfere with other scheduled mission activities and requirements. In addition, the PENPRAD could be used with other prescribed exercise equipment and schedules to provide a form of assisted breathing exercises.

One proposed method to follow the metabolic effects of the method is to measure blood, urine, and CSF levels of metabolic by-products such as amyloid-$\beta$ from the brain, as well as the concentrations and ratios of high molecular weight to low molecular weight hyaluronan in these fluids as well.

Another application of the invention for space travel is the delivery of carefully titrated hydrogen gas during the use of the method to counter the harmful effects of ionizing space radiation of human lung, brain, and all other tissue as a result of the generation of highly reactive oxygen radicals such as the hydroxyl radicals via the Fenton reaction.

In one embodiment, the suit includes a removable helmet over which is mounted an extravehicular visor to protect the space traveler ("user") both from physical injury or damage and from the intense rays of the sun outside the space vehicle. Mounted on the user's upper chest is a portable life support system control box that provides oxygen as well as carbon dioxide removal. During extravehicular activity, the suit is periodically purged by user operation of an oxygen purge device controlled by the control box. The space suit has an opening sized to accommodate the user's chest and abdomen, the second opening having a sealing surface disposed about the perimeter of the second opening configured to contact the user's chest and abdomen and fluidly seal the second opening when the user's chest and abdomen contact the sealing surface. A reversibly inflatable cavity is provided within the suit support base, wherein the cavity is disposed interior to the support base and sealed by the user's chest and abdomen. A pump in fluid connection with the cavity and operable controls inflation and deflation of the cavity such that the user's chest and abdomen are moved to assist breathing of the user by applying positive and negative pressure to the chest and abdomen during inflation and deflation of the cavity. A mouthpiece or breathing device in connection with the first opening configured to deliver a gaseous fluid to the mouth and/or nose of the user. One or more sensors on the suit is configured to detect position and/or a physiological parameter of the user and allows the control box on the suit to adjust the pump and air pressure appropriately.

Other connections to the apparatus mounted on the astronaut's back providing for communication, ventilation and liquid cooling are from additional connectors by way of umbilical cable, for example. Suitable gloves space overshoes cooperate to protect extremities from the hazards of space and particularly provide protection by way of thermal insulation from intense sunlight and provide physical protection from micro-meteoroid bombardment. The outer garment can be an integrated thermal micro-meteoroid garment to provide thermal insulation and micro-meteoroid protection.

It will be appreciated that advantages of the device of the invention over existing devices as that it aligns the body with gravitational forces so that a counter pressure is not required to off-set the downward pull of the device onto the chest. In addition, by using the body's own weight as part of the sealing mechanism, along with custom fitting to the bodies size, shape, and contour, external fixation devices such as straps are not required. This allows for easier "donning and doffing" of the device. Comfort and ease of use are improved. The unit can also be supplied as an integrated system with both the support bed, seal, and pump unit being self-contained.

As further discussed herein, using imaging technology, such as 3D scanning and advanced machining, printing, and supply chain management, a custom designed and manufactured device is provided. It will be appreciated that the present disclosure does not limit the use of more customary manufacturing methods to produce the device in a variety of sizes and configurations for large scale distribution and sale as well.

By providing space for the abdomen to expand and positioned in a dependent manner, pressure is taken off the diaphragm, lungs, and major vessels improving ventilation, perfusion, lymphatic, cardiovascular and brain function during use of the device.

In one example, the fabrication of a mass-customized respiratory assistance device is described. This is done first by generating a 3D model of the chest of the patient, rendering the model as a reformable 3D physical model, and fabricating the device shell using rapid mass-customized production techniques that can fabricate each device in less than 30 minutes.

FIG. 12 shows an exemplary 3D imaging system (10) generally includes a camera or optical device (2) for capturing 3D images and a processor (4) that processes the 3D images to construct a 3D model. According to one exemplary embodiment, the processor (4) includes means for selecting 3D images (6), a filter (8) that removes unreliable or undesirable areas from each selected 3D image, and an integrator (10) that integrates the 3D images to form a mosaic image that, when completed, forms a 3D model.

Preferably, the system uses LIDAR sensors or distance sensors using time of flight principles to map dimensions of the patient body. One embodiment uses a camera in a smart phone as the optical device (2) to generate the 3D model from a plurality of images of the user's chest. The process breaks the chest images into individual points and calculates depth based on how they distort as the phone camera is moved and thus 3D geometry is generated with a live camera view. Another embodiment combines static pairs of photos to capture a single 3D view of a scene. In one embodiment, the system photographs a patient's body in 3D, captures linear and volumetric measurements, and creates an exact 3D replica of the chest on screen. The doctor examines this 3D model with the patient during the consultation, and performs proposed changes to the respiratory assistance device which can be rendered to the patient to visualize the expected result in advance of an actual respiratory assistance device production. In another embodiment, a 3D webcam is used with two cameras spaced roughly the same distance apart as human eyes, for the stereoscopic effect. 3D data acquisition and object reconstruction can be performed using stereo image pairs. Stereo photogrammetry or photogrammetry based on a block of overlapped images is the primary approach for 3D mapping and object reconstruction using 2D images. Close-range photogrammetry where cameras or digital cameras can be used to capture the close-look images of objects, e.g., body part such as feet, and reconstruct them using the very same theory as the aerial photogrammetry.

In yet another embodiment, the optical device (2) illustrated in FIG. 12 can be, according to one exemplary embodiment, a 3D camera configured to acquire full-frame 3D range images of objects in a scene, where the value of each pixel in an acquired 2D digital image accurately represents a distance from the optical device's focal point to a corresponding point on the object's surface. From this data, the (x,y,z) coordinates for all visible points on the object's surface for the 2D digital image can be calculated based on the optical device's geometric parameters including, but in no way limited to, geometric position and orientation of a camera with respect to a fixed world coordinate, camera focus length, lens radial distortion coefficients, and the like. The collective array of (x,y,z) data corresponding to pixel locations on the acquired 2D digital image will be referred to as a "3D image". Alternatively, the 3D camera can simply be two cameras spaced apart at a predetermined distance to provide 3D perspective capture. 3D image integration can be done using pre-calibrated camera positions to align multiple 3D images to merge the aligned 3D images into a complete 3D model. More specifically, cameras can be calibrated to determine the physical relative position of the camera to a world coordinate system. Using the calibration parameters, the 3D images captured by the camera are registered into the world coordinate system through homogeneous transformations. While traditionally effective, this method requires extensive information about the camera's position for each 3D image, severely limiting the flexibility in which the camera's position can be moved. The data capture can be viewed in an exemplary modeling system, according to one exemplary embodiment. The exemplary modeling system can support 3D image acquisition or capture, visualization, measuring, alignment and merging, morphing, editing, compression and texture overlay, all controlled using a database manager.

Next, using a CAD tool, a professional can edit/revise the respiratory housing as needed. Next, sensors can be incorporated into the mass-customized device. Multiple digital health sensors can be integrated into sensor networks comprising other body-worn sensors and/or ambient sensors. Some monitoring systems can assist the gathered sensor and wearables data to be uploaded to a remote site such as a hospital server for further clinical analysis. With the advent of cloud-computing, many wearable sensor systems can be easily upgraded without the need for user installation of software in their monitoring devices, which makes it easier and cheaper to maintain the health monitoring system networks.

The resulting 3D model can be synthesized as a physical device using the systems and methods disclosed below for shaping a reformable material by holding a volume of particles inside a container having a first elastomeric membrane surface; infusing the volume with a liquid to mobilize the volume of particles; and pressing a master shape into the membrane with atmospheric pressure. Alternatively, the model can be printed using various 3D printing techniques such as selective laser sintering, among others.

In one embodiment, in addition to the 3D modeling, actual chest pressure can be captured and used for treatment or for analysis. In addition to pressure sensing, other personal data can be captured. For example, the sensors can include chest bio-impedance sensors that use bioelectrical impedance analysis (BIA) to estimate the heart rate by amplifying the pulsatile impedance component superimposed on the basal impedance. One embodiment detects the heart rate (HR) from bioimpedance measured in a single foot. Four electrodes are used for measurement of bioimpedance signal; two electrodes for injecting current and the other two to capture the voltage signal from human body. The bio-impedance signal shows deflections corresponding to systole and diastole activity as a measure of heart rate. The electrodes embedded in the footwear 4 apply a 50 kHz voltage between the outer electrode pairs and measure the drop in voltage across the inner electrode pairs in one embodiment. An impedance converter AD5933 separates impedance into real and imaginary part using discrete Fourier transform. The real and imaginary values of the measured bio-impedance signal are processed by a processor to obtain a continuous signal. The bioimpedance signal obtained after de-noising using adaptive thresholding. For heart rate detection, synchronous demodulator plays vital role by demodulating the bio-impedance signal from current carrier. To achieving high CMRR in signal in analog differential synchronous demodulator for AC signals, the signal is synchronously demodulated using the floating-capacitor with high CMRR. An impedance analyzer is used for getting bio-impedance signal. Wavelet thresholding methods can be used for noise removal where wavelet coefficients are threshold in order to remove their noisy part.

Another embodiment measures heart rate and/or EKG with sensors directly provided in the footwear 4 or using external wearable devices and such data combined with foot-ground contact information is used for ambulatory estimates of maximal aerobic power from foot. The user's maximal rate of oxygen uptake sets the upper limit for sustained physical activity and is the standard measure of aerobic fitness.

In one aspect, systems and methods are disclosed for shaping a reformable material by holding a volume of particles inside a container having a first elastomeric membrane surface; infusing the volume with a liquid to mobilize the volume of particles; and pressing a master shape into the membrane with atmospheric pressure.

In another aspect, a method to form an object includes infusing a liquid into a container having a first elastomeric membrane surface; pressing a master shape into the membrane with atmospheric pressure; and shaping a reformable material into the object according to the master shape.

In yet another aspect, a method to form an object includes infusing a liquid into a container having a frame with first and second elastomeric membranes; a first port to deaerate the volume of particles; and a second port to infuse the volume with a liquid for mobilizing the volume of particles; pressing a master shape into the membrane with atmospheric pressure; and shaping a reformable material into the object according to the master shape.

Implementations of the above aspects may include one or more of the following. The volume of particles can be deaerated. The liquid can be extracted through one or more screen elements placed proximal to the volume of particles. The atmospheric pressure continues to hold the particles in place against the elastomeric membrane when the master shape is removed from the outer surface of the membrane. The method includes heating and driving liquid from the particle volume. A residue of a binding adhesive is left to lock the particles into a continuous force-resisting mass. A complementary shape is impressed to the master shape in the membrane. A rigid outside frame can be used with top and bottom elastomeric membranes facing the top and bottom surfaces of the container. The master shape can be pressed against the top elastomeric membrane of the container by atmospheric pressure. The pressing operation includes applying a flexible vacuum cap which is sealed over the shape and against the container's top surface membrane; evacuating air from a space between the top membrane and the vacuum cap; extracting liquid from the volume; and pressing the particles within the container by atmospheric force acting in opposed directions against the vacuum cap and the bottom surface membrane. Air can be introduced into the vacuum cap, and then the cap and the master shape can be removed from the formed surface of the elastomeric membrane. The container is formed against the master shape. The method includes placing the master shape on an air-impermeable surface; placing a membrane of the container over the shape; and placing a vacuum cap or a vacuum-bagging film over the container to effect forming of the elastomeric membrane against the master shape. An envelope with a vacuum seal on its perimeter can be used to contain a mass of particles and to extract air from between the master shape and the envelope. The master shape can be placed on the top elastomeric surface of a first rigid-framed container and a membrane surface of a second container can be placed over the master shape. The second container fits inside the frame of the first container and a vacuum cap is placed over and sealed outside the second container against the surface membrane of the first container. The method includes evacuating the volume under the vacuum cap and pressing the master shape between the elastomeric sides of the first and second containers. The liquid is extracted so that the two volumes of particles are pressed together and against the membranes surrounding the contained shape. The vacuum cap can be vented with air and removed; the top container can then be removed; and the shape can then be removed from the membrane of the bottom container. The top container can be placed over the bottom container; and forming a closed, shaped cavity complementary to the surface of the master shape used to form the cavity. Two identical containers of either the first or the second container can be pressed around a master shape with or without using the vacuum cap. The containers can be joined and sealed by either a seal mounted on one or both of the containers or by seals mounted on a seal ring which fits between the two containers. The liquid can be extracted prior to the master shape being removed from the shaped reformable material. The liquid can be withdrawn to leave a residue of liquid on the shaped reformable material; and solidifying the residue. The method can include preforming a surface material over the master shape as with thermoforming or additive processing. The container walls can be air and liquid impermeable. An inelastic formable surface can be used that conforms to the master shape surface. A surface can be formed over the master shape to conform to the master shape and the shaped material surface can be pressed against the volume of particles without deforming the shaped material surface. The method includes providing a release surface to the master shape; pressing the master shape against the volume of particles to form the object against the release surface; and removing the object from the master shape with the release surface. The release surface can be applied to the master shape with a surface element covering the reformable material surface not overlaid with the master shape surface.

In another aspect, an apparatus to form an object in accordance with a master shape includes a container to hold a volume of particles, said container having a first elastomeric membrane surface; a first port to deaerate the volume of particles; and a second port to infuse the volume with a liquid for mobilizing the volume of particles; and a press coupled to the container to move the master shape into the membrane to shape a reformable material into the object according to the master shape.

Implementations of the above aspect may include one or more of the following. One or more screen elements can be placed proximal to the volume of particles to extract the liquid. Atmospheric pressure can be used to hold the volume of particles in place against the elastomeric membrane when the master shape is removed from the membrane. A heater can be used to heat and drive liquid from the particle volume. The container can be a rigid outside frame and top and bottom elastomeric membranes facing the top and bottom surfaces of the container, and wherein the master shape is pressed against the top elastomeric membrane of the container by atmospheric pressure. The apparatus can include a flexible vacuum cap sealed over the shape and against the container's top surface membrane; a third port to evacuate air from a space between the top membrane and the vacuum cap; and pressing of the particles within the container by atmospheric force acting in opposed directions against the vacuum cap and the bottom surface membrane. Air can be introduced into the vacuum cap and then the cap and the master shape can be removed from a surface of the elastomeric membrane. The master shape can be placed between an air-impermeable surface and the membrane of the container and wherein a vacuum cap or a vacuum-bagging film is placed over the container to form the elastomeric membrane against the master shape. An envelope with a vacuum seal on its perimeter can be used to contain a mass of particles and to extract air from between the master shape and the envelope. The master shape can be placed on the top elastomeric surface of a first rigid-framed container and placing a membrane surface of a second container over the master shape. The second container fits inside the frame of the first container and a vacuum cap is placed over and sealed outside the second container against the surface membrane of the first container. A vacuum pump can evacuate the volume under the vacuum cap and press the master shape between the elastomeric sides of the first and second containers. A pump can extract the liquid so that the two volumes of particles are pressed together and against the membranes surrounding the contained shape. The vacuum cap can be vented with air and removed; the top container is removed; and the shape is removed from the membrane of the bottom container and the top container is placed adjacent the bottom container to form a closed, shaped cavity complementary to the surface of the master shape used to form the cavity. The first and second containers can be identical and can be pressed around a master shape without using the vacuum cap. The containers can be joined and sealed by either a seal mounted on one or both of the containers or by seals mounted on a seal ring which fits between the two containers. A seal ring can be used to channel vacuum or air pressure between the containers and to hold the master shape in a precise orientation and position between the two opposed containers. An expander can be used within the container to press the particulate material against cavity walls of the container. The apparatus can include a second container cooperating with the first container to form a complementary cavity from the master shape; and a third container placed in the complementary cavity to replicate the master shape. A rigid frame or a flexible-edge frame can be used. The frame can form a continuous surface complementary to a master shape's surface. A second elastomeric membrane can be used, and the elastomeric membranes can overlap or abut each other. Additional containers each having a membrane can be used with the container's membrane to form a continuous surface of membranes. Further, additional containers can be used to form a shape complementary to the interior of a master cavity.

In another aspect, an apparatus to form an object in accordance with a master shape includes a container to hold a volume of particles, said container having a frame with first and second elastomeric membranes; a first port to deaerate the volume of particles; and a second port to infuse the volume with a liquid for mobilizing the volume of particles; and a press coupled to the container to move the master shape into the membrane to shape a reformable material into the object according to the master shape.

Implementations of the above aspect may include one or more of the following. The second membrane is bonded to the frame. The first membrane is mounted to a seal. A clamp can secure at least one membrane to the frame. One or more ports can be provided on the frame. Liquid, evacuation, and vacuum-activated seal tubes can be mounted to the frame. A rim evacuation screen element can be positioned in the frame. The frame can be rigid or flexible. A vacuum activated seal can be provided on the frame. A tube can be used for evacuating and filling the container. Double layer screens having feed elements to distribute and extract liquid through the volume of particles can be used. One or more screens can be used to conform to the master shape. One or more internal screens can be mounted with the particles flowing on both sides of each internal screen. The frame can have one or more containers joined together around the master shape or alternatively can have one or more containers joined by vacuum seals. One or more feed tubes can connect to an interior element inside the membrane. A flexible spine element can be used within an interior cavity of the container. One or more reinforcement fibers can be used, and in certain implementations, the fibers can be distributed in bundles within the volume of particles. An air pump or source can be used to provide internal pressurization. A vacuum source can provide a vacuum between a cavity in the container and the container. An air source and a vacuum source can alternately pressurize and vent the container to distribute the volume of particles therein. A seal ring can be used. The seal rings can be mounted against seals or can be mounted with attached seals. The attached seals can be vacuum activated. A second container can be joined with the container and wherein a vacuum is formed in an interior of the joined containers. The master shape can be mounted on the seal ring. Flanges can be mounted to control a mating line between opposed membranes of containers. A second container can be positioned within a cavity formed by an outside container. A vacuum seal can be used with a vacuum cap. A vacuum tube can be used that penetrates through the membrane. A vacuum cap with mounted container can be used in place of the membrane. One or more screen elements can be placed proximal to the volume of particles to extract the liquid. Atmospheric pressure holds the volume of particles in place against the elastomeric membrane when the master shape is removed from the membrane. A heater can be used to heat and drive liquid from the particle volume. The container can have a rigid outside frame and top and bottom elastomeric membranes facing the top and bottom surfaces of the container, and wherein the master shape is pressed against the top elastomeric membrane of the container by atmospheric pressure. An envelope with a vacuum seal on its perimeter can contain the mass of particles and extract air from between the master shape and the envelope. The master shape can be placed on the top elastomeric surface of a first rigid-framed container and a membrane surface of a second container placed over the master shape. An expander within the container can be used to press the particulate material against master shapes and against cavity walls of other containers. The apparatus can have a second container cooperating with the first container to form a complementary cavity from the master shape; and a third container placed in the complementary cavity to replicate the master shape. A second elastomeric membrane can be used that either overlaps or abuts the adjacent membrane. Additional containers each having a membrane coupled to the container can be used to form a continuous surface of membranes. Additionally, one or more additional containers can form a shape complementary to the interior of a master cavity.

In yet another aspect, a base station is disclosed to form an object in accordance with a master shape. The base station includes a liquid receiver; a vacuum source to evacuate air from the liquid receiver; an air compressor, pump or source to generate pressurized air; and a controller coupled to the liquid receiver, the vacuum source and the air compressor to form the object.

Implementations of the base station can include one or more of the following. Tubes can be used to provide vacuum and to control the flow of liquids to and from the receiver. Valves, sensors, and other circuits can be interfaced with the controller. An electrical power source can be used to provide power to operate valves, sensors, the vacuum pump and the air compressor. The controller can be a menu-driven process controller. A heater can be used to vaporize and expel liquid from containers of reformable material. The reformable material creates contours of the master shape or alternatively can be molded against a complementary surface of an elastomeric membrane. The liquid contains a soluble binder, which can be left on a shaped volume of particles. The binder locks a shaped volume of particles in place after the liquid is removed. The heater can be a radiant heater, a convective air heater, microwave heater, radio-frequency heater, or inductive heater. The heater can include one or more heating elements within the container. The heater is controlled by the controller. A container can be used to hold a volume of particles, said container having a frame with first and second elastomeric membranes; a first port to deaerate the volume of particles; and a second port to infuse the volume with a liquid for mobilizing the volume of particles; and a press coupled to the container to move the master shape into the membrane to shape a reformable material into the object according to the master shape. Alternatively, the container can have a first elastomeric membrane surface; a first port to deaerate the volume of particles; and a second port to infuse the volume with a liquid for mobilizing the volume of particles; and a press coupled to the container to move the master shape into the membrane to shape a reformable material into the object according to the master shape. The container can include a rigid outside frame and top and bottom elastomeric membranes facing the top and bottom surfaces of the container, and wherein the master shape is pressed against the top elastomeric membrane of the container by atmospheric pressure. The base station can also include a flexible vacuum cap sealed over the shape and against the container's top surface membrane; a third port to evacuate air from a space between the top membrane and the vacuum cap; and pressing of the particles within the container by atmospheric force acting in opposed directions against the vacuum cap and the bottom surface membrane. The master shape can be placed between an air-impermeable surface and the membrane of the container and a vacuum cap or a vacuum-bagging film can be placed over the container to form the elastomeric membrane against the master shape. The vacuum pump can be a mechanical pump or an air driven pump such as a Venturi pump. A second vacuum pump can be used. Isolating valves can be used, and a regulator and one or more valves can be used to pressurize a liquid tank. A vent valve can also be used to cycle from a vacuum source to a pressure source. A three-way valve can route air and vacuum to the liquid tank. A filter can be used to prevent particulate carryover. An air-liquid separator and/or a level indicator can also be used. A vacuum, pressure, liquid and temperature sensor can provide data to the controller for process control. A heat exchanger can be used to condense vapor. A slurry transfer tank can be connected to the container. The container can be a single unit, or can have a plurality of containers adjacent to or inside the container to form a cavity. The containers can be mated with a seal ring.

In yet another aspect, a method to shape a reformable material includes holding a volume of particles inside a container having a first elastomeric membrane surface; and infusing the volume of particles with a liquid; agitating the liquid to provide one or more surges of liquid to mobilize the volume of particles; and pressing a master shape into the membrane with atmospheric pressure.

Implementations of the above method may include one or more of the following. The method may provide locally distributed surges or globally distributed surges. The surges can exert differential liquid forces on particles to displace them relative to one another and facilitate their movement into a closely-packed volume. A differential pressure can be applied between a master shape side and a liquid-particle side of the membrane. The pressure between a vacuum cap and the membrane can be decreased to move the membrane in a first direction or increased to move the membrane in a second direction. The membrane is free to move relative to the master shape. Excess liquid can be removed to leave particles against the membrane. Air can be evacuated from space between the membranes. The particles can be packed against the membranes and the master shape. The liquid with the vacuum cap and membrane pressed against the master shape can pack the particles against the membranes and the master shape. The agitating operation can include pulsing or vibrating the liquid. The vibration frequency can be adjusted to displace one particle relative to another to keep the particles moving freely in relation to one another. The amplitude of the liquid pulsation can be proximally equal to a diameter of the particles. A first surge of liquid can be directed towards a desired transport direction and a second surge smaller than the first surge can be directed in an opposite direction to the transport direction. The agitating of the liquid can be used to minimize blockage. The method includes maintaining the volume of the container constant and completely filled to force the particles against the master shape. The method includes extracting transitional liquid from the container; and adding new liquid equal in volume to the transition liquid.

In yet another aspect, a shape-reformable composition includes a carrier medium having a carrier density; and a plurality of solid bodies having a density substantially similar to the carrier density, said solid bodies being transitionable from a formable state to a three dimensional solid shape. The bodies can have a density substantially lighter or heavier than that of the carrier if they have a high ratio of surface area to volume. The bodies can be stiff, flexible or elastomeric. The bodies can be regular or irregular and can be of substantially different types intermixed.

Implementations of the composition can include one or more of the following. The carrier medium fills voids or interstices between the solid bodies such that the voids or interstices are free of air or gas bubbles. The solid bodies can have near-liquid or fluent mobility during the formable state. The solid bodies can transition to the solid shape through an introduction and an extraction of a predetermined amount of the carrier medium. The solid bodies can be positioned in a container having a first elastomeric membrane surface. Liquid can be introduced to mobilize the volume of particles. A master shape can be pressed into the membrane with atmospheric pressure. The resulting solid shape is a stable, force-resisting shape. The solid bodies and carrier medium form a reversible state-changeable mixture. The carrier medium can be a liquid or a gaseous froth. The shape can be a reformable mold or a reusable template to capture dimensions of impressed shapes for transfer to a mold.

In other aspects, a system is disclosed for holding a volume of particulate material inside an air and liquid-impermeable container with at least one elastomeric membrane surface; deaerating the volume; infusing the volume with a liquid to cause it to be mobile; pressing a master shape into the membrane via atmospheric pressure; and extracting the liquid through one or more screen elements which are placed in or adjacent to the particle volume. The extraction causes atmospheric pressure to press the particles against the contours of the shape and against each other. This pressure continues to hold the particles in place against the elastomeric membrane when the master shape is removed from the outer surface of the membrane. The system further has a means to heat and drive liquid from the particle volume and, in certain embodiments, to leave a residue of binding adhesive which locks the particles into a continuous force-resisting mass.

Operation of one embodiment is as follows with a particular embodiment of the container which has a rigid outside frame and a membrane face on the top and bottom surfaces. With the particle volume infused by liquid, a master shape is pressed against the top elastomeric membrane of the container by atmospheric pressure, thereby causing the shape to impress a complementary shape in the membrane. This pressing is accomplished through use of a flexible or elastomeric vacuum cap which is sealed over the shape and against the container's top surface membrane, following which air is evacuated from between the top membrane and the vacuum cap. Liquid is then extracted from the volume and the particles within the container are pressed together by atmospheric force which acts on all exterior surfaces of the tool-bed but in particular in opposed directions against the vacuum cap and the bottom surface membrane. Air is then introduced into the vacuum cap, the cap removed and the master shape removed from the formed surface of the elastomeric membrane.

In another embodiment, the container is formed against a master shape with the process of liquid infusion, a pressing action via atmospheric pressure and a liquid extraction process. This embodiment is essentially a flat envelope with a flexible outside rim and two opposed elastomeric membranes. To use this embodiment a master shape is placed on an air-impermeable surface, a membrane of the container is placed over the shape, and either a vacuum cap or a vacuum-bagging film is placed over the container to effect forming of the elastomeric membrane against the master shape. The envelope may also have a vacuum seal on its perimeter and so has the combined function of containing a mass of particles and of serving to extract air from between the master shape and the envelope.

In implementations, there can also be a combined use of the first and second containers described above. A master shape may be placed on the top elastomeric surface of the first rigid-framed container and then a membrane surface of the second container is placed over the shape. The second container fits inside the frame of the first container and a vacuum cap is placed over and sealed outside the second container against the surface membrane of the first container. When the volume under the vacuum cap is evacuated the master shape is pressed between the elastomeric sides or faces of the two containers. Liquid is then extracted so that the two volumes of particles are pressed together and against the membranes surrounding the contained shape; the vacuum cap is vented with air and removed; the top container is removed; and the shape is removed from the membrane of the bottom container. When the top container is again placed over the bottom container, a closed, shaped cavity is formed which is complementary to the entire surface of the master shape which was used to form the cavity.

In yet another embodiment, a combination of containers can be used in which two identical containers of either the first or the second type may be pressed together around a master shape without use of the vacuum cap. In this case the containers are joined and sealed by either a seal mounted on one or both of the containers or by seals mounted on a seal ring which fits between the two containers. The seal ring may be further employed to channel vacuum or air pressure between the two containers and to hold the master shape in a precise orientation and position between the two opposed containers. The seal ring may also furnish access to the formed cavity for the purpose of injecting a moldable material into the cavity.

In yet another embodiment of the container the container itself is formed into a replica of a master shape, or into a shape complimentary to a master cavity by another combination of the elements and processes described above. The exterior of this third type of container may be formed entirely from an elastomeric material or may be formed from a combination of elastomeric, flexible and rigid materials. Though the container might be shaped against a single surface, it can also be shaped over substantially its entire surface by confining it within a master cavity formed by two or more closely-fitting mold parts. Key to this forming process is an expansion means within the third container which presses the particulate material against the cavity walls.

In another embodiment, there is combined use of the containers which employ the three types of containers described above for a single purpose. The first or second types can be used to form a complementary cavity from a master shape. The third type of container can then be placed in the cavity, which is now used as a master cavity, and the third type formed complementary to the master cavity contours, thereby creating a replica of the original master shape.

It can be appreciated that there are numerous variations of containers and varied combinations of containers which can be employed either to form a surface which is complementary to the exterior surface of a master shape in part or in whole, or to form a surface or surfaces complementary to the interior contours of a hollow master shape or master cavity. For instance more than one container of the first type (rigid frame) or second type (flexible-edge) can be employed to form a continuous surface complementary to a master shape's surface, with the elastomeric membranes of the containers either overlapping or being abutted together. Containers of the second type may also have a membrane and particle configuration that allows two or more of the containers to be "tiled" together to form a continuous surface of particle-backed membranes. Likewise, two or more containers of the third type can be employed together to form a shape complementary to the interior of a master cavity.

In yet other embodiments, a forming system also includes a base station which provides evacuation of air, liquid infusion into and liquid extraction from the particle filled containers. The base station also furnishes vacuum forces to enable the forming operations to be performed on the various containers either singly or in combination. The base station comprises a liquid receiver; onboard vacuum system or provision to connect to an external vacuum source; an air compressor or provision for external connection to pressurized air; valves, fittings and tubing or piping to provide vacuum and to control the flow of liquids to and from the containers; an electrical power supply to operate the valves, process sensors and any onboard mechanical vacuum pumps and air compressors; and a menu-driven process controller to operate the base station.

In another embodiment, a forming system includes a heater which may be used to vaporize and drive out liquid from the particle filled containers, and further to heat any materials which may be used to recreate the contours of the original master shape through molding against the complementary surface of the formed elastomeric membrane. The vaporizing or drying process is especially advantageous when the liquid contains a soluble binder which remains on the pressed-together particles and locks the shaped volume of particles in place when the liquid has been driven out of the container. The heater may take numerous forms to include a radiant heater, a convective air heater, heating elements within the particle-filled container, and various types of inductive (e.g., microwave or radio-frequency) heaters. The heater may be powered and controlled by the base station and its controller, or the heater may be powered and controlled separately.

Next a reformable respiratory assistance device making embodiment is detailed. In this system, the 3D model of the respiratory assistance device as customized by the user or a doctor for the user is sent to a reformable shape object fabricator, which is detailed next. The fabricator renders a physical model of the 3D model and then applies a state-changeable mixture that includes uniform, generally ordered, closely-spaced solid bodies and a liquid carrier medium, with the liquid filling any voids or interstices between the bodies and excluding air or gas bubbles from the mixture. Within the mixture, the solid bodies can be caused to transition from a near-liquid or fluent condition of mobility to a stable, force-resisting condition. To create mobility, a small excess quantity or transition liquid is introduced to create a fluent condition by providing a slight clearance between the bodies which permits the gently-forced introduction of at least two simultaneous slip planes between ordered bulk masses of the bodies at any point in the mixture. Transition to the stable condition is caused by extraction of the transition liquid, removing the clearance between bodies and causing them to make stable, consolidated contact. FIG. 13A shows a computer controlled system for fabricating parts that whose dimensions are specified in a data file and rendered by a CAD/CAM software such as Solidworks™ or Autocad™ or even Paint™, and the object described in the data file needs to be fabricated. Conventional printers print a layer at a time and can take significant time in making a single product. To accelerate the production process, the system of FIG. 13A takes 3D data from a computer with 3D CAD design 1002 and provides the information to an actuated 3D shape generator 1004 that is placed inside of a reformable object copier 1006. The 3D shape generator 1004 forms the 3D object, and the object copier 1006 reproduces copies of the formed 3D object in minutes, thus greatly accelerating production of mass-customized products which otherwise takes hours on a 3D printer.

The 3D shape generator 1004 is a complete computer actuated system that is enclosed in the object fabricator 1006. CAD data is downloaded by wire or wireless connection to the shape generator 1004. Based on the desired dimensions, one embodiment of the 3D shape generator 1004 forms a 3D object by having an array of computer controlled moveable pins whose height is adjusted in accordance with the CAD design file, and the overall shape is smoothed by a Lycra sheet or felt sheet. The pins or rods lift the felt or Lycra sheet to form a 3D object based on the CAD design file. In this embodiment, an array of N×N micro hydraulic actuators can be used to form the shape. This embodiment is a dense hydraulic planar pin-rod matrix array. Another embodiment actuates an N×N pin-rod matrix driven by servomotors. In either case, each pin-rod is controlled individually, similar to pixels on a screen except that the pixel has height as well.

In one embodiment, the N×N matrix can be an array of electro-mechanical pins positioned in a frame. The frame is adapted to hold the plurality of pins in a parallel position to one another in a series of columns and rows, such that the distal ends of the plurality of pins together form a flat virtual plane. Each pin of the plurality of pins includes an elongated housing member defining a linear axis therethrough, and a pin member adapted to slide linearly in either direction along the axis. Each of the housing member includes an upper electromagnet, and a lower electromagnet separated from the upper electromagnet. Each of the electromagnet is adapted to move its respective pin member linearly in either direction. Each of the pin member includes a linear potentiometer, a, magnet and an electronic transmitter attached to an opposite end to the distal end, such that when each of the pin members are moved linearly each respective linear potentiometer sends a signal to its respective transmitter which in turn sends an electronic signal describing its movement within its respective housing member, a plurality of electronic wires respectively connected to each transmitter, such that electronic signals can be relayed to and from each respective pin; an analog-digital converter connected to the plurality of electronic wires and adapted to convert the analog electronic signals relayed by the transmitters into digital format to be transmitted, processed, stored, and then converted back into analog form for return transmittal to the set of pins. A processor is connected to the converter and adapted to retrieve the electronic signals from the converter, store them, and retransmit them back to the converter when desired, such that a user can displace the pin members from the virtual plane in any pattern, have electronic signals sent, processed, stored, and returned to the same set of pins, or another separate set of pins, at a later time to thereby displace the pins to the same positions as the original pattern chosen by the user.

In one embodiment, the pin array device has each of the housing member of each pin comprise an upper frame upper electromagnet, upper spring, lower electromagnet, lower spring and shield along the entire upper frame wall to separate magnetic field between each interactive pin. The lower frame consists of the outer fixed part of the potentiometer and electronic transmission from electronic transmitter to both electromagnets. The pin consists of a magnet, a mobile portion of the potentiometer, electronic transmitter that picks up all the wire and sends position signal and feeds the power to both electromagnets via the lower housing. The electronic signal may be a Pulse Width Modulation signal, and the displacement of each of the pin members is proportional to the strength of the Pulse Width Modulation signal received by the electromagnets.

FIG. 13B shows the shape of the object when a felt cover or a Lycra cover is placed above the pins to form a 3D structure that can be digitally controlled using a CAD output to form a 3D object that can then be copied or fabricated using the reformable object fabricator 1006.

In yet another embodiment shown in FIGS. 13C-13D, the pins are moved by the action of a plate, common to all or a portion of the pins, that can extend and retract along a single axis of motion. A clutch mechanism cooperates with the moving plate to fix the pins at a desired position. In an exemplary embodiment, the shape generator 1004 can include a membrane covering the pins. A plurality of pins 1011-1018 arranged in an array such that respective head portions 1021-1028 associated with the pins collectively define a surface 1030. It will be appreciated that the area of array is not necessarily defined by two Cartesian dimensions. For example, the pins could be arranged along a spherical or hemispherical surface, with the array spanning the azimuthal and polar dimensions across the surface of the sphere. The position of a given pin (e.g., 1011) can be adjusted along an axis of motion.

In one embodiment, an optional motion plate 1032 can be provided to move the pins along the axis of motion as to adjust the position of the pins. The motion plate 1032 can be moved by reasonable mechanical or electromagnetic means. For example, the plate 1032 can be moved via an electrical motor, a hydraulic assembly, or one or more solenoid coils exerting a magnetic force.

A clutch mechanism 1034 is operative to arrest the motion of a given pin at a desired position. The respective positions of the pins can be selected to deform the display surface into a desired raised image. The clutch mechanism can comprise reasonable means for selectively arresting the motion of the pins. For example, the clutch mechanism 1034 can comprise components for mechanically or magnetically engaging the pins.

One embodiment provides an upper plate with a plurality of apertures through which corresponding pins forming the object's surface can pass. The pins can include head portions with areas larger than that of their respective apertures, to more fully tessellate the display surface and to help maintain the pins within the apertures. The upper plate can house part or all of a clutch mechanism that selectively engages one or more pins to maintain the pins at a desired position. The upper plate houses one or more banks of solenoids that shift the position of one or more portions of the clutch (not shown) that physically communicate with the pins. In an exemplary embodiment, the solenoids shift the position of one or more bars such that they contact or release circumferential grooves on the surface of the pins. This embodiment also provides a lower plate and a base plate disposed parallel to the upper plate along one or more support posts. A lifting plate can be suspended between the lower plate and the base plate on one or more guide posts. The lifting plate can be raised or lowered via a motor and belt system to adjust the position of the pins. For example, the pins can be reset to a fully raised position by raising the lifting plate to its maximum height. The movement of the guide pins and the action of the clutch mechanism can be regulated by a processor.

FIG. 13D illustrates a side view of an exemplary computer shaped object that can be reproduced or fabricated formed in accordance with an aspect of the present system. Two facing and opposite bed of pins can form a 3D shape for the sole or insert. The insert and/or the respiratory assistance device can be produced in discrete sizes such as US sizes 4, 4.5, 5, 5.5, 6, 6.5, 7, 7.5, 8, 8.5, 9, 9.5, 10, 10.5, 11, 11.5, 12, 12.5, 13, 13.5, 14, 14.5, 15, 15.5, 16, 16.5, 17, 17.5, and 18, for example. Thus, a plurality of sized beds can be used, or one large pair of beds covering size 20 can be used to produce all other smaller sizes. Turning back to FIG. 13D showing one of the beds, the selected view of the 3D object creator comprises one row of four pins 2102-2108. It will be appreciated that a functioning computer controlled 3D object creator can contain a large number of pins arranged across multiple rows in order to reproduce the shape of the 3D object with high fidelity.

In an exemplary embodiment, the rows containing the pins 2102-2108 are staggered as to form a honeycomb pattern. Accordingly, the pins 2102-2108 are arranged in a plurality of linear rows and one or more staggered columns. Alternatively, the pins can be arranged in a Cartesian grid, such that both the rows and the columns are linear. It will be appreciated that other methods of arranging the pins can be utilized, and that the placement of the pins will vary with the necessary size and spacing of the pins, as well as the desired shape (e.g., flat, spherical, recessed) of the array.

In the illustrated display, the pins 2102-2108 have respective cap portions 2112-2118 that define a raised surface. The cap portions 2112-2118 can be covered by an elastic membrane or felt layer 2120 to provide a relatively smooth surface for the object. The use of the pin caps 2112-2118 and the membrane 2120 will depend on the application. The pins 2102-2108 pass through respective apertures in a stationary, outer plate 2124. The outer plate 2124 houses a clutch mechanism 2126 that acts to maintain the pins in their desired positions. In an exemplary implementation, the clutch mechanism 2126 can comprise a series of row bars and column bars having two associated positions. In a first, open, position, a given bar allows the pins within its associated row or column to move freely. In a second, restraining, position, the bar is moved to physically contact the pins at one of a plurality of evenly spaced grooves on the pin, maintaining the pin at its position. The spacing of the grooves corresponds to a desired resolution of the display 2100. The position of the bars can be changed via one or more banks of solenoids. In an exemplary embodiment, the bars are biased, by a spring or similar mechanism, to remain in the restraining position, until a solenoid is actuated to move the bar into an open position.

During operation, the pins can be reset into a fully extended position by a reset plate 2130. The reset plate 2130 can then be incrementally withdrawn to allow the pins 2102-2108 to retract toward the interior of the display device. In an exemplary embodiment, the reset plate 2130 is moved by a motor and belt arrangement. The pins 2102-108 have associated springs 2132-2138, with each spring (e.g., 2132) attached at a first end to the underside of the outer plate 2124 and at a second end to the end of the pin (e.g., 2102) opposite the cap portion (e.g., 2112). When the pins 2102-2108 are fully extended, the springs 2132-2138 are compressed against the underside of the outer plate 2124. The springs 2132-2138 thus provide a tensive force on the pins 2102-2108 as to draw the pins toward the interior of the object being formed.

The movement of the reset plate 2130 and the operation of the clutch mechanism can be coordinated by a controller 2140 to adjust the position of the pins 2102-2108. The controller 2140 can provide information relating to the desired pin positions to the projector. The reset plate 130 can be incrementally withdrawn toward the interior of the object. In an exemplary embodiment, the reset plate 2130 withdraws in increments equal to the spacing between the grooves on the pins 2102-2108. After each retraction of the plate, the clutch mechanism 2126 can be selectively activated to release one or more of the pins, while leaving others secured. The tensive force provided by the springs 2132-

2138 pulls the ends of the released pins flush against the reset plate 130, such that the released pins retract to a uniform level defined by the position of the reset plate. The secured pins remain at their previous level. The pins are then resecured by the clutch mechanism, and the plate is retracted by another increment. This process is repeated as the reset plate 2130 retracts to leave each pin at a desired level of extension.

In another embodiment, the pins pass through respective apertures in a stationary, outer plate housing a first portion of a clutch mechanism that acts to adjust the pins into desired positions. In an exemplary implementation, the first clutch portion can be piezoelectric restraints for the plurality of pins. In a default position, a given restraint loops around its associated pin, but allows the pin to move freely. Upon the application of an electrical current, the restraint contracts as to physically contact its associated pin at one of a plurality of evenly spaced grooves on the pin. This fixes the pin to the outer plate, maintaining the pin at a stationary position. The spacing of the grooves corresponds to a desired resolution of the 3D object being formed. The pins also pass through respective apertures in a moving plate which can be moved by a motor and belt arrangement. The moving plate houses a second portion of the clutch mechanism with piezoelectric restraints for the plurality of pins. The movement of the moving plate and the operation of the first/second clutch portions can be coordinated by a controller to adjust the position of the pins. The moving plate oscillates in a direction normal to the outer plate and a base plate between a first position, closest to the base plate and a second position, closest to the outer plate. In an exemplary embodiment, the first position and the second position are separated by a distance equal to the spacing between adjacent grooves. The pins begin in a default position, fixed to the outer plate by the first clutch portion. In an exemplary embodiment, the default position of the pins is a fully withdrawn position (e.g., the first clutch portion engages the uppermost groove of each pin). Since the default position of the pins is known, the controller can determine the distance between the default position and a desired position as a number of increments, as defined by the groove spacing of the pins. The controller can thus select one or more pins to extend by one or more increments. While the moving plate is in its first position, the selected pins are released by the first clutch portion. Simultaneously, the second clutch portion engages the selected pins, such that the pins are fixed to the moving plate. The moving plate can then be moved to its second position. Once the plate reaches the second position, the second clutch portion releases the selected pins, while the first clutch portion reengages the pins. It will be appreciated that the motion of the moving plate can be controlled by the controller such that the first clutch portion can engage the pins at a groove one increment below the default position. Accordingly, the selected pins are extended by one increment. This can be repeated a number of times, to allow one or more pins to be moved to a desired position up to a maximum extension. The final position of each pin will be determined by the number of times the first and second clutch portions are activated for the pin. This can be controlled by the controller according to the desired position of the pin. Once the pins have been positioned, the controller can direct the object fabricator 1006 to copy the 3D object formed by the pin grid 3D shape generator.

In another exemplary clutch mechanism, a pin can be encased in a solid restraining material having a low melting point. For example, the restraining material can be an alloy of lead and one or more other metals. The restraining material is contained in a container having a relatively high melting point. The clutch mechanism disengages by applying heat from a heat source to the restraining material in order to bring it to a liquid state. The heat source can be applied by a laser apparatus (not shown) directed on the restraining material or by a heating element associated with the container. In an exemplary implementation, the container is the heat source, producing resistive heat upon the application of an electrical current. While the restraining material is in a liquid state, the pin can move freely through the aperture. Once the heat source is deactivated, the restraining material cools and returns to a solid state, restraining the pin.

In yet another exemplary clutch mechanism, a wire has shape memory properties is looped around a pin. The material with shape memory properties has the ability to return to an imprinted shape when heated. A desired shape can be imprinted into the material by molding the material at a high temperature and maintaining the desired shape as it cools. Below a threshold temperature, the material is relatively flexible and can be deformed away from the imprinted shape with relative ease. Once the material is heated above the threshold temperature, however, it reverts back to the imprinted shape with some force. In an exemplary implementation, the wire is a formed from nitinol, an alloy of nickel and titanium. The wire is shaped such that the loop is opened around the pin and the pin can move freely through the loop. A current can be applied to the wire to heat the wire via resistive heating to a temperature greater than its threshold temperature. This causes the wire to return to its imprinted shape, engaging the pin as the loop closes. The wire returns to its imprinted shape somewhat forcefully, such that the tensive force on the ends of the wire is insufficient to restrain it. In an exemplary embodiment, the wire is looped around a groove in the surface of the pin to facilitate engagement of the pin. When the current is no longer applied, the wire 352 cools and returns to its more malleable state. Once the wire cools below threshold, the tensive force applied can once again deform the wire into an open shape, releasing the pin.

Form and Operation of Particle-Filled Containers

FIG. 14A-14D show a first container embodiment, a master shape and a vacuum cap, and further show a sequence of operations to create a shaped impression, complementary to the master shape, in the surface of one elastomeric membrane face of the container. Turning now to FIG. 14A, a container 5 is shown with a rigid container frame 10 and elastomeric top and bottom membranes 20 and 25, resting on a base 13 which separates the bottom membrane 25 from contact with any surface that the base 13 and the container 5 rest on. The top membrane 20 is bonded to a perimeter frame 17 so as to have an air-tight interface between the container frame 10 and the membrane 20. The container frame 10 is affixed to a continuous vacuum-activated seal 30 which is bonded to the container frame 10. The seal 30 is resilient and acts much like a suction cup to hold the perimeter frame 17 to the container frame 10. The bottom membrane 25 is bonded directly to rigid container frame 10 since the membrane 25 is not a working surface wearer to damage, in contrast to the working surface of membrane 20 which is subject to damage. In one embodiment, the bottom membrane 25 can be affixed by a perimeter frame and vacuum seal as described above. In yet another embodiment with more complexity, mechanical clamps and a pressure seal can be employed to affix either top or bottom membranes. Tubes 40, 50 and 60 penetrate a toolbed or a container frame 10. The tube 40 communicates with a seal 30 through an opening 45, and the seal 30 affixes the membrane 20 to the container 5 by a vacuum (indicated by arrow 43) acting through the tube 40. The vacuum seal 30 can be inactivated by introducing air through the tube 40, allowing the membrane 20 and the frame 10 to be removed in order to insert or remove a volume of particles from the container 5, or to replace a damaged membrane 20 or internal screen element. The tube 50 communicates with a main particle screen 55 which is overlaid with a volume of particles 80. Arrow 53 indicates the flow of liquid into the particle volume through screens 55. The particle screens 55 serve to hold all particles in the container 5 while allowing liquid to flow in and out of the particle mass. There is a double layer construction of both screens 55 with the tubes 50 and 60 communicating between the layers. The particles cannot penetrate the outer layers of the screens and so do not move into the tubes as air is evacuated or liquid extracted. The extensions have perforations that enable distributed liquid flow along the length of the tube inside the screen. The tube 60 communicates with a rim evacuation screen element 65 which follows the entire inside upper perimeter of frame 10 and is likewise perforated along its length within element 65. Arrow 63 points outward to indicate deaerating vacuum force acting on the container volume via the evacuation element.

Turning now to the top of FIG. 14A, a vacuum cap 90 is shown with a continuous flexible or elastomeric membrane 95 bonded to another perimeter frame 100, the frame also having a continuous vacuum-activated seal 105 bonded to the frame 100. The seal 105 is identical in design and function to the seal 30. The vacuum cap 90 has a tube 110, which communicates with the vacuum seal through an opening 115, and a tube 125 which in turn communicates with the underside of membrane 95 through a port 120.

A master shape 130 is shown resting on membrane 20. The master shape will used to form a shaped impression in the membrane as described next. To prepare for the forming process, a membrane 20 is sealed to the container; air is removed from the volume of particles as shown by arrow 63; and liquid is introduced into the particle volume as shown by arrow 53. Liquid flow is cut off when there is sufficient liquid to allow particles to move in relation to adjacent particles as displacing force is exerted on either the top or bottom membrane of the container. More details on the reformable manufacturing are disclosed in commonly owned patents to Jacobson et al including U.S. Pat. No. 6,398,992 and Pub. No. 20050035477 and 20070187855, the contents of which are incorporated by reference.

FIG. 14C shows a side view of the container frame 10 with a vacuum cap 70 resting over the master shape 130 prior to being sealed against the membrane perimeter frame 15 to which the membrane 20 is bonded, with the membrane affixed using the seal 30 to the container frame 10. The master 130 is resting on the unformed surface of membrane 20 with the movable particles between membranes 20 and 25.

FIG. 14D shows a cutaway view with the vacuum cap 90 affixed by the seal 105 against the perimeter frame 15 by vacuum through the tube 110 as shown by an arrow 113. In addition the space between the vacuum cap membrane 95 and the top membrane 20 has been evacuated through the tube 125 as shown by an arrow 127. The vacuum cap membrane 95 is pressed down against the master shape 130 and against the surface membrane 20 by atmospheric pressure which also acts oppposedly against container bottom membrane 25. Liquid is then extracted by a pump or vacuum from the particle volume through a tube (not shown) through the particle screen 55, causing atmospheric forces acting on bottom membrane 25 to pack the particles against top membrane 20 which is forced against the master shape since air has been evacuated from between the vacuum cap membrane and top membrane 20. Any leakage of air into the container, which would add atmospheric pressure back to the container and so reduce the packing force on the particles, can be removed by continuing vacuum extraction of liquid through particle screens 55 or by vacuum extraction through the perimeter evacuation screen element 65.

When the master shape 130 is removed from the surface of the membrane 20, an impressed shape 135 remains which is complementary to the shape 130. The differential pressure on the container by vacuum extraction is continued, thereby maintaining opposed atmospheric forces that act to keep membranes 20 and 25 pressed against the particles and so immobilizing them to keep the impressed shape stabilized. In form the seal is a continuous channel with the legs angled outward. The channel has a single opening and a vacuum and vent tube connected to it as described with reference to FIG. 14A. The material of the seal is resilient since the legs will be pressed against a surface and must conform to and seal against the surface. The legs are separated by a sufficient distance that they will be pressed into contact with the surface by atmospheric pressure with a greater force per unit area than atmospheric pressure. In function, when the legs of the channel are pressed against a smooth surface and the vacuum introduced inside the channel, the seal legs deform against the surface and the deformed area is substantially less than the area inside the channel. In experiments a ratio of deformed area to inside area of 1 to 2 has been shown to be very effective in sealing against a smooth surface if the durometer of the seal's elastomeric material is around 40. In operation the seal is simply placed against or gently pressed against a smooth air-impermeable surface. A vacuum is introduced through the tube, extracting air from within the seal and so enabling atmospheric pressure to force the seal against the surface. Any leakage from atmosphere outside the seal is scavenged by the vacuum and so does not enter the volume inside the perimeter of the seal even if a full vacuum is imposed on that volume. To release the seal air is introduced via the tube or a small blade can be slipped between the seal and surface to break the internal vacuum.

The particles can be a reversible state-changeable mixture having a plurality of solid bodies and a carrier medium, with the carrier medium filling any voids or interstices between the bodies. Within the mixture, the solid bodies can be caused to transition from a formable state, preferably a near-liquid or fluent condition of mobility, to a stable, force-resisting condition through introduction and then extraction of a slight excess quantity of the carrier medium beyond that required to fill the interstices of the bodies when closely packed. In most embodiments, the carrier medium is a liquid preferably excluding any air or other gases from the mixture, and most of the discussion will revolve around such embodiments. However, some embodiments use a carrier medium that is a liquid-gas froth.

The mixture can be rapidly shifted from a formable (preferably near-liquid or fluent) state to a stable force-resisting state and back again to the formable state, through slightly altering the carrier-solid proportions of the mixture, and the system further provides methods and apparatus for using the mixture. Embodiments are characterized by one or more of the following advantages: the ability to pressurize a mixture and drive it against a complex surface as if it were a liquid; the ability to create a "near-net" or extremely accurate representation of a shape due to the negligible volumetric change that accompanies a state change; the ability to effect the state-change with a very small volume of single-constituent transfer and with consequently small actuation devices without the need for a vacuum pump, without chemical reactions, and with no need for thermal or electrical energy to be applied to the mixture; the ability to greatly alter the volume of any elastic or otherwise dimensionally changeable container, envelope or chamber through the free-flowing transfer of the mixture from one container to another; and the ability to tailor the mixture to satisfy a wide variety of physical specifications in either the flowable or the stable state.

The mixture can be used in reformable molds or other shaping tools, and in reusable templates that capture the dimensions of impressed shapes for transfer to a mold. The mixture can also be used in any product or shape that benefits from the incorporation of arbitrary reformability or precise reconfigurability. The mixtures further provide useful properties for use in a wide range of shock-absorbing, leveling, protective and supportive elements or apparatus.

The mixture in its formable state may be loosely compared to quicksand, while the mixture in its stable state may resemble hard-packed sand or even cement, with the transition being caused by the transfer of a relatively small amount of liquid. Hence the mixture, while in the formable state, includes enough liquid to fill the interstices between the nested solid bodies, and an excess amount of liquid that is referred to as the transition liquid. In the stable state the transition liquid is absent and the bodies are completely packed or nested.

In preferred embodiments the solid bodies are uniform, generally ordered, and closely spaced, with the predominate mass of the bodies close-packed and touching. To create mobility, the transition liquid is introduced in just-sufficient quantity to create a fluent condition by providing a clearance between some of the bodies, which clearance permits the introduction of at least two simultaneous slip planes between ordered masses of the bodies at any point in the mixture. The bodies themselves separate freely from one another under movement of the liquid and without turbulent mixing, and shift relative to one another generally in ordered bulk masses. The bodies should be of a density that is close enough to that of the liquid to permit flow of the bodies along with the liquid, or should have a size or structure that facilitates movement of the bodies along with the liquid.

In an embodiment, the surface of the mixture while in the formable state is first made to conform to a desired shape. The bodies in the mixture are then caused to transition from the fluent condition to the stable condition through extraction of the transition liquid. This extraction removes the clearances required to provide slip-planes between ordered masses of the solid bodies, thereby causing the bodies to make nested, packed, interlocking or otherwise stable consolidated contact. The mixture, now in the stable state, has a surface that conforms to the desired shape.

The mixture can be used in molds, templates or other products through holding the mixture in, or transferring quantities of the mixture while in the fluent condition into and out of variable-contour or variable-volume containers or chambers. The mixture can be stabilized by removal of the transition liquid, which may cause an elastic membrane to be pushed against the consolidated bodies by ambient pressure, or by transition liquid removal that causes the solid bodies to pack together under liquid tensile forces, thereby creating an ordered, deformation-resisting structure through surface friction or through surface adhesion of one body to another.

In certain embodiments, the mixture can be held inside a container or transported into a container with a flexible, elastically deformable and stretchable wall. The process then extracts the transition liquid from the mixture so as to cause body-to-body contact and force-resisting stability through pressure external to the container acting on the confined, ordered, abutting bodies. Transfer of fluent mixture into and out of the containers, or displacement of mixture within the containers can be accomplished by pressure forces within the mixture, with these forces being distributed uniformly throughout the mixture by the liquid carrier medium.

This distribution of uniform pressure against the surface of each body, coupled with the clearance volume furnished by the transition liquid, assures that the bodies are not forced against one another while the mixture is in the fluent condition. This elimination of body-to-body compression forces in turn prevents the bodies from sticking together and resisting displacement while the mixture is in the fluent condition. Pressure forces in the liquid can be exerted through pressing a shape against an elastic, stretchable membrane that constitutes at least one surface of a chamber substantially filled with the fluent mixture, or such forces within the liquid medium of the fluent mixture may be induced by a two-way pump or other transfer system.

The bodies themselves may have various geometries and may be provided within a state-change mixture in one uniform type, or there may be two or more types or sizes of bodies dispersed or layered within a mixture. For example, spherical bodies of one size might have smaller bodies filling the interstices between the larger bodies, or a layer of short fiber bodies might float above a layer of spherical bodies. Flake-like bodies can be also be used, in which case the flat faces of the bodies can be pressed against one another to create a force-resisting body mass. The flat faces provide many times the contact area of abutting spheres, with accordingly higher friction or adhesion potential when consolidated against one another. If the flakes are in the form of a laminate that has one side heavier than the carrier medium and one side lighter, and if the flakes are closely spaced and in a medium which suppresses turbulence and solid body tumbling, the bodies will tend to be supported in, and to be consolidated in, an ordered parallel configuration. In this case, as with the spherical bodies, the transition liquid quantity will be just sufficient to create shear motion of body masses under low displacement forces.

Mixtures with more than one type or size of body can be used with the bodies either intermingled or layered separately, as by differing densities or the inability of bodies of one layer to pass through bodies in the adjacent layer. Bodies of different sizes or types may also be separated from one another by flexible or extensible porous materials or fabrications that allow passage of liquids but not of the confined bodies.

The degree of accuracy or irregularity on the surface of a stabilized mass of the mixture is dependent upon the relationship between the fineness of the bodies and the dimensions to be captured, a covering membrane's thickness and conformability, and the size and degree of regular packing order of a state-change mixture's solid bodies. If the bodies are very small compared to the contours of a shape that is to be replicated, or if the interstices between larger bodies in the mixture are filled by such smaller bodies, the mobile solid bodies of the mixture will consolidate and assume a near-net shape relative to any impressed shape when the transition liquid is extracted from the mixture.

In additional embodiments, the mixtures are stored external to one or more molds, tools or fixtures, and are selectively introduced, stabilized and made fluent again in the tools. Formulas of the mixtures or solid bodies and liquids of the mixtures may be stored separately, and may be mixed or separated as required for effective operation of separate elements of a forming or tooling system.

In yet other embodiments, flexible elements containing state-change mixtures are used to capture exterior or interior contours of a shape and to transfer the contours to other state-change elements. Through such "templating" operations a negative of a shape or surface may be produced and then a shape or surface identical to the first may be produced by forming the surface of a mixture against the transfer template. Individual elements might also be used to transfer portions of one shape to another shape and so create variations that combine the contours of two or more shapes into a single shape.

In still other embodiments, several elastic, extensible elements filled with state-change mixtures slide freely upon one another and relative to the contained mixtures in order to conform to highly contoured shapes. These embodiments would be used when the elastic stretch of a single membrane element is not sufficient to capture details of a shape.

Further embodiments include methods of displacing fluent mixtures within variable-volume flat elastic envelopes by pressing the envelopes against shapes with exterior air or liquid pressures, or pressing with physical elements such as bundles of rods or fingers that slide relative to one another. The pressing force pressurizes the liquid carrier medium and causes the envelopes to extend and conform to the shapes as the contained fluent mixtures flow within the envelopes under the uniformly distributed pressure forces within the liquid. Embodiments also contemplate the creation of hollow voids within a mixture-containing envelope, with the impressed shape causing the collapse of the voids so that the mixture need not be pumped into and out of a chamber to permit capture of a shape.

Yet other embodiments include methods for creating a sculptable condition in specific state-change mixtures through placing the mixtures in a quasi-stable state. The solid bodies are held in contact by extraction of a portion of the transition liquid, yet have sufficient lubricity or low contact friction to be displaced relative to one another by externally imposed forces. The bodies can be displaced into voids created within a mass of the quasi-consolidated mixture, or can be progressively displaced along the surface of the mixture from one region of the mass to another. In some embodiments, properties of flow of the mixture and the resistance to deformation of the abutted bodies are predetermined so as to be a function of the imposed external forces, and so to be subject to variable control that allows intermediate quasi-stable, sculptable or displaceable conditions within or on the surface of the bulk mixture.

State-change mixtures may also use solid bodies along with a state-changeable liquid carrier medium. The method for changing the mixture from fluent to stable and back again is, as described above, through transfer of a small amount of excess liquid; however, the mixture can be further solidified by changing the state of the carrier medium from liquid to solid.

In yet another embodiment, a state-change mixture is consolidated within a mold chamber and the liquid carrier or a second liquid component is circulated while held to a pressure below ambient. Through heating and cooling of the circulating liquid, the mold itself can be heated or cooled.

Still another embodiment of the state-change mixture has solid bodies that are hollow and very light, and a carrier medium comprising a liquid-gas froth of similar density. The froth is destroyed when extracted since the gas within it expands and separates from the liquid component; then the froth is reconstituted from the liquid and gas and reintroduced into the body mass to recreate a fluent mixture. The liquid component of the froth may be a solvatable (solvent-releasable) adhesive that can be dried to hold the consolidated bodies together and then re-dissolved by the frothed carrier medium. Very light bodies can also surrounded by a denser liquid, with the mixture likewise becoming fluent and then stabilized with transfer of a small quantity of transition liquid; however, the tendency of the bodies to adhere together under contact pressure is preferably countered, or liquid-like transfer of the mixture, especially through small lines or passages, becomes difficult if not impossible.

In additional flat envelope embodiments internal and external elements improve their functioning as lightweight tooling and templates. Included are methods to support these mixture-containing envelope structures, both internally with flexible reinforcements and externally with tubular 'foot' structures that also contain state-change mixtures. The flat envelopes may also be backed or supported by liquids or dry media with the ability to capture precise impressions of a shape with the ability to be switched from a liquid-like state to a firm state, or even to a fully hardened state that resembles concrete yet can be returned to a formable condition.

The state change from liquid-like to solid-like properties within the mixtures is effected by the transfer of a small amount of excess carrier medium, the transition liquid, into and out of the mixtures. When the transition liquid is present, preferably in just-sufficient quantity to create the degree of support and clearance that provides for at least two slip-planes, the solid bodies have a degree of mobility similar to that of the liquid medium of the mixture. The slip-plane condition of mobility can be generated through very small liquid pressure differentials or through externally imposed forces that displace the carrier liquid and the supported bodies along with the liquid. Ordered bulk masses of the bodies can shift relative to other ordered masses at any point within a continuous volume of the mixture, and the location of the slip-planes can fluidly shift under any slight differential force transferred from one body to another. It is preferred to prevent frictional contact between bodies during such force transfer by having the liquid medium of the mixture furnish a viscous or ' streaming' resistance to contact, and also for the medium to furnish a degree of body-surface lubrication so that light body contacts do not create friction between bodies.

Lubricity under high contact forces, as is required for many lubricating media, is not necessary within the mixtures since the bodies are in effect free-floating during flow, with any imposed liquid pressure forces being uniformly distributed against the surface of each body. For example a nearly ideal aqueous liquid medium can be formed by dissolving a small quantity of a soluble long-chain polymer such as polyethylene oxide into water. The medium carries solid bodies of a similar density without turbulence and friction-producing contact, allows the bodies to make non-lubricated surface contact when the medium is extracted, and causes the bodies to readily separate when the transition liquid is reintroduced.

When the transition liquid is extracted so that the solid bodies are in a stable configuration with ordered, packed and consolidated contact, the degree of resistance to externally imposed forces depends on such tailorable, engineered physical properties as body shape, body elasticity and compressibility, body surface properties of roughness, smoothness or natural molecular adhesion, residual adhesiveness or lubricity of the liquid medium on the contacting surfaces, surface tension of the medium, and variations of liquid medium or body properties with changes of temperature or pressure; alteration of the resistance properties through replacement of the first liquid with a second liquid medium, rinsing of the bodies and the first medium with a second or sequential liquid media, vapors or gaseous fluids; and any other engineered variations in the bodies and first liquid medium, and in other sequential introductions of various fluids into the mixtures or through the consolidated bodies. Any adhesive or clinging contact between the bodies is preferably relieved through polar molecular action of the first liquid medium, or through an intermediary treatment with other liquids or fluids prior to reintroduction of the first liquid medium.

The container works with quickly reversible state-change mixtures which can be rapidly shifted from a near-liquid or fluent state to a stable force-resisting state through slightly altering the liquid-solid proportions, and the system further provides methods and apparatus for utilizing the mixtures. Embodiments are characterized by one or more of the following advantages: the ability to pressurize a mixture and drive it against a complex surface as if it were a liquid; the ability to create a "near-net" or extremely accurate representation of a shape due to the negligible volumetric change which accompanies a state change; the ability to effect the state-change with a very small volume of single-constituent transfer and with consequently small actuation devices, with a low-energy mechanical actuation, and without requiring a vacuum pump, thermal, chemical or electrical energy to be applied to the mixture; the ability to greatly alter the volume of any elastic or otherwise dimensionally changeable container, envelope or chamber through the free-flowing transfer of the nearly solid mixtures from one container to another; and the ability to tailor the mixtures to satisfy a wide variety of physical specifications in either the flowable or the stable state.

The mixtures can be employed in reformable molds or other shaping tools, and in reusable templates which capture the dimensions of impressed shapes for transfer to a mold. The mixtures can also be used in any product or shape which benefits from the incorporation of arbitrarily reformability or precise reconfigurability. The mixtures further provide useful properties for but are not limited to application in a wide range of shock-absorbing, leveling, protective and supportive apparatus.

It can be appreciated that there are numerous variations of containers and varied combinations of containers which can be employed either to form a surface which is complementary to the exterior surface of a master shape in part or in whole, or to form a surface or surfaces complementary to the interior contours of a hollow master shape or master cavity. For instance more than one container of the first type (rigid frame) or second type (flexible-edge) can be employed to form a continuous surface complementary to a master shape's surface, with the elastomeric membranes of the containers either overlapping or being abutted together. Containers of the second type may also have a membrane and particle configuration that allows two or more of the containers to be "tiled" together to form a continuous surface of particle-backed membranes. Likewise two or more containers of the third type can be employed together to form a shape complementary to the interior of a master cavity.

Presented below are examples discussing a method of treating a subject having or at risk of having or having a viral infection, and devices contemplated for the discussed applications. The following examples are provided to further illustrate the embodiments of the present invention but are not intended to limit the scope of the invention. While they are typical of those that might be used, other procedures, methodologies, or techniques known to those skilled in the art may alternatively be used.

Example 1

Rational for the Use of 4-Mu to Treat Covid-19 Patients

COVID-19 induced a sudden rise in hyaluronan levels leading to significant impairment of normal lung function primarily because of a rapid and excessive water accumulation in the lungs. By causing a rapid accumulation of water in the lungs, which results in respiratory failure, hyaluronan is a primary driver of COVID-19 morbidity and mortality.

Figure 1:
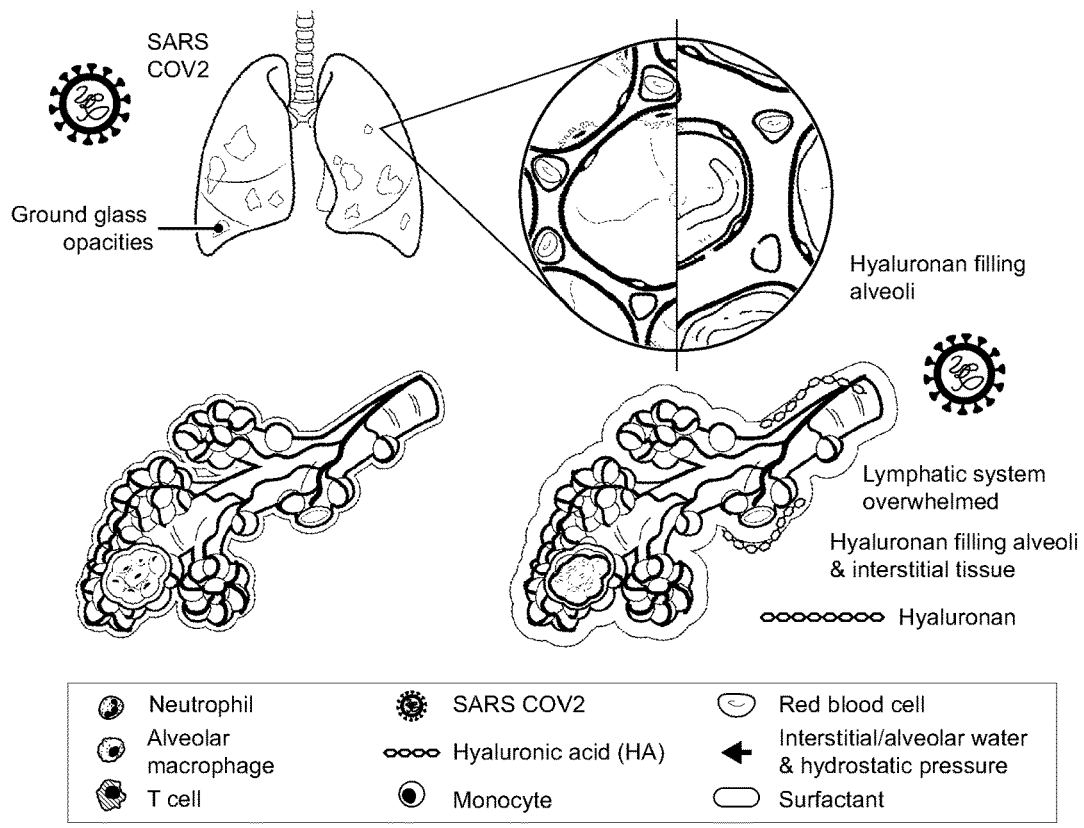
Figure 1:
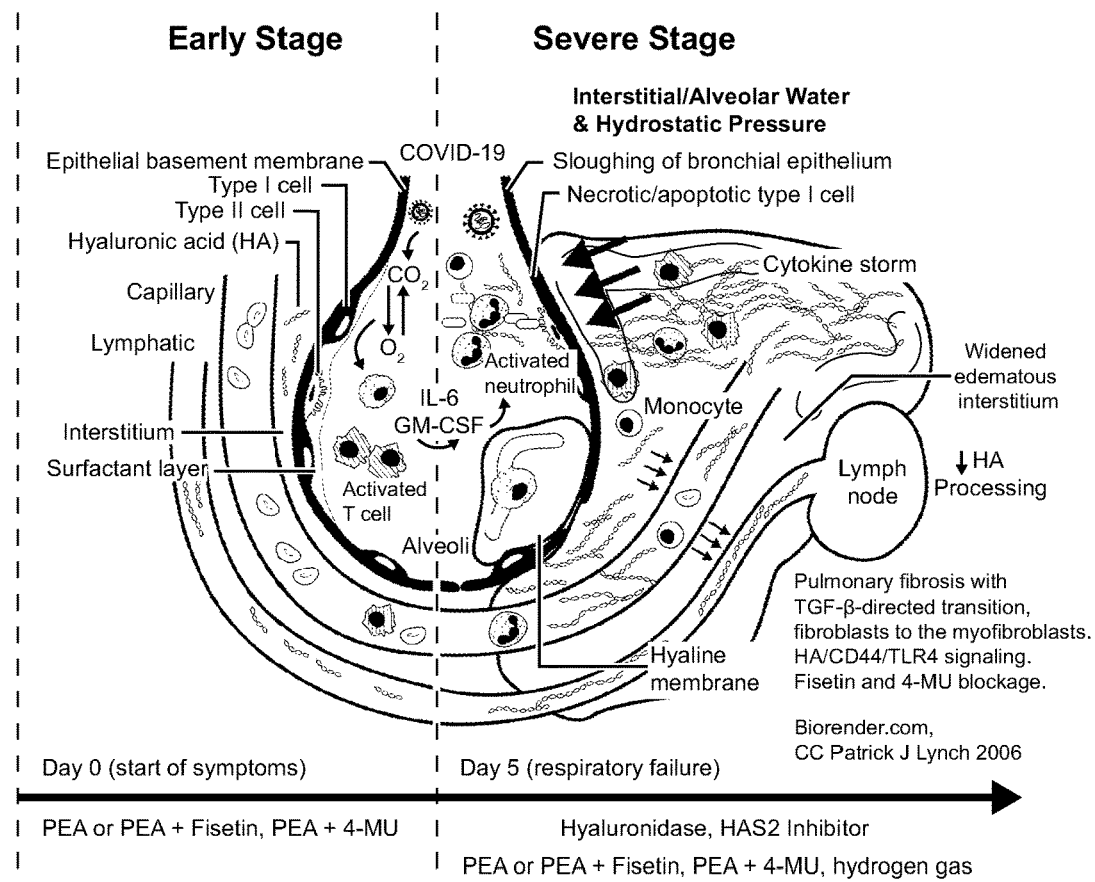

As illustrated in FIG. 1, a similar treatment method that addresses the proximal cause of death in COVID-19, SERS, MERS patients is rapid, massive lung, spleen, and vascular damage as detailed by numerous autopsy reports can be provided.

Numerous autopsies report the lungs of victims to be "heavy" weighing upwards of 2000-2500 grams; the normal weight of the lungs being in the range of 1000 grams. The spleens are reported to be hemorrhagic and atrophic.

With COVID-19, widespread intravascular coagulation and necrosis are common findings. Cardiac and renal finding are much the same. All of these finds are quite significant and can be explained on the basis of the underlying pathophysiology of Induced Hyaluronan Storm Syndrome (IHS). IHS defines the specific cause, pathways, treatment targets, clinical approach, and supportive interventions explaining the acute respiratory distress syndrome in COVID-19 and a long list of other injurious triggers affecting the lungs as well as other organ systems both Interestingly, high risk individuals who succumb to the infection do so in a very short time, often moving from the early symptoms of fever, and dry cough, to full blown acute respiratory distress syndrome, mechanical ventilation, and death in as little as 5-6 days, as shown in FIG. 1. This is in sharp contrast with the fact that the vast majority of infected individuals are either asymptomatic or have rather mild symptoms.

Patients typically have massively elevated levels of Hyaluronan (Hyaluronic Acid or HA) in their bronchial lavage (BAL) fluid and blood steam. To suppress the production of HA, the present system works by inhibiting the three isoenzymes of hyaluronan synthase-HAS-1, HAS-2, and HAS-3 with 4-MU (4-methylumbelliferone). The 4-MU (a non-toxic molecule) reduces expression of HAS-1, HAS-2, and HAS-3 (the enzymes that produce HA), and reduced levels of HA in the lungs of SEB-exposed mice and 4-MU (4-methylumbelliferone) treatment has led to a reduction in SEB-induced lung permeability, and reduced cytokine production."

Figure 2:
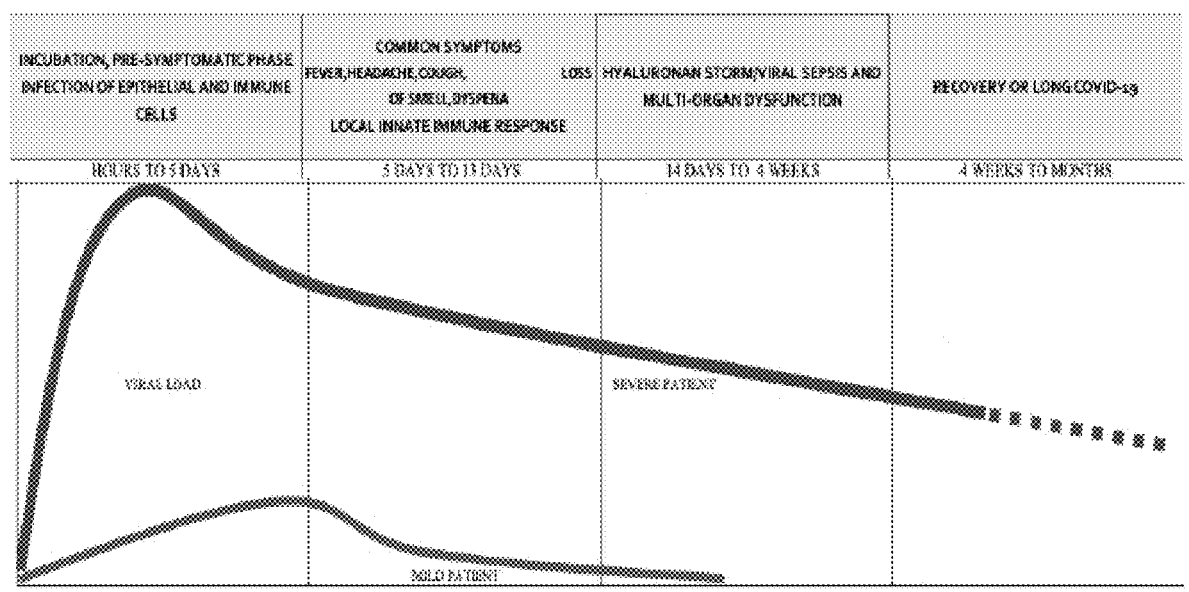

FIG. 2 offers more detail as to the use of the method in both mild and severe COVID-19 outlining proposed risk factors, relevant metabolic derangements, potential example diagnostic measures, and exemplary treatments spanning from initial exposure through resolution or Persistent Post-COVID Syndrome (PPCS). Table 2, below illustrates this detail.

TABLE 2

| DISEASE PHASE | PRE-EXPOSURE | INCUBATION, PRE-SYMPTOMATIC PHASE INFECTION OF EPITHELIAL AND IMMUNE CELLS | COMMON SYMPTOMS FEVER, HEADACHE, COUGH, LOSS OF SMELL, DYSPENA LOCAL INNATE IMMUNE RESPONSE | HYALURONAN STORM/ VIRAL SEPSIS AND MULTI-ORGAN DYSFUNCTION | RECOVERY OR LONG COVID-19 | RESOLUTION AND RE-ESTABLISHMENT OF HEALTH |
|---|---|---|---|---|---|---|
| RISK FACTORS FOR POOR OUTCOMES | YEARS AGE, SEX, RACE, OBESITY, DIABETES, CARDIOVASCLAR DISEASE, SOCIOECONOMIC STATUS, ACCESS TO HEALTHCARE, SEDENTARY LIFE STYLE, AIR POLLUTION, GENETIC FACTORS, UNKNOWN FACTORS | HOURS TO 5 DAYS INITIAL VIRAL LOAD, VIRULANCE OF SARS-COV2 STRAIN, AGE, SEX, ACTIVATION STATE AND HEALTH OF INNATE IMMUNE CELLS (MACROPHAGES). PREVIOUS EXPOSURE OR INFECTION. VACCINATION STATE | 5 DAYS TO 13 DAYS AGE OVER 70, MALE, TRUNCAL OBESITY, CYTOKINE STORM, ELEVATED HYALURONAN LEVELS. GENEIC PREDISPOSITION, CARDIOVASCULAR DISEASE. PRE-EXISTSING UNRESOLVED INFLAMMATION. | 14 DAYS TO 4 WEEKS AGE, SEX, RACE, TRUNCAL OBESITY AND ELEVATED ABDOMINAL GIRTH, DIABETES, CARDIOVASCLAR DISEASE, GENETIC FACTORS, UNKNOWN FACTORS | 4 WEEKS TO MONTHS RESIDUAL PULUMARY, RENAL AND BRAIN HYALURONAN LEVELS, SEVERITY OF INITIAL CLINICAL COURSE, PULMONARY AND RENAL FIBROSIS, AVAILABILITY OF REHABITILATIONAL SERVICES | YEARS-ON GOING AGE, SEX, RACE, OBESITY, DIABETES, CARDIOVASCULAR DISEASE, SOCIOECONOMIC STATUS, ACCESS TO HEALTHCARE, SEDENTARY LIFE STYLE, AIR POLLUTION, GENETIC FACTORS, DEPRESSION AND DISCOURAGEMENT, SOCIAL ISOLATION UNKNOWN FACTORS |
| METABOLIC DERANGEMENTS | CHRONIC UNRESOLVED INFLAMMATION, LOSS OF GLYCOCALYX, LOW GRADE ACTIVATION OF IMMUNE SYSTEM, HYALURONAN DEPOSITION, INCREASED INTRA-ABDOMINAL PRESSURE AND TRUNCAL OBESITY, COMPRESSION OF LUNG | MITOCHONDRIAL REACTIVE OXYGEN SPECIE GENERATION IN RESPONSE TO CELL INVASION BY VIRUS. EARLY ACTIVATION OF INNATE IMMUNE SYSTEM WITH GENERATION OF INTERFERON, EALRY CYTOKINES, EARLY PRODUCTION OF HYALURONAN | ACTIVATION OF ALVEOLAR AND TISSUE MACROPHAGES, DENDRITIC CELLS, TRAFFICKING OF IMMUNE CELLS TO LYMPH NODES, ACTIVE VIRAL REPLICATION, INCREASING HYALURONAN LEVELS AND INTERSTITIAL EDEMA, INCREASING CYTOKINES | PROGRESSIVE LUNG AND MULTIPORGAN FAILURE, ACTIVE THROMBOSIS, MASSIVE ACCUMULATION OF LUNG FLUID AND HYALURONAN, PROGRESSIVE RESPIRATORY FAILURE-ARDS | MITOCHONDRIAL OXIDATIVE DAMAGE, WIDE SPREAD TISSUE DAMAGE, CHRONIC UNRESOLVED INFLAMMATION DEPOSITION OF DAMAGED HYALURONAN PULMOARY, KIDNEY, LIVE, BRAIN FIBROSIS | MITOCHONDRIAL DECONDITIONING, LOSS OF MUSCLE MASS, |
| DIAGNOSTIC | WEIGHT, | REVERSE | REVERSE | CT SCAN, CHEST | CT SCAN, | MEASURES |

TABLE 2-continued

| DISEASE PHASE | PRE-EXPOSURE RISK FACTORS. | INCUBATION, PRE-SYMPTOMATIC PHASE INFECTION OF EPITHELIAL AND IMMUNE CELLS | COMMON SYMPTOMS FEVER, HEADACHE, COUGH, LOSS OF SMELL, DYSPENA LOCAL INNATE IMMUNE RESPONSE | HYALURONAN STORM/ VIRAL SEPSIS AND MULTI-ORGAN DYSFUNCTION | RECOVERY OR LONG COVID-19 | RESOLUTION AND RE-ESTABLISHMENT OF HEALTH |
|---|---|---|---|---|---|---|
| MEASURES | HEIGHT, BODY MASS COMPOSITION, ABDOMINAL CIRCMFERENCE, PULMONARY FUNCTION TESTING, CARDIOVASUCULAR FITNESS, SUBLINGUAL MICROCIRCULATION ANALYSIS | TRANSCRIPTION POLYMERASE CHAIN REACTION (RT-PCR) MOLECULAR DIAGNOSTICS | TRANSCRIPTION POLYMERASE CHAIN REACTION (RT-PCR), MOLECULAR DIAGNOSTICS, SEROLOGIC ASSAYS, CHEST CT SCAN, AI ALGORITHM USING WHOOP REAL TIME RESPIRATORY RATE ANALYSIS | X-RAY, CBC WITH DIFF, CMP, PROCLACITONIN, FERRITIN, D-DIMER, CRP, LDH, PTT, INR, CYTOKINES, OXYGEN STATURATION (SpO2), SERUM AND URINE HYALURONAN LEVEL | CHEST X-RAY, LUNG DIFFUSION STUDIES, CARDIOVASCULAR FITNESS STUDIES, MEASURES OF COGNITIVE AND PSYCHOSOCIAL WELLBEING, SERUM AND URINE AND BRONCHIAL HYALURONAN LEVELS. RECOVERY AND STRAIN MEASURES USING WHOOP TECHNOLOGY | OF WEIGHT, BMI, TRUNCAL OBESITY AND VISERAL FAT, CARDIVASCULAR FITNESS, COGNITIVE AND PSYCHOSOCIAL WELLBEING |
| INTERVENTIONS AND TREATMENTS | LIFE STYLE INTERVENTIONS, OPTIMIZED DIET AND EXERCISE. REVERSAL OF OBESITY AND DIABETES, IMPROVED AIR AND WATER QUALITY | PALMITOYLET HANOLAMINDE (PEA), PEA + 4-MU/ FISETIN IN HIGH RISK PT. | PEA + 4-MU/ FISETIN IN HIGH RISK PT., MOLECULAR HYDROGEN THERAPY PENPRAD SESSIONS DURING SLEEP AS NEEDED. | PENDRAD 12-16 HOURS/DAY, MOLECULAR HYDROGEN SUPPLEMENTATION, PEA + 4-MU/ FISETIN. SINGLE DOSE OF NEBULIZED HYALURONIDASE | PALMITOYLETHANOLAMINDE (PEA), PEA + 4-MU/ FISETIN, HYDROGEN GRADED EXERCISE PROGRAM DAILY PENDRAD SESSIONS 1-4 HOURS/DAY AS NEEDED. | REGULAR EXERCISE, OPTIMIZED WEIGHT AND BODY COMPOSITION, OPTIMIZED DIET. CONTROL OR REVERSAL OF DIABETIS |

Figure 3:
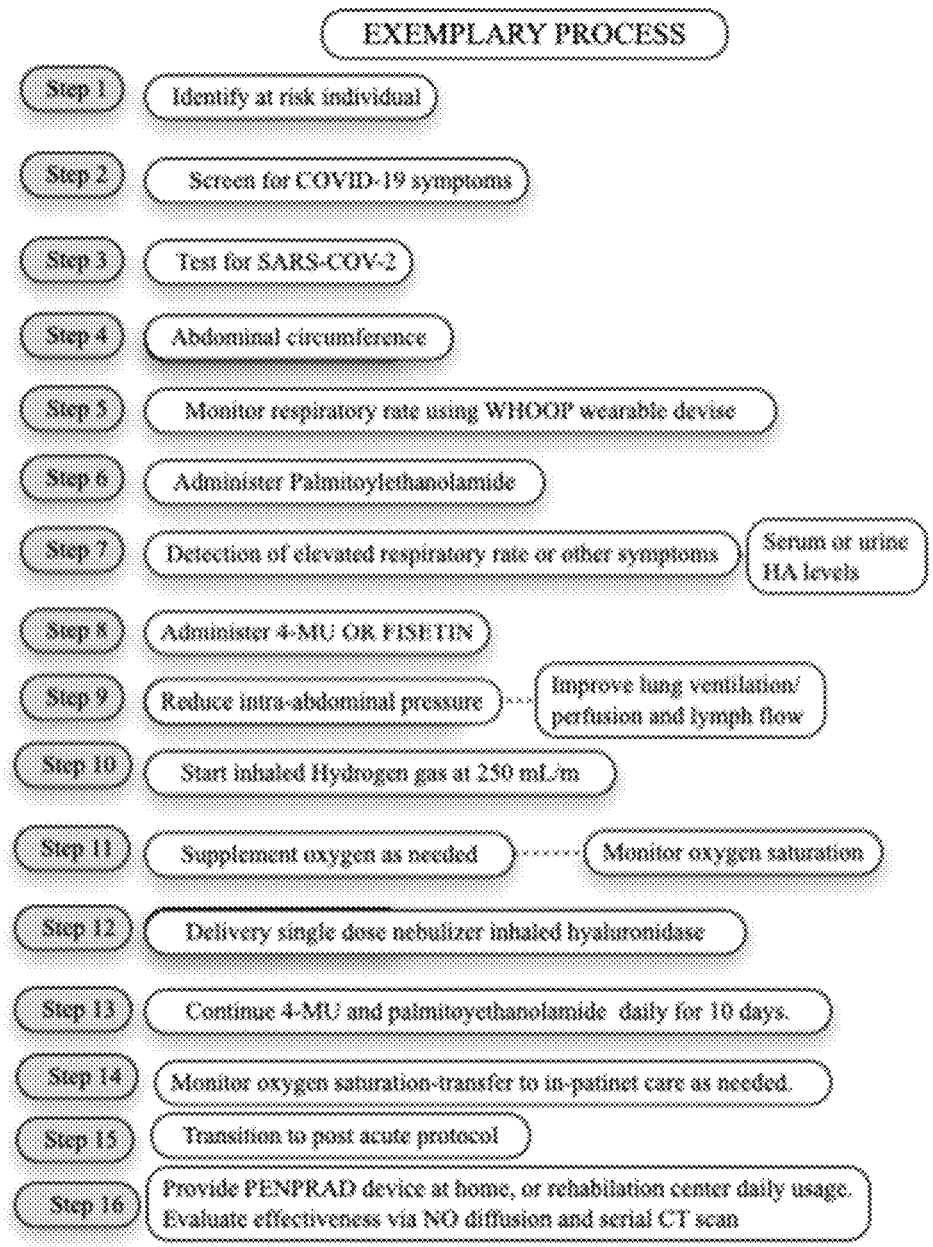

Referring now to FIG. 3, the process identifies a patient at risk for SARS-CoV-2 (1). Next the process screens for COVID-19 symptoms (2). The presence is confirmed by testing for SARS-CoV-2 (3). Patients are stratified by risk factors such as abdominal circumference (4). Patients are monitored for early signs of pulmonary compromise by WHOOP wearable devices (5). Patients are administered Palmitoylethanolamide (6). Process detects elevated respiratory rate and or elevated serum or urine hyaluronan levels (7). Patient is administered hyaluronan inhibitor such as 4-MU or fisetin (8). PENPRAD sessions are instituted to improve pulmonary ventilation and perfusion via prone positioning, intra-abdominal pressure reduction and increase lung lymphatic clearance (9). Nasal hydrogen gas is administered at 250 mL/m (10). Monitor oxygen saturation and supplement oxygen as needed (11). With dyspnea and oxygen desaturation deliver single dose of nebulized inhaled hyaluronidase. (12), Continue 4-MU, and or fisetin, and PEA daily for ten days (13). Monitor oxygen saturation-transfer to in-patients or ICU care as needed (14). Transition to post-acute care (15). Provide PENPRAD device for at home, or rehabilitation center daily usage. Evaluate effectiveness via exercise metric, pulmonary NO diffusion and serial CT scan (16).

Example 2

Portable Emergency Negative Pressure Respiratory Assistance Device

Respiratory assistance device is often a fixed device, that cannot be easily transported. In order to facilitate the issues associated with high number of patients requiring respiratory assistance at a same time (such as during a viral outbreak as seen with COVID-19), a portable emergency negative pressure respiratory assistance device is provided here.

Figure 4:
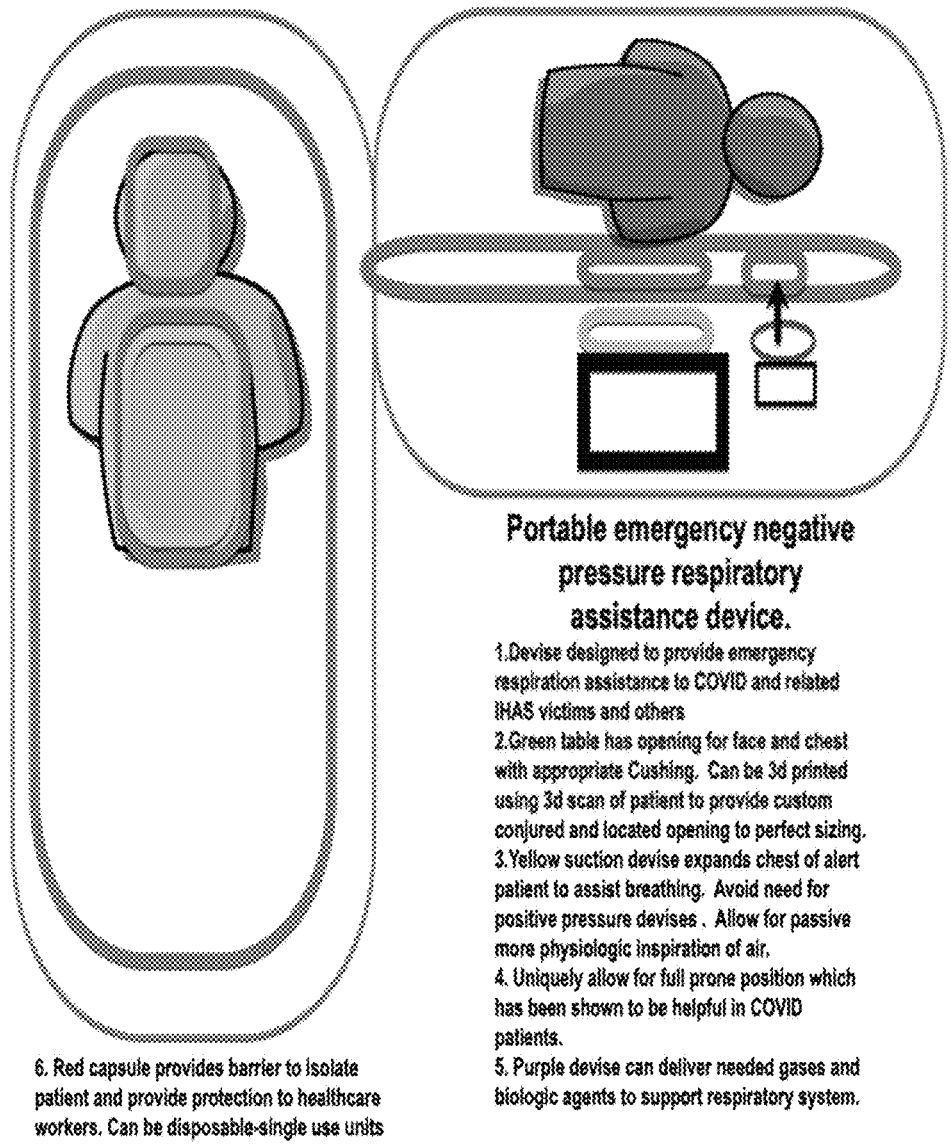

Referring to FIG. 4, an exemplary pressure driven respiratory assistance system is described. In this case, the system is a portable emergency negative pressure respiratory assistance system with a table or support surface with openings for face, chest, and abdomen and exposure, respectively. Suitable cushion or soft separation foams can be used. The table or support surface can be 3D-printed to provide custom contouring to the patient anatomical features and allow perfect sizing to the patient. A suction expands the chest and abdomen to assist breathing. The system avoids the need for positive pressure breathing assistance and allows passive physiologic inspiration of air. The system allows for a prone position which helps COVID patient recovery. A gas medical injector can be used to deliver treatment gases and biologic agents to support the respiratory system. A barrier, bubble, or clean-room housing can isolate the patient from healthcare workers. The housing can be a disposable or single-use unit that is subsequently recycled, or the housing can be decontaminated using UV rays, alcohol, soap, or other cleaning solutions that kill germs and bacteria and viruses.

Example 3

Body Support System for Automated Handling of Issues in an Intubation Systems

Intubation systems can induce issues; described herein are various system that can be implemented to support the body of patients during an intubation period.

Intubation is the process of inserting a tube, called an endotracheal tube (ET), through the mouth and then into the airway. This is done so that a patient can be placed on a ventilator to assist with breathing during anesthesia, sedation, or severe illness. The tube is then connected to a ventilator, which pushes air into the lungs to deliver a breath to the patient. This process is done for COVID-19 patients because the patient cannot maintain their airway, cannot breathe on their own without assistance, or both. This may be because they are being given anesthesia and will be unable to breathe on their own during surgery, or they may be too sick or injured to provide enough oxygen to the body without assistance. Prior to intubation, the patient is typically sedated or not conscious due to illness or injury, which allows the mouth and airway to relax. The patient is typically flat on their back and the person inserting the tube is standing at the head of the bed, looking at the patient's feet. The patient's mouth is gently opened and using a lighted instrument to keep the tongue out of the way and to light the throat, the tube is gently guided into the throat and advanced into the airway. There is a small balloon around the tube that is inflated to hold the tube in place and to keep air from escaping. Once this balloon is inflated, the tube is securely positioned in the airway and it is tied or taped in place at the mouth.

Figure 5A:
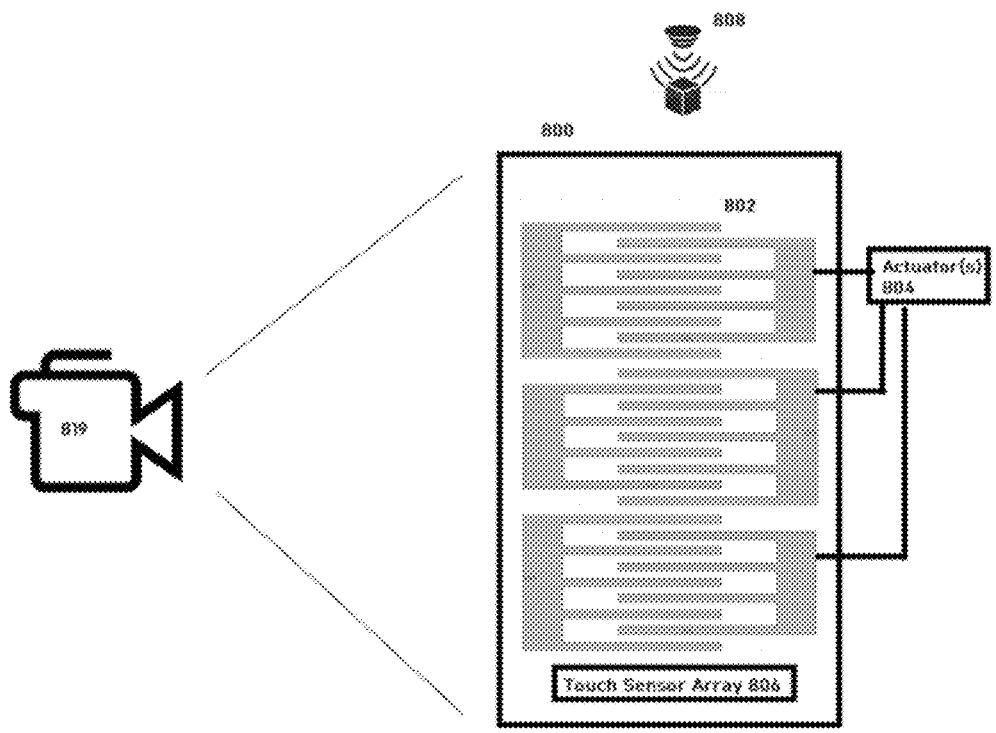
FIG. 5D shows a schematic representation of a touch sensor.
Figure 5B:
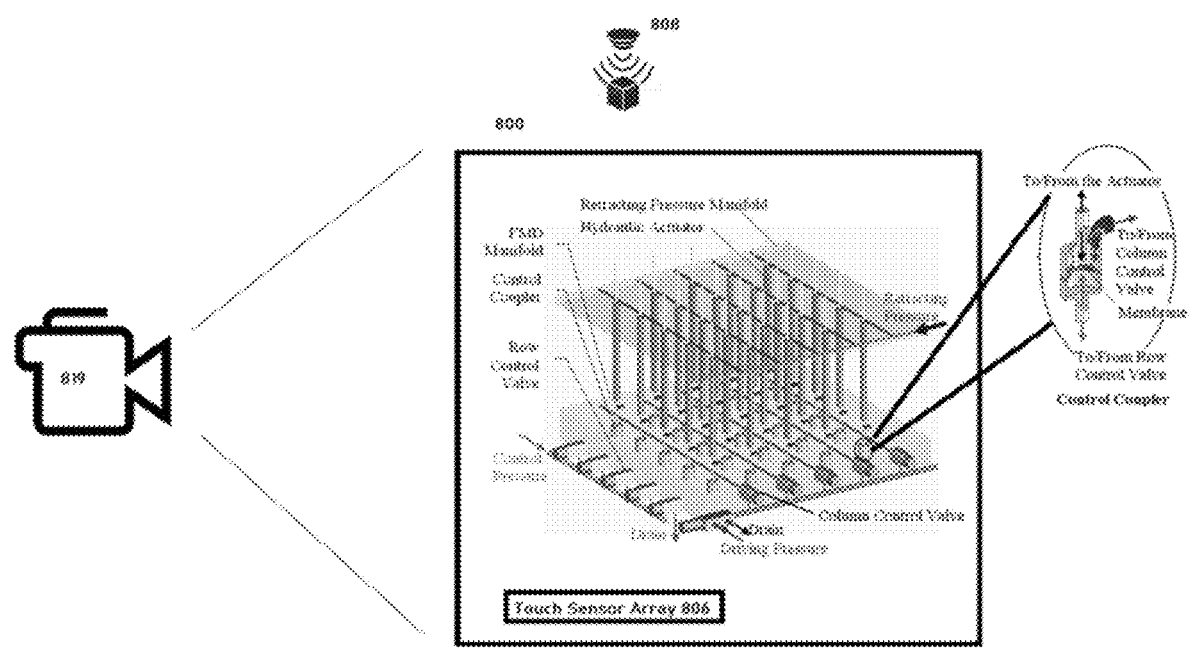
Figure 5C:
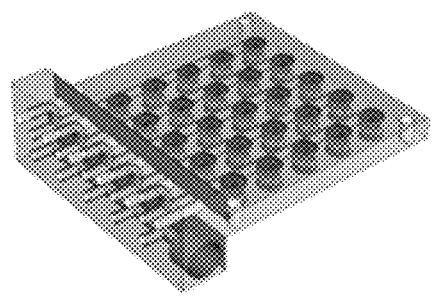
Figure 5D:
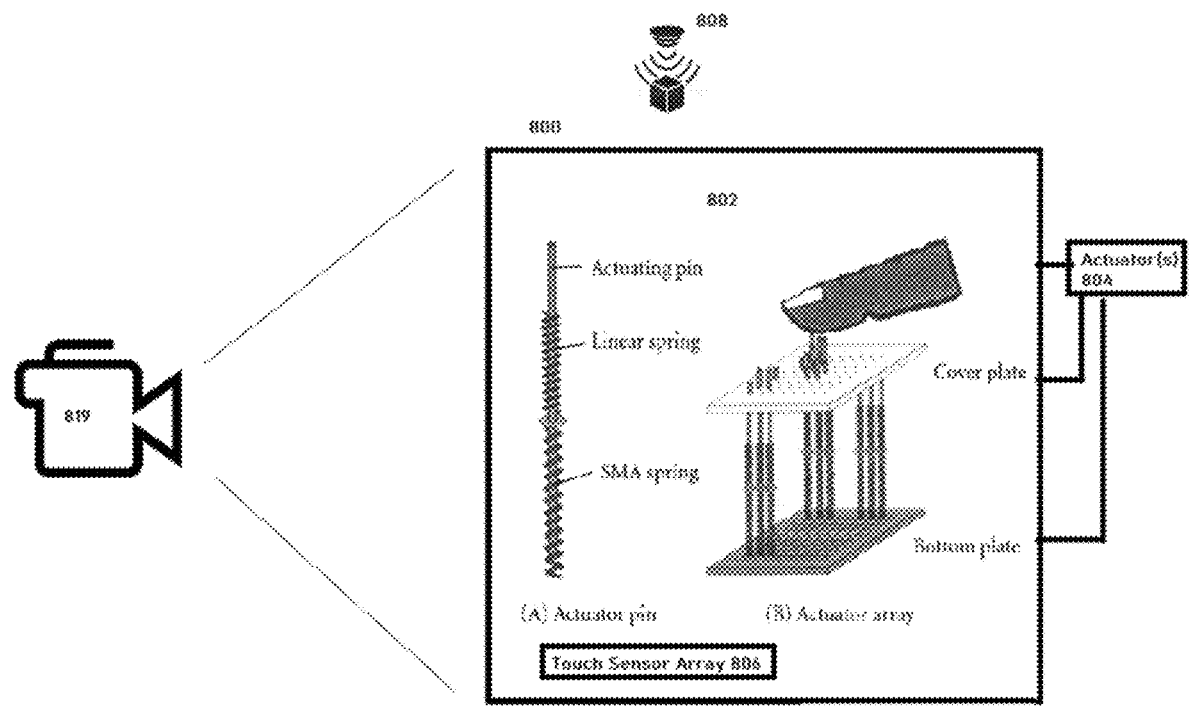

FIGS. 5A-5C show various exemplary body support system for automated handling of issues in an intubation system including endotracheal tubes or lines. The system also reduces risks to patients from extended resting on the mattress. Input is provided to hospital IT systems to reduce nursing or staff workload. Each system in FIG. 5A, FIG. 5B and FIG. 5C performs automated handling of bed sores by using an array of actuators for repositioning the patient through frequent turn and change of patient position. The system automatically repositions the patient depending on sensed patient condition and the quality of the surface of the bed mattress. The actuators also can help the patient sit or lie in a way that protects vulnerable skin. An exemplary bed is specifically designed to accommodate the human body in the prone/face down position and address the problems associated with using a normal bed. This is important for treating COVID-19, among others. An array of sensors 806 can be provided to detect patient position. Other sensors include wireless sonar/radar sensors 808 and camera sensors 819, all of which can be used singly or in combination with other sensors to increase accuracy of patient bed position detection. The sensors can include a pressure sensitive surface or mattress to monitor pressure spots and "alert" staff of the need to turn patients.

Turning now to FIG. 5A, a smart bed 800 is shown. The bed 800 includes an array of interdigitated bed sections 802 that is actuated by one or more actuators 804 to change the surface level of the mattress. A plurality of sections 802 enables fine grained change in sectional elevation so that the patient position can be adjusted under processor control. The bed 800 provides an array of cells that "float" the patient on a constant stream of air. The result is that moisture and heat are dissipated, allowing the skin to "breathe" properly. Friction and shear are vastly reduced, preventing the breakdown of the skin and the formation of pressure ulcers. As detailed below, low air loss technology can be used in conjunction with alternating pressure cells for a customized approach to care. With low air loss beds/mattresses use blower-based pumps designed to manage heat and moisture keeping the skin cool and dry. The low air loss mattress is balanced in zones making it more comfortable for the patient. The torso area supports 100% of the weight setting allowing the feet and shoulder areas to be slightly softer for a more balanced sleep surface. In some cases, on demand low air loss, pulsation and alternating pressure for additional therapy and comfort can be incorporated.

FIG. 5B shows an actuated pin grid array of actuators which consists of a glass tube with graphite pistons inside. Built-in sensors can be provided. The capacitively coupled resistance transducer overcomes the major position sensing difficulties impeding the development of an expansive prototype of digital clay with extent and resolution of the order that is needed. The dependence on solenoid actuated valves was still an obstacle to compactness that will be discussed next. Actuation strategies discussed to this point have required two valves per actuator; hence an n×n array would require 2n^2 valves. Solenoid valves are controlled by computers to the control action. One set of valves controls the opening of a "control coupler" which is actually a second stage of the fluid valve. Opening a row control solenoid valve connects one entire row of actuators to the column control valves which can then move each actuator in that column.

The array of sensors 806 can be resistive, capacitive, or inductive sensors similar to those used in touch-screen sensors. The array of sensors 806 can be printed on a flexible substrate. Capacitive type sensors printed on a flexible substrate have advantages of a relatively long lifespan and ease of implementation of various data input touches and gestures, and thus capacitive type touchscreens have been increasingly employed. Implementation of a multi-touch interface is especially easy in capacitive type touchscreens, as compared to resistive type touchscreens. Capacitive type touchscreens include a plurality of electrodes having a predetermined pattern, the electrodes defining a plurality of nodes in which changes in capacitance are generated due to touches. The nodes deployed in a two-dimensional plane generate changes in self-capacitance or mutual capacitance by a touch. Coordinates of the touch may be calculated by applying a weighted average method or the like to the change in the capacitance generated at the nodes.

A leaky wave body position sensor can be used. The system may comprise configuring one or more leaky wave antennas in on a bed mattress utilizing conductive traces in the touchscreen interface for communication of wireless RF signals. A resonant frequency of the one or more leaky wave antennas may be configured utilizing micro-electro-mechanical systems (MEMS) deflection. The one or more leaky wave antennas may be configured to communicate the RF signals in a desired direction. The one or more leaky wave antennas may comprise microstrip waveguides, where a cavity height of the one or more leaky wave antennas is dependent on spacing between conductive lines in the microstrip waveguides. The one or more leaky wave antennas may comprise coplanar waveguides, where a cavity height of the one or more leaky wave antennas is dependent on spacing between conductive lines in the coplanar waveguides. The body position may be sensed utilizing capacitance, inductance, and/or resistance measurements.

A sonar sensor or a suitable wireless radar device 808 can be used to detect patient position. For example, a monitoring system includes a Doppler radar formed with an IEEE 802 protocol transmitter and an IEEE 802 protocol receiver to detect motion, wherein frequency waves are transmitted by the IEEE 802 protocol transmitter and reflected waves are received by the IEEE protocol 802 receiver; and an analyzer to perform Doppler operations using the IEEE 802 protocol transmitter and receiver, wherein the analyzer calibrates a training Doppler radar signal during a training phase to develop a model and wherein the analyzer applies the model with the Doppler radar signal during an operational phase to determine position. More details in the position sensor are detailed in U.S. Pat. No. 9,549,691 to inventor Bao Tran, the content of which is incorporated by reference.

A camera-based patient position detection can be used. Computer vision is used to segment parts of the patient on the bed, and a deep learning neural network can be used to determine whether a patient is laying in a particular position for too long and the processor can control the actuators to shift the patient position to alternate positions to avoid bed sore and other issues. Through various software modules, the system reads video sequence and generates a 3D anatomy file out of the sequence. The proper bone and muscle scene structure are created for head and face. A based profile stock phase shape will be created by this scene structure. Every scene will then be normalized to a standardized viewport.

Two or more cameras, camera parameters (e.g. field of view) can be preset to fixed numbers. Each pixel from each camera maps to a cone space. The system identifies one or more 3D feature points (such as a birthmark or an identifiable body landmark) on the patient. The 3D feature point can be detected by identifying the same point from two or more different angles. By determining the intersection for the two or more cones, the system determines the position of the feature point. The above process can be extended to certain feature curves and surfaces, e.g. straight lines, arcs, flat surfaces, cylindrical surfaces. Thus, the system can detect curves if a feature curve is known as a straight line or arc. Additionally, the system can detect surfaces if a feature surface is known as a flat or cylindrical surface. The further the patient is from the camera, the lower the accuracy of the feature point determination. Also, the presence of more cameras would lead to more correlation data for increased accuracy in feature point determination. When correlated feature points, curves and surfaces are detected, the remaining surfaces are detected by texture matching and shading changes. Predetermined constraints are applied based on silhouette curves from different views. A different constraint can be applied when one part of the patient is occluded by another object. Further, as the system knows what basic organic shape it is detecting, the basic profile can be applied and adjusted in the process.

In a single camera example, the 3D feature point (e.g. a birth mark) can be detected if the system can identify the same point from two frames. The relative motion from the two frames should be small but detectable. Other features curves and surfaces will be detected correspondingly but can be tessellated or sampled to generate more feature points. A transformation matrix is calculated between a set of feature points from the first frame to a set of feature points from the second frame. When correlated feature points, curves and surfaces are detected, the rest of the surfaces will be detected by texture matching and shading changes.

A convolutional neural network (CNN) can be used to analyze patient on bed imagery for image classification. Image classification is the process of taking an input (like a picture) and outputting a class (like "patient laying prone on side A") or a probability that the input is a particular class. The CNN has Convolutional layers, ReLU layers, Pooling layers, and a Fully connected layer. The flow of the camera-based patient bed-sore handling system is as follows: Input-→Convolution→ReLU→Convolution→ReLU→Pooling→ReLU→Convolution→ReLU→Pooling→Fully Connected. The CNN convolves learned features with input data and uses 2D convolutional layers. This means that this type of network is ideal for processing 2D images.

In addition to positioning, pressure sensing can be done using the camera by examining changes in the images of the bed and by analyzing the gradual depth changes from the flat mattress to the depression in the mattress caused by patient weight. The CNN can be trained using images of different patients with different weight to detect the pressure placed on the bed/mattress. For high precision, pressure sensors may be resistive pressure sensors, but are not limited to resistive pressure sensors and can be a variety of other types of pressure sensors as well as other physiological and biomechanical sensors. In either case, the processor receives raw data from pressure sensors and generates pressure data for transmission to a local base station. The processor is part of a medical node which can process the raw data from pressure sensors to generate the pressure data. The transmitter is used to transmit the pressure data to the base station such as a Bluetooth PC or mobile phone, for example. In operation, pressure sensors sense pressure from a patient placed on them. The pressure sensor can be piezoelectric sensors, capacitive sensors, or resistive sensors. For example, where pressure sensors are resistive sensors, the resistance in primary pressure sensors varies as different pressure and/or force is applied to them. Medical node sends current through pressure sensors and determines the pressure at each pressure sensor from the resistance detected. Based on the pressure, the shoe can be customized to compensate for any unsuitable pressure experienced by the bed-ridden patient and optimize the bed rest experience.

A pressure-detection mat includes at least one layer of an insulating material sandwiched between a first layer of conducting strips and a second layer of conducting strips, the conducting strips of the first electrode layer and the conducting strips of the second layer overlapping at a plurality of intersections; a first bundle of connecting wires for connecting the conducting strips of the first layer to a control unit; a second bundle of connecting wires for connecting the conducting strips of the second layer to the control unit. The pressure-detection mat may have at least one discontinuity such that at least one conducting strip of the first layer is non-continuous and includes at least a first segment and a second segment; and the first segment is connected to the second segment by a bridging wire to provide conductive communication therebetween. The conducting strip of the first segment comprises a composite of a conductive material and a conductive wire. The conducting strip of the pressure-detection mat may comprise an array of strip electrodes embedded in the insulating material, each of the strip electrode comprising a plurality of segments of conductive material; a connecting wire in conductive contact with said segments, said connecting wire having a length exceeding the length of the strip electrode such that said connecting wire adopts a sinuous configuration along the strip electrode; and a flexible laminate into which said segments and said connecting wire are embedded; and the first layer and the second layer are orientated such that the strip electrodes of the first layer and the strip electrodes of the second electrode layer overlap at a plurality of intersections. The capacitance sensor will retain its functionality even if it is fully pressed continuously for long periods such as or even longer than 30 days and keep its characteristics for periods over the lifetime of the sensing mat which is typically more than a year. Notably, the sensor characteristics should preferably be consistent between two separate events. The mat may further include additional sensors configured to monitor additional factors, particularly additional factors influencing the development of bedsores, such as temperature, humidity, moisture, or the like. Such additional sensors may be configured to monitor the factors continuously or intermittently as appropriate to detect high risk combinations of factors. Such measurements may be recorded and stored in a database for further analysis.

Optionally, additional sensors may be located apart from the pressure-detection mat. For example, the mat could be integrated into a seat of a chair and a touch sensor could be integrated into a chair's back support for placing patients in a sitting or prone position. Where required, additional sensors may be formed from selectively conducting material. Selectively conductive materials, such as described herein, may be particularly advantageous to such pressure-detection mats because they are flexible. The isolating and insulating layer 570 material may be a compressible, typically sponge-like, airy or proliferous material (e.g. foam), allowing for a significant change in density when pressure is applied to it. Materials comprising the sensing mat are typically durable enough to be resistant to normal wear-and-tear of daily use. Furthermore, the sensing mat may be configured so as not to create false pressure readings, for example when the mat is folded. Accordingly, the pressure-detection mat or sensing-mat, may be placed underneath or otherwise integrated with other material layers such as used in standard bed sheets. It will be appreciated that such additional materials may confer further properties as may be required for a particular application. Where required, the conductive material of the selectively conducting fabric may be further covered with an isolating, washable, water resistant, breathing cover mat, allowing minimum discomfort to the subject resting on the mat.

In addition to pressure sensing, other personal data can be captured. For example, the sensors can include bio-impedance sensors that use bioelectrical impedance analysis (BIA) to estimate the heart rate by amplifying the pulsatile impedance component superimposed on the basal impedance. BIA can be used to detect the presence of water accumulation in the patient. The heart rate (HR) can be detected from bioimpedance measured in a single foot. Four electrodes are used for measurement of bioimpedance signal; two electrodes for injecting current and the other two to capture the voltage signal from human body. The bio-impedance signal shows deflections corresponding to systole and diastole activity as a measure of heart rate. The electrodes embedded in the footwear 4 apply a 50 kHz voltage between the outer electrode pairs and measure the drop-in voltage across the inner electrode pairs. An impedance converter separates impedance into real and imaginary part using discrete Fourier transform. The real and imaginary values of the measured bio-impedance signal are processed by a processor to obtain a continuous signal. The bioimpedance signal obtained after de-noising using adaptive thresholding. For heart rate detection, synchronous demodulator plays vital role by demodulating the bio-impedance signal from current carrier. To achieving high CMRR in signal in analog differential synchronous demodulator for AC signals, the signal is synchronously demodulated using the floating capacitor with high CMRR. An impedance analyzer is used for getting bio-impedance signal. Wavelet thresholding methods can be used for noise removal where wavelet coefficients are threshold in order to remove their noisy part.

In addition to position sensors, other sensors can be provided to protect the patient against issues from intubation. As detailed in U.S. Pat. No. 7,502,498 to Bao Tran, a monitoring system includes one or more cameras to determine a three-dimensional (3D) model of a person; means to detect a dangerous condition based on the 3D model; and means to generate a warning when a dangerous intubation condition is detected. The patient may wear one or more sensors, for example devices for sensing ECG, EKG, blood pressure, sugar level, among others. The sensors are mounted on the patient's wrist (such as a wristwatch sensor) and other convenient anatomical locations. Exemplary sensors 40 include standard medical diagnostics for detecting the body's electrical signals emanating from muscles (EMG and EOG) and brain (EEG) and cardiovascular system (ECG). Leg sensors can include piezoelectric accelerometers designed to give qualitative assessment of limb movement. Additionally, thoracic and abdominal bands used to measure expansion and contraction of the thorax and abdomen respectively. A small sensor can be mounted on the subject's finger in order to detect blood-oxygen levels and pulse rate. Additionally, a microphone can be attached to throat and used in sleep diagnostic recordings for detecting breathing and other noise. One or more position sensors can be used for detecting orientation of body (laying on left side, right side or back) during sleep diagnostic recordings. Each of sensors can individually transmit data to the server using wired or wireless transmission. Alternatively, all sensors can be fed through a common bus into a single transceiver for wired or wireless transmission. The transmission can be done using a magnetic medium such as a floppy disk or a flash memory card or can be done using infrared or radio network link, among others. The sensor can also include a local position system receiver that relays the position and ambulatory patterns of the patient to the server for mobility tracking. The sensors for monitoring vital signs are enclosed in a wrist-watch sized case supported on a wrist band. The sensors can be attached to the back of the case. For example, a Cygnus' AutoSensor (Redwood City, Calif) is used as a glucose sensor. A low electric current pulls glucose through the skin. Glucose is accumulated in two gel collection discs in the AutoSensor. The AutoSensor measures the glucose and a reading is displayed by the watch. Alternatively, EKG/ECG contact points are positioned on the back of the wrist-watch case. A pressure sensor Continuous, providing beat-to-beat wrist arterial pulse rate measurements, can be housed in a casing with a 'free-floating' plunger as the sensor applanates the radial artery. A strap provides a constant force for effective applanation and ensuring the position of the sensor housing to remain constant after any wrist movements. The change in the electrical signals due to change in pressure is detected as a result of the piezoresistive nature of the sensor are then analyzed to arrive at various arterial pressure, systolic pressure, diastolic pressure, time indices, and other blood pressure parameters.

The case may be of a number of variations of shape but can be conveniently made a rectangular, approaching a box-like configuration. The wristband can be an expansion band or a wristwatch strap of plastic, leather or woven material. The wristband further contains an antenna for transmitting or receiving radio frequency signals. The wristband and the antenna inside the band are mechanically coupled to the top and bottom sides of the wrist-watch housing. Further, the antenna is electrically coupled to a radio frequency transmitter and receiver for wireless communications with another computer or another user. Although a wristband is disclosed, a number of substitutes may be used, including a belt, a ring holder, a brace, or a bracelet, among other suitable substitutes known to one skilled in the art. The housing contains the processor and associated peripherals to provide the human-machine interface. A display is located on the front section of the housing. A speaker, a microphone, and a plurality of push-button switches and are also located on the front section of housing. An infrared LED transmitter and an infrared LED receiver are positioned on the right side of housing to enable the watch to communicate with another computer using infrared transmission.

The sensors are mounted on the patient's clothing. For example, sensors can be woven into a single-piece garment (an undershirt) on a weaving machine. A plastic optical fiber can be integrated into the structure during the fabric production process without any discontinuities at the armhole or the seams. An interconnection technology transmits information from (and to) sensors mounted at any location on the body thus creating a flexible "bus" structure. T-Connectors—similar to "button clips" used in clothing—are attached to the fibers that serve as a data bus to carry the information from the sensors (e.g., EKG sensors) on the body. The sensors will plug into these connectors and at the other end similar T-Connectors will be used to transmit the information to monitoring equipment or personal status monitor. Since shapes and sizes of humans will be different, sensors can be positioned on the right locations for all patients and without any constraints being imposed by the clothing. Moreover, the clothing can be laundered without any damage to the sensors themselves. In addition to the fiber optic and specialty fibers that serve as sensors and data bus to carry sensory information from the wearer to the monitoring devices, sensors for monitoring the respiration rate can be integrated into the structure.

Instead of being mounted on the patient, the sensors can be mounted on fixed surfaces such as walls or tables, for example. One such sensor is a motion detector. Another sensor is a proximity sensor. The fixed sensors can operate alone or in conjunction with the cameras 10. Where the motion detector operates with the cameras 10, the motion detector can be used to trigger camera recording. Thus, as long as motion is sensed, images from the cameras 10 are not saved. However, when motion is not detected, the images are stored, and an alarm may be generated. Where the motion detector operates stand alone, when no motion is sensed, the system generates an alarm.

The server also executes one or more software modules to analyze data from the patient. A module monitors the patient's vital signs such as ECG/EKG and generates warnings should problems occur. In this module, vital signs can be collected and communicated to the server 20 using wired or wireless transmitters. The server 20 feeds the data to a statistical analyzer such as a neural network which has been trained to flag potentially dangerous conditions. The neural network can be a back-propagation neural network, for example. The statistical analyzer is trained with training data where certain signals are determined to be undesirable for the patient, given his age, weight, and physical limitations, among others. For example, the patient's glucose level should be within a well-established range, and any value outside of this range is flagged by the statistical analyzer as a dangerous condition. As used herein, the dangerous condition can be specified as an event or a pattern that can cause physiological or psychological damage to the patient. Moreover, interactions between different vital signals can be accounted for so that the statistical analyzer can take into consideration instances where individually the vital signs are acceptable, but in certain combinations, the vital signs can indicate potentially dangerous conditions. Once trained, the data received by the server 20 can be appropriately scaled and processed by the statistical analyzer. In addition to statistical analyzers, the server 20 can process vital signs using rule-based inference engines, fuzzy logic, as well as conventional if-then logic. Additionally, the server can process vital signs using Hidden Markov Models (HMMs), dynamic time warping, or template matching, among others.

The patient position can be adjusted using an array of actuators as shown in FIGS. 5B and 5C or can be actuated using air or liquid interdigitated fingers shown in FIG. 5A. For example, low air loss beds can use inflatable cushions or air bags as the supporting surface for a patient. By using a fluid supporting medium such as air or water within the bags, an irregularly shaped body placed on top of the air bags will deform the supporting surface in such a manner so as to provide a more uniform distribution of load bearing pressure points than can be attained with a conventional mattress. When a patient lies supinely on a flat surface, or even on a conventional mattress, most of the load is borne by protuberances of the posterior surface of the body such as the heels, the buttocks, the scapula, and the occipital region of the head. The relatively small areas of soft tissue at these points are then subjected to high pressures by being compressed between the skeleton and the supporting surface. When this pressure becomes great enough to cause collapse of small capillaries and veins, pressure sores may result. By uniformly distributing the supporting pressure points along the body surface, the pressure at these critical areas can be reduced. Patients are also predisposed to pressure sores by the accumulation of moisture at the skin surface. For this reason, air bags which are permeable to water vapor are preferred. A continuous flow of air through the bags from a source of pressurized air is then necessary to remove the water vapor, the air being exhausted through separate outlets or pores in the fabric of the bags. An air supply for inflating the cells to the required pressure and outlets or exhaust ports in the cells to allow the escape of air. The bed is divided into sections, each of which comprises a group of air bags. Each section is provided with a pressure sensor and a control valve allowing each section of the bed to be inflated to different pressures. Alternatively, the air pressure in each section is controlled by valves in the outlets from the section.

The bed includes actuators for adjusting the patient's attitude on the bed. For instance, the head of the bed can be raised to sit the patient up or the angle of the entire frame of the bed can be changed with respect to the horizontal when, for therapeutic reasons, the patient is placed in the Trendelenburg or reverse Trendelenburg positions. Those changes require re-adjustment of the air supply in each section of air bags. Movement of the patient may also necessitate adjustment of the pressure in each section as the patient's weight distribution on the bed changes.

An alternating pressure mattress can be used with a plurality of alternately inflatable, interdigitated cells or tubes either connected to form a mattress or formed from closely approximated sheets of air impermeable material which have been heat sealed or otherwise bonded at the edges and with tubes or channels formed therein to form alternating cells. A controllable air supply is provided to each set of cells. By alternately inflating and deflating each set of cells in opposite phase to the other set, the supporting surface of the mattress is alternated between each set of cells to periodically relieve and transfer points of contact between the patient's body and the supporting surface.

The degree of uniformity of support provided by a low air loss bed varies with the pressure existing within the air bags for any given patient. The pressure exerted against a body resting on an air bag is approximately equal to the air pressure within the bag when the air bag is deformed only to an extent which flattens the body contacting surface of the bag. Further deformation increases the pressure exerted by the bag surface against the body because the body contacting surface of the bag, in addition to being pushed by the air pressure within the bag, is pulled by the tension existing in the bag fabric surrounding the body. This tension is maintained by the air pressure exerted against the inner surfaces of the bag which surround the body. In any case, of course, the pressure exerted against the body by the bag surface integrated over the total body contacting surface equals the weight of the body.

Based on sensor readings, the processor controls the actuator 804 to maintain the air pressure within the interdigitated air bags at a value low enough to allow the supporting surface to be deformed in order to increase the weight bearing surface area but not low enough that too much tension is produced in the bag fabric surrounding the body contacting surface. Such tension in the fabric interferes with the deformation of the supporting surface by protruding body parts. Therefore, for a body of any particular size and weight, the processor controls the actuators to maintain a pressure value which maximizes the degree of uniformity of support provided to the body by the air bag. Since weight is not distributed evenly on the human frame, this ideal pressure value varies with different body regions. Heavier regions such as the buttocks require greater pressure to achieve uniform support while lighter regions such as the feet require less pressure.

The above low air loss bed incorporates some of the characteristics of an alternating pressure mattress enables the periodic relieving alternate body areas of pressure would ensure that no body area becomes completely ischemic due to excessive support pressure. Also, if the bags are positioned transversely, periodically increasing the pressure to alternate body areas has the effect of compressing subcutaneous veins which, owing to the one-way valves existing in human veins, provides an impetus to the flow of blood back to the heart. This improve arterial circulation, but it also makes less likely venous pooling which can cause edema and predispose the patient to pressure sores.

The processor maintains an ideal pressure in each bag within limits. Furthermore, this ideal pressure varies with the particular body region being supported by a group of air bags. The processor can also allow operator selection of the air bag pressure for each set of air bags supporting a particular body region and maintains that ideal pressure as a setpoint or baseline value about which the pressures are raised and lowered as the pressure points are alternately shifted from one set of interdigitated bags to another.

The system applies sensors to protect the patient in a prone/face down position where the Endotracheal tube (ETT) can be pulled out or it and get blocked. ETT obstruction, either complete or partial, is a serious life-threatening complication in intubated patients. One system applies the sonar system invented by Bao Tran and previously incorporated-by-reference to detect ETT obstruction. In that system the sonar system detects sound reflection and applies a deep learning neural network to detect ETT obstruction. BIA can be used to detect ETT obstruction, as aided by the CNN. Alteration in respiratory sound signals caused by ETT occlusion can be used for early detection of obstruction. A microphone can be used to record respiratory sounds during both spontaneous breathing and mechanical ventilation and the result can be analyzed by the CNN. Data analysis revealed that sound intensity level decreased significantly when the degree of obstruction increased. In addition, this change in sound level was not related to the location of obstruction.

An acoustic sensor (microphone or piezoelectric sensor) and an electrical sensor such as EKG sensor contact the patient with a conductive gel material. The conductive gel material provides transmission characteristics so as to provide an effective acoustic impedance match to the skin in addition to providing electrical conductivity for the electrical sensor. The acoustic transducer can be directed mounted on the conductive gel material substantially with or without an intermediate air buffer. The entire patch is then packaged as sterile as are other over-the-counter adhesive bandages. When the patch is worn out, the module may be removed, and a new patch backing may be used in place of the old patch. One or more patches may be applied to the patient's body and these patches may communicate wirelessly using the mesh network or alternatively they may communicate through a personal area network using the patient's body as a communication medium. The acoustic sensor can pick up lung sounds, and heart sounds and such information can be correlated with the EKG sensor output. More details are disclosed in U.S. Pat. No. 7,539,532 to Bao Tran, the content of which is incorporated by reference herewith. The system can analyze blood pressure, and heart rate, and pulse oximetry values to characterize the user's cardiac condition. These programs, for example, may provide a report that features statistical analysis of these data to determine averages, data displayed in a graphical format, trends, and comparisons to doctor-recommended values.

Lung sounds, also called breath sounds, can be auscultated across the anterior and posterior chest walls with a stethoscope. Adventitious lung sounds are referenced as crackles (rales), wheezes (rhonchi), stridor and pleural rubs as well as voiced sounds that include egophony, bronchophony and whispered pectoriloquy. The neural network is trained on a database of lung sounds that include the following exemplary conditions.
  1. Vesicular—Diminished
  2. Bronchophony—Healthy
  3. Bronchophony—Abnormal
  4. Egophony—e
  5. Egophony—a
  6. Whispered Pectoriloquy—Healthy
  7. Whispered Pectoriloquy—Abnormal
  8. Wheeze—Expiratory
  9. Wheeze—Monophonic
  10. Wheeze—Polyphonic
  11. Crackles—Early Inspiratory (Rales)
  12. Crackles—Late Inspiratory (Rales)
  13. Stridor Successful placement is checked first by listening to the lungs with a stethoscope and often verified with a chest x-ray. In the field or the operating room, a device that measures carbon dioxide—which would only be present if the tube was in the lungs, rather than in the esophagus—is used to confirm that it was placed correctly. Then the neural network is applied to detect ETT issues. The system reduces risks arising from issues that can arise particularly when a patient must remain on the ventilator for an extended period of time. Common risks analyzed by the neural network and the hospital staff may include: trauma to the teeth, mouth, tongue, and/or larynx, accidental intubation in the esophagus (food tube) instead of the trachea (air tube), trauma to the trachea, bleeding, inability to be weaned from the ventilator, requiring tracheostomy, aspirating (inhaling) vomit, saliva or other fluids while intubated, pneumonia, if aspiration occurs, sore throat, hoarseness, erosion of soft tissue (with prolonged intubation).

A neural network for speech recognition can be used with updated parameters to recognize the lung conditions, for example as taught in U.S. Pat. No. 6,070,140 to Bao Tran, the content of which is incorporated by reference. Feed forward artificial neural networks (NNs) are used to classify valve-related heart disorders. The heart sounds are captured using the microphone or piezoelectric transducer. Relevant features were extracted using several signal processing tools, discrete wavelet transfer, Fast Fourier Transform, and linear prediction coding. The heartbeat sounds are processed to extract the necessary features by: a) denoising using wavelet analysis, b) separating one beat out of each record c) identifying each of the first heart sound (FHS) and the second heart sound (SHS). Valve problems are classified according to the time separation between the FHS and the SHS relative to cardiac cycle time, namely whether it is greater or smaller than 20% of cardiac cycle time. The NN can comprise 6 nodes at both ends, with one hidden layer containing 10 nodes. The linear predictive code (LPC) coefficients for each event were fed to two separate neural networks containing hidden neurons.

A normalized energy spectrum of the sound data is obtained by applying a Fast Fourier Transform. The various spectral resolutions and frequency ranges were used as inputs into the NN to optimize these parameters to obtain the most favorable results.

The heart sounds are denoised using six-stage wavelet decomposition, thresholding, and then reconstruction. Three feature extraction techniques were used: the Decimation method, and the wavelet method. Classification of the heart diseases is done using Hidden Markov Models (HMMs).

A wavelet transform is applied to a window of two periods of heart sounds. Two analyses are realized for the signals in the window: segmentation of first and second heart sounds, and the extraction of the features. After segmentation, feature vectors are formed by using he wavelet detail coefficients at the sixth decomposition level. The best feature elements are analyzed by using dynamic programming.

The wavelet decomposition and reconstruction method extract features from the heart sound recordings. An artificial neural network classification method classifies the heart sound signals into physiological and pathological murmurs. The heart sounds are segmented into four parts: the first heart sound, the systolic period, the second heart sound, and the diastolic period. The following features can be extracted and used in the classification algorithm: a) Peak intensity, peak timing, and the duration of the first heart sound b) the duration of the second heart sound c) peak intensity of the aortic component of S2(A2) and the pulmonic component of S2 (P2), the splitting interval and the reverse flag of A2 and P2, and the timing of A2 d) the duration, the three largest frequency components of the systolic signal and the shape of the envelope of systolic murmur e) the duration the three largest frequency components of the diastolic signal and the shape of the envelope of the diastolic murmur.

The time intervals between the ECG R-waves are detected using an envelope detection process. The intervals between R and T waves are also determined. The Fourier transform is applied to the sound to detect S1 and S2. To expedite processing, the system applies Fourier transform to detect S1 in the interval 0.1-0.5 R-R. The system looks for S2 the intervals R-T and 0.6 R-R. S2 has an aortic component A2 and a pulmonary component P2. The interval between these two components and its changes with respiration has clinical significance. A2 sound occurs before P2, and the intensity of each component depends on the closing pressure and hence A2 is louder than P2. The third heard sound S3 results from the sudden halt in the movement of the ventricle in response to filling in early diastole after the AV valves and is normally observed in children and young adults. The fourth heart sound S4 is caused by the sudden halt of the ventricle in response to filling in presystole due to atrial contraction.

The S2 is identified and a normalized splitting interval between A2 and P2 is determined. If there is no overlap, A2 and P2 are determined from the heart sound. When overlap exists between A2 and P2, the sound is dechirped for identification and extraction of A2 and P2 from S2. The A2-P2 splitting interval (SI) is calculated by computing the cross-correlation function between A2 and P2 and measuring the time of occurrence of its maximum amplitude. SI is then normalized (NSI) for heart rate as follows: NSI=SI/cardiac cycle time. The duration of the cardiac cycle can be the average interval of QRS waves of the ECG. It could also be estimated by computing the mean interval between a series of consecutive S1 and S2 from the heart sound data. A nonlinear regressive analysis maps the relationship between the normalized NSI and PAP. A mapping process such as a curve-fitting procedure determines the curve that provides the best fit with the patient data. Once the mathematical relationship is determined, NSI can be used to provide an accurate quantitative estimate of the systolic and mean PAP relatively independent of heart rate and systemic arterial pressure.

The first heart sound (S1) is detected using a time-delayed neural network (TDNN). The network consists of a single hidden layer, with time-delayed links connecting the hidden units to the time-frequency energy coefficients of a Morlet wavelet decomposition of the input phonocardiogram (PCG) signal. The neural network operates on a 200 msec sliding window with each time-delay hidden unit spanning 100 msec of wavelet data.

A local signal analysis is used with a classifier to detect, characterize, and interpret sounds corresponding to symptoms important for cardiac diagnosis. The system detects a plurality of different heart conditions. Heart sounds are automatically segmented into a segment of a single heartbeat cycle. Each segment is then transformed using 7 level wavelet decomposition, based on Coifman 4th order wavelet kernel. The resulting vectors 4096 values are reduced to 256 element feature vectors, this simplified the neural network and reduced noise.

Feature vectors are formed by using the wavelet detail and approximation coefficients at the second and sixth decomposition levels. The classification (decision making) is performed in 4 steps: segmentation of the first and second heart sounds, normalization process, feature extraction, and classification by the artificial neural network.

Using decision trees, the system distinguishes (1) the Aortic Stenosis (AS) from the Mitral Regurgitation (MR) and (2) the Opening Snap (OS), the Second Heart Sound Split (A2_P2) and the Third Heart Sound (S3). The heart sound signals are processed to detect the first and second heart sounds in the following steps: a) wavelet decomposition, b) calculation of normalized average Shannon Energy, c) a morphological transform action that amplifies the sharp peaks and attenuates the broad ones d) a method that selects and recovers the peaks corresponding to S1 and S2 and rejects others e) algorithm that determines the boundaries of S1 and S2 in each heart cycle f) a method that distinguishes S1 from S2.

Once the heart sound signal has been digitized and captured into the memory, the digitized heart sound signal is parameterized into acoustic features by a feature extractor. The output of the feature extractor is delivered to a sound recognizer. The feature extractor can include the short time energy, the zero crossing rates, the level crossing rates, the filter-bank spectrum, the linear predictive coding (LPC), and the fractal method of analysis. In addition, vector quantization may be utilized in combination with any representation techniques. Further, one skilled in the art may use an auditory signal-processing model in place of the spectral models to enhance the system's robustness to noise and reverberation The digitized heart sound signal series s(n) is put through a low-order filter, typically a first-order finite impulse response filter, to spectrally flatten the signal and to make the signal less susceptible to finite precision effects encountered later in the signal processing. The signal is pre-emphasized preferably using a fixed pre-emphasis network, or pre-emphasizer. The signal can also be passed through a slowly adaptive pre-emphasizer. The pre-emphasized heart sound signal is next presented to a frame blocker to be blocked into frames of N samples with adjacent frames being separated by M samples. In one implementation, frame 1 contains the first 400 samples. The frame 2 also contains 400 samples but begins at the 300th sample and continues until the 700th sample. Because the adjacent frames overlap, the resulting LPC spectral analysis will be correlated from frame to frame. Each frame is windowed to minimize signal discontinuities at the beginning and end of each frame. The windower tapers the signal to zero at the beginning and end of each frame. Preferably, the window used for the autocorrelation method of LPC is the Hamming window. A noise canceller operates in conjunction with the autocorrelator to minimize noise. Noise in the heart sound pattern is estimated during quiet periods, and the temporally stationary noise sources are damped by means of spectral subtraction, where the autocorrelation of a clean heart sound signal is obtained by subtracting the autocorrelation of noise from that of corrupted heart sound. In the noise cancellation unit, if the energy of the current frame exceeds a reference threshold level, the heart is generating sound and the autocorrelation of coefficients representing noise is not updated. However, if the energy of the current frame is below the reference threshold level, the effect of noise on the correlation coefficients is subtracted off in the spectral domain. The result is half-wave rectified with proper threshold setting and then converted to the desired autocorrelation coefficients. The output of the autocorrelator and the noise canceller are presented to one or more parameterization units, including an LPC parameter unit, an FFT parameter unit, an auditory model parameter unit, a fractal parameter unit, or a wavelet parameter unit, among others. The LPC parameter is then converted into cepstral coefficients. The cepstral coefficients are the coefficients of the Fourier transform representation of the log magnitude spectrum. A filter bank spectral analysis, which uses the short-time Fourier transformation (STFT) may also be used alone or in conjunction with other parameter blocks. FFT is well known in the art of digital signal processing. Such a transform converts a time domain signal, measured as amplitude over time, into a frequency domain spectrum, which expresses the frequency content of the time domain signal as a number of different frequency bands. The FFT thus produces a vector of values corresponding to the energy amplitude in each of the frequency bands. The FFT converts the energy amplitude values into a logarithmic value which reduces subsequent computation since the logarithmic values are more simple to perform calculations on than the longer linear energy amplitude values produced by the FFT, while representing the same dynamic range. Ways for improving logarithmic conversions are well known in the art, one of the simplest being use of a look-up table. In addition, the FFT modifies its output to simplify computations based on the amplitude of a given frame. This modification is made by deriving an average value of the logarithms of the amplitudes for all bands. This average value is then subtracted from each of a predetermined group of logarithms, representative of a predetermined group of frequencies. The predetermined group consists of the logarithmic values, representing each of the frequency bands. Thus, utterances are converted from acoustic data to a sequence of vectors of k dimensions, each sequence of vectors identified as an acoustic frame, each frame represents a portion of the utterance. Alternatively, auditory modeling parameter unit can be used alone or in conjunction with others to improve the parameterization of heart sound signals in noisy and reverberant environments. In this approach, the filtering section may be represented by a plurality of filters equally spaced on a log-frequency scale from 0 Hz to about 3000 Hz and having a prescribed response corresponding to the cochlea. The nerve fiber firing mechanism is simulated by a multilevel crossing detector at the output of each cochlear filter. The ensemble of the multilevel crossing intervals corresponding to the firing activity at the auditory nerve fiber-array. The interval between each successive pair of same direction, either positive or negative going, crossings of each predetermined sound intensity level is determined and a count of the inverse of these interspike intervals of the multilevel detectors for each spectral portion is stored as a function of frequency. The resulting histogram of the ensemble of inverse interspike intervals forms a spectral pattern that is representative of the spectral distribution of the auditory neural response to the input sound and is relatively insensitive to noise The use of a plurality of logarithmically related sound intensity levels accounts for the intensity of the input signal in a particular frequency range. Thus, a signal of a particular frequency having high intensity peaks results in a much larger count for that frequency than a low intensity signal of the same frequency. The multiple level histograms of the type described herein readily indicate the intensity levels of the nerve firing spectral distribution and cancel noise effects in the individual intensity level histograms. Alternatively, the fractal parameter block can further be used alone or in conjunction with others to represent spectral information. Fractals have the property of self-similarity as the spatial scale is changed over many orders of magnitude. A fractal function includes both the basic form inherent in a shape and the statistical or random properties of the replacement of that shape in space. As is known in the art, a fractal generator employs mathematical operations known as local affine transformations. These transformations are employed in the process of encoding digital data representing spectral data. The encoded output constitutes a "fractal transform" of the spectral data and consists of coefficients of the affine transformations. Different fractal transforms correspond to different images or sounds.

Alternatively, a wavelet parameterization block can be used alone or in conjunction with others to generate the parameters. Like the FFT, the discrete wavelet transform (DWT) can be viewed as a rotation in function space, from the input space, or time domain, to a different domain. The DWT consists of applying a wavelet coefficient matrix hierarchically, first to the full data vector of length N, then to a smooth vector of length N/2, then to the smooth-smooth vector of length N/4, and so on. Most of the usefulness of wavelets rests on the fact that wavelet transforms can usefully be severely truncated or turned into sparse expansions. In the DWT parameterization block, the wavelet transform of the heart sound signal is performed. The wavelet coefficients are allocated in a non-uniform, optimized manner. In general, large wavelet coefficients are quantized accurately, while small coefficients are quantized coarsely or even truncated completely to achieve the parameterization. Due to the sensitivity of the low-order cepstral coefficients to the overall spectral slope and the sensitivity of the high-order cepstral coefficients to noise variations, the parameters generated may be weighted by a parameter weighing block, which is a tapered window, so as to minimize these sensitivities. Next, a temporal derivator measures the dynamic changes in the spectra. Power features are also generated to enable the system to distinguish heart sound from silence.

After the feature extraction has been performed, the heart sound parameters are next assembled into a multidimensional vector and a large collection of such feature signal vectors can be used to generate a much smaller set of vector quantized (VQ) feature signals by a vector quantizer that cover the range of the larger collection. In addition to reducing the storage space, the VQ representation simplifies the computation for determining the similarity of spectral analysis vectors and reduces the similarity computation to a look-up table of similarities between pairs of codebook vectors. To reduce the quantization error and to increase the dynamic range and the precision of the vector quantizer, the feature parameters can be partitioned into separate codebooks, preferably three. The first, second and third codebooks correspond to the cepstral coefficients, the differenced cepstral coefficients, and the differenced power coefficients.

With conventional vector quantization, an input vector is represented by the codeword closest to the input vector in terms of distortion. In conventional set theory, an object either belongs to or does not belong to a set. This is in contrast to fuzzy sets where the membership of an object to a set is not so clearly defined so that the object can be a part member of a set. Data are assigned to fuzzy sets based upon the degree of membership therein, which ranges from 0 (no membership) to 1.0 (full membership). A fuzzy set theory uses membership functions to determine the fuzzy set or sets to which a particular data value belongs and its degree of membership therein.

To handle the variance of heart sound patterns of individuals over time and to perform speaker adaptation in an automatic, self-organizing manner, an adaptive clustering technique called hierarchical spectral clustering is used. Such speaker changes can result from temporary or permanent changes in vocal tract characteristics or from environmental effects. Thus, the codebook performance is improved by collecting heart sound patterns over a long period of time to account for natural variations in speaker behavior. Data from the vector quantizer is presented to one or more recognition models, including an HMM model, a dynamic time warping model, a neural network, a fuzzy logic, or a template matcher, among others. These models may be used singly or in combination.

In dynamic processing, at the time of recognition, dynamic programming slides, or expands and contracts, an operating region, or window, relative to the frames of heart sound so as to align those frames with the node models of each S1-S4 pattern to find a relatively optimal time alignment between those frames and those nodes. The dynamic processing in effect calculates the probability that a given sequence of frames matches a given word model as a function of how well each such frame matches the node model with which it has been time-aligned. The word model which has the highest probability score is selected as corresponding to the heart sound.

Figure 6:
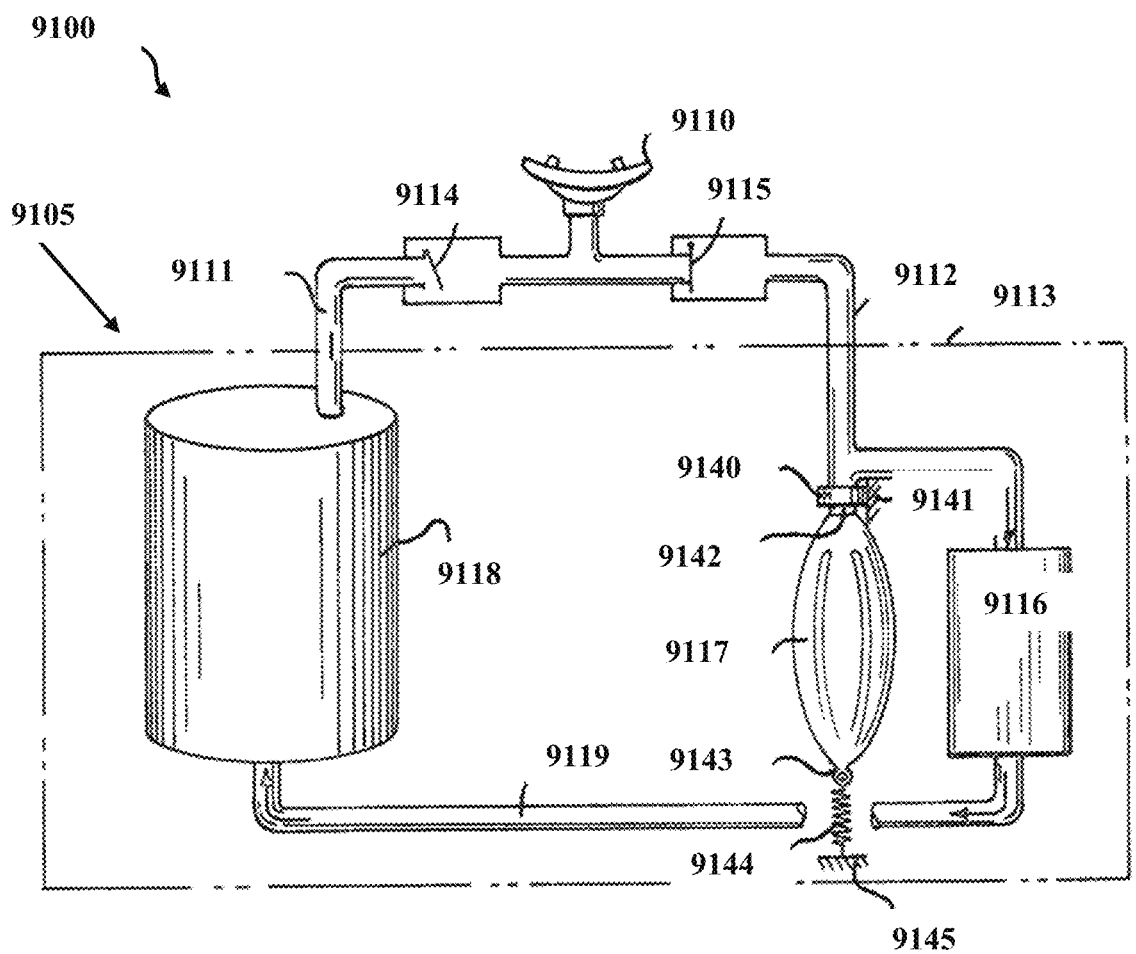
FIG. 6 is a schematic representation showing a mouthpiece for use in a breathing device of a portable respiratory assistance device in one embodiment of the invention.

As illustrated in FIG. 6, a portable breathing assistance device 9100 can include a breathing device 9105 having a mouthpiece 9110 which communicates with inhalation conduit 9111 and an exhalation conduit 9112 which lead to apparatus contained in an enclosure 9113. A check valve 9114 is provided in the inhalation conduit 9111 and a check valve 9115 in the exhalation conduit 9112. The check valves and the mouthpiece often comprise a single piece of equipment, e.g., an integral component. The conduits 9111 and 9112 are flexible conduits. A face mask is sometimes used in place of or in addition to the mouthpiece 9110, both being referred to generically as a "mouth connection." The exhalation conduit 9112 leads to a chemical canister 9116 which contains materials which remove the carbon dioxide and add chemically generated oxygen to the breathing gas. A positive pressure reservoir 9117 communicates with the exhalation conduit 9112 and is in the form of an elongate flexible wall bag of a capacity to accommodate at least a full breath. Such bag is known as a "breathing bag" and is made of rubber. The neck of the bag 9117 is held in a collar 9140 attached to a portion 9141 of the frame (not shown) of the apparatus. There is a loop 9143 at the bottom of the bag and a tensioned coil spring 9144 extends between the loop 9143 and another part 9145 of the frame. The tension exerted by the spring 9144 urges the walls of the bag 117 toward each other into a position of minimum volume. As air is forced into the bag 9117 by the lungs, the walls of the bag 9117 expand, thus shortening the bag and tensioning the spring. The spring is designed so that the bag 9117 then develops a positive pressure of not more than 2 inches water gauge for expulsion of its contents through the canister 9116. The inhalation conduit 9111 leads from a negative pressure reservoir 9118 to the check valve 9114 and mouthpiece 9110. A suitable conduit 9119 extends from the canister 116 to the negative pressure reservoir and functions as an extension of conduit 9111. In the alternative, conduit 9119 can extend to the inhalation conduit 9111 through a T-connection, with the reservoir 9118 connected as in the case of the reservoir 9117. The canister 9116 is disposed between a source of positive pressure and a source of negative pressure with the result that the gas will continue to flow through the canister throughout the major portion of the complete breathing cycle. Since the two reservoirs are alternately charged, whereas the discharge is substantially continuous, the operation of the two reservoirs are not in exact phase relationship, but neither are they 180° out of phase due to the fact that the flow of a given volume takes a certain amount of time.

Although the invention has been described with reference to the above examples, it will be understood that modifications and variations are encompassed within the spirit and scope of the invention. Accordingly, the invention is limited only by the following claims.

What is claimed is:

1. A respiratory assistance device comprising:
   a) a support base having a top surface;
   b) a support layer coupled to the top surface of the support base, the support layer comprising:
      a first opening sized to accommodate a user's face in a prone position; and
      a second opening sized to accommodate the user's chest and abdomen in the prone position, the second opening having a sealing surface disposed about the perimeter of the second opening configured to contact the user's chest and abdomen and fluidly seal the second opening when the user's chest and abdomen contact the sealing surface in the prone position;
   c) a reversibly inflatable cavity within the support base, wherein the cavity is disposed interior to the support base and sealed by the user's chest and abdomen in the prone position;
   d) a pump in fluid connection with the cavity and operable to control inflation and deflation of the cavity such that the user's chest and abdomen are moved to assist breathing of the user by applying positive and negative pressure to the chest and abdomen during inflation and deflation of the cavity;
   e) a breathing device in connection with the first opening configured to deliver a gaseous fluid to the mouth and/or nose of the user; and
   f) one or more sensors configured to detect a position and/or a physiological parameter of the user.

2. The device of claim 1, wherein the breathing device comprises a face mask, an inhaler and/or a nebulizer.

3. The device of claim 1, wherein the gaseous fluid comprises air, a treatment gas, a therapeutic agent, or a combination thereof.

4. The device of claim 3, wherein the therapeutic agent is selected from the group consisting of 4-methylumbelliferone (4-MU), palmitoylethanolamide (PEA), resveratrol, fisetin, $H_2$, nebulized hyaluronidase, and any combination thereof.

5. The device of claim 1, further comprising an isolation barrier.

6. The device of claim 5, wherein the isolation barrier is configured to isolate a user's head, head and torso, or entire body from ambient environment.

7. The device of claim 1, wherein the one or more sensors are configured to detect pressure, body position, heart rate, gaseous fluid content and/or level, body temperature, moisture, or a combination thereof.

8. The device of claim 1, further comprising a computer module in operable connection with the one or more sensors, the computer module configured to receive and process data from the one or more sensors to control inflation and deflation of the cavity and/or delivery of gaseous fluid.

9. The device of claim 8, wherein the processor is configured to maintain a static pressure within the cavity sufficient to expand the user's lungs and abdomen between inflation and deflation of the cavity.

10. The device of claim 1, wherein dimensions of the support layer are configured to be customized to the user by obtaining measurements of the user.

11. The device of claim 10, wherein the measurements are obtained by manual measurement of the user and/or imaging of the user.

12. The device of claim 11, wherein imaging comprises 1-dimensional (1-D), 2-dimensional (2-D) and/or 3-dimensional (3D) scans of the user.

13. A method of generating a respiratory assistance device of claim 1 customized for a user comprising:
   a) measuring the user's body, or portion thereof;
   b) manufacturing the support layer such that the first opening and/or the second opening conforms to the size and shape of the user; and
   c) securing the support layer to the support base, thereby generating a customized respiratory assistance device.

14. The method of claim 13, wherein measuring comprises manual measurement of the user and/or imaging of the user.

15. The method of claim 14, wherein imaging comprises 1-dimensional (1-D), 2-dimensional (2-D) and/or 3-dimensional (3D) scans of the user.

* * * * *